US008108384B2

(12) United States Patent
Sanchez et al.

(10) Patent No.: US 8,108,384 B2
(45) Date of Patent: Jan. 31, 2012

(54) MANAGING BIOLOGICAL DATABASES

(75) Inventors: Alejandro Sanchez, Salt Lake City, UT (US); Sofia Robb, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 603 days.

(21) Appl. No.: 10/532,198

(22) PCT Filed: Oct. 22, 2003

(86) PCT No.: PCT/US03/33590
§ 371 (c)(1),
(2), (4) Date: Aug. 8, 2005

(87) PCT Pub. No.: WO2004/037994
PCT Pub. Date: May 6, 2004

(65) Prior Publication Data
US 2007/0027630 A1    Feb. 1, 2007

Related U.S. Application Data

(60) Provisional application No. 60/420,216, filed on Oct. 22, 2002.

(51) Int. Cl.
*G06F 17/30* (2006.01)
(52) U.S. Cl. ........................ 707/722; 707/758
(58) Field of Classification Search .................. 707/722, 707/758
See application file for complete search history.

(56) References Cited

U.S. PATENT DOCUMENTS

| | | | | |
|---|---|---|---|---|
| 5,471,622 A * | 11/1995 | Eadline | ............................. | 707/3 |
| 5,852,715 A * | 12/1998 | Raz et al. | ....................... | 709/201 |
| 5,859,972 A * | 1/1999 | Subramaniam et al. | ...... | 709/203 |
| 6,023,659 A * | 2/2000 | Seilhamer et al. | .............. | 702/19 |
| 6,303,297 B1 | 10/2001 | Lincoln et al. | | |
| 6,343,275 B1* | 1/2002 | Wong | ............................... | 705/26 |
| 6,351,753 B1* | 2/2002 | Jagadish et al. | ............. | 707/203 |
| 6,363,399 B1 | 3/2002 | Maslyn et al. | | |
| 6,649,391 B1* | 11/2003 | Luche et al. | .................. | 435/196 |
| 6,660,841 B1* | 12/2003 | Sassone-Corsi | ............. | 530/350 |
| 6,920,396 B1* | 7/2005 | Wallace et al. | ................. | 702/19 |
| 7,231,390 B2* | 6/2007 | Blair et al. | ........................ | 707/6 |
| 2001/0049676 A1* | 12/2001 | Kepler et al. | ..................... | 707/3 |
| 2002/0072865 A1 | 6/2002 | Hogue et al. | | |
| 2002/0102604 A1 | 8/2002 | Edwards et al. | | |
| 2002/0194173 A1* | 12/2002 | Bjornson et al. | .................. | 707/4 |
| 2003/0036857 A1* | 2/2003 | Yao et al. | ......................... | 702/20 |
| 2003/0054394 A1* | 3/2003 | Chin et al. | ......................... | 435/6 |
| 2003/0055683 A1* | 3/2003 | Gibson et al. | ..................... | 705/2 |
| 2003/0118599 A1* | 6/2003 | Algate et al. | ....................... | 435/6 |

(Continued)

OTHER PUBLICATIONS

Globus, "GridFTP Universal Data Transfer for the Grid", Sep. 5, 2000, The University of Chicago and The University of Southern California, http://www.globus.org/toolkit/docs/3.0/gridftp/C2WPdraft3.pdf.*

(Continued)

*Primary Examiner* — Son T Hoang
(74) *Attorney, Agent, or Firm* — Ballard Spahr LLP

(57) ABSTRACT

Methods and systems for managing biological databases. The methods and systems can comprise creation, organization, and presentation of biological databases. The biological databases can be created using data obtained from a plurality of other databases and periodically updated. An executive summary can be created for a biological sequence using the biological database.

23 Claims, 36 Drawing Sheets

U.S. PATENT DOCUMENTS

2003/0125315 A1* 7/2003 Mjalli et al. ............. 514/210.01
2003/0133556 A1* 7/2003 Naik et al. ............... 379/201.12
2003/0217078 A1* 11/2003 Carlson et al. ................ 707/200

OTHER PUBLICATIONS

Ringwald et al. (GXD: a Gene Expression Database for the laboratory mouse, published in 1998, pp. 106-112).*

Altschul et al., "Gapped BLAST and PSI-BLAST: a new generation of protein database search programs." *Nucleic Acids Res.* 25(17):3389-3402 (1997).

Altschul et al., "Basic Local Alignment Search Tool." *J. Mol. Biol.* 215:403-410 (1990).

Jackson et al., "Improving Cluster Utilization Through Set Based Allocation Policies," presented at Proceedings International Conference on Parallel Processing, Valencia, Spain (2001).

Lawrence and Reilly, "An Expectation Maximization (EM) Algorithm for the Identification and Characterization of Common Sites in Unaligned Bipolymer Sequences." *Proteins: Structure, Function, and Genetics* 7:41-51 (1990).

Lawrence et al., "Detecting Subtle Sequence Signals: A Gibbs Sampling Strategy for Multiple Alignment," *Science* 262:208-214 (1993).

Liu and Lawrence, "Bayesian Inference on biopolymer models." *Bioinformatics* 15(1):38-52 (1999).

Liu et al., "Bayesian Models for Multiple Local Sequence Alignment and Gibbs Sampling Strategies." *Journal of the American Statistical Association* 90(432):1156-1170 (1995).

Liu et al., "Markovian Structures in Biological Sequence Alignments." *J. Amer. Stat. Assoc.* 94(445):1-15 (1999).

Sanchez et al., "The *Schmidtea mediterranea* database as a molecular resource for studying platyhelminthes, stem cells and regeneration." *Development* 129:5659-5665 (2002).

Williams and Zobel, "Indexing and Retrieval for Genomic Database." *IEEE Transactions on Knowledge and Data Engineering* 14(1):63-78 (2002).

* cited by examiner

Search *Schmidtea mediterranea* EST Database
Frequency Distribution | SmedDb Flowchart | Functional Distribution Please check off a Category and/or Sub-categories to search, or type in an Accession Number:

Search via Accession Number: ☐

[search by Accession Number]

- ☐ Cell defense (32)
  - ☐ carrier proteins (2)
  - ☐ DNA repair (2)
  - ☐ immunology (?) (0)
  - ☐ stress response (26)

- ☐ Cytoskeletal/Structural (139)
  - ☐ intermediate filaments (10)
  - ☐ microfilaments (47)
  - ☐ microtubules (35)
  - ☐ others (27)
  - ☐ thick/thin filaments (20)

- ☐ General Metabolism (228)
  - ☐ amino acids (25)
  - ☐ lipids (66)
  - ☐ nucleotides (18)
  - ☐ other enzymes/cofactors (56)
  - ☐ sugar/glycolysis (65)

- ☐ Mitochondria (72)

- ☐ Protein Metabolism (175)
  - ☐ degradation (63)
  - ☐ folding (23)
  - ☐ post-translational modification (10)
  - ☐ ribosomal components (39)
  - ☐ translation factors (32)
  - ☐ tRNA synthesis (10)

- ☐ Secretary Pathways (88)
  - ☐ endoplasmic reticulum (27)
  - ☐ golgi (28)
  - ☐ vesicular components (33)

- ☐ CELL-cell communication (136)
  - ☐ adhesion (27)
  - ☐ extracellular matrix (33)
  - ☐ hormone/growth factors/activators (19)
  - ☐ other membrane proteins (34)
  - ☐ receptors (24)

- ☐ DNA Replication/Modification (130)
  - ☐ apoptosis (31)
  - ☐ cell cycle/division (56)
  - ☐ chromosome/nuclear structure (21)
  - ☐ DNA synthesis (22)

- ☐ Intracellular Signaling (211)
  - ☐ channels/transporters (39)
  - ☐ effectors/modulators (39)
  - ☐ protein kinases (44)
  - ☐ protein phosphatases (16)
  - ☐ transduction (37)

- ☐ No Match (1281)

- ☐ RNA Metabolism (137)
  - ☐ RNA binding (17)
  - ☐ RNA polymerases (2)
  - ☐ RNA processing (44)
  - ☐ transcription factors (77)

- ☐ Unknown Function (357)
  - ☐ invertebrates (175)
  - ☐ plants (12)
  - ☐ Prokaryotes (9)
  - ☐ vertebrates (159)
  - ☐ yeast (4)

[search by categories]

Search via blast          [reset]

```
BLASTM 2.1.2 [Nov-13-2000]

Reference:
Altscnui, Stephen F., Thomas L. Madden, Alejandra A. Schffer,
Jinghui Zhang, Zheng Zhang, Webb miller, and David Lipman (1997),
"Gapped BLAST and PSI-BLAST: a new generation of protein database search
programs", Nucleic Acids Res. 25:3389-3402.

Query TEST
       (1828 letters)

Database: Smed
         3890 sequences; 2,526,228 total letters

Score      E
Sequences producing significant alignments:        (bits)    Value ref|Smed4531|D21.6.Contig              2495    0.0
ref|Smed3960|HB.24.7g                    36    0.057
ref|Smed2705|H.97.6h                     36    0.057
ref|Smed2761|H.9.7f                      34    0.23
ref|Smed3456|H.111.3b                    34    0.23
ref|Smed2084|H.83.9h                     34    0.23
ref|Smed1429|H.44.7g                     34    0.23
ref|Smed3687|H.44.2c(T3)                 32    0.89
ref|Smed3653|H.86.9d                     32    0.89
ref|Smed3328|H.2.7a                      32    0.89
ref|Smed3058|H.50.4e                     32    0.89
ref|Smed1991|H.57.2c                     32    0.89
ref|Smed1880|H.59.12c                    32    0.89
ref|Smed448|H.17.3e                      30    0.89
ref|Smed4748|HB.9.4f                     30    3.5
ref|Smed4734|H.67.11d(T3)                30    3.5
ref|Smed4692|H.73.7c                     30    3.5
ref|Smed4308|HB.35.4e                    30    3.5
ref|Smed4263|HB.29.8e                    30    3.5
ref|Smed4244|HB.22.6a                    30    3.5
ref|Smed3859|H.98.8c(T3)                 30    3.5
```

FIG.5B-1

```
ref|Smed3806|H.29.9d(T3)         30   3.5
ref|Smed3670|H.40.7b(T3)         30   3.5
ref|Smed3284|H.29.10f            30   3.5
ref|Smed3224|H.30.1e             30   3.5
ref|Smed3143|H.38.10f            30   3.5
ref|Smed2842|H.9.4b              30   3.5
ref|Smed2143|H.35.6a(T3)         30   3.5
ref|Smed1718|H.49.1d(T3)         30   3.5
ref|Smed1992|H.6.1e              30   3.5
ref|Smed1332|H.104.5d            30   3.5
ref|Smed1208|H.83.7g             30   3.5
ref|Smed1167|H.24.6d             30   3.5
ref|Smed476|H.92.5f              30   3.5
ref|Smed464|H.69.2a              30   3.5

>ref|Smed4531|D21.6.Contig
         Length = 1828

Score = 2495 bits (1258), Expect = 0.0
 Identities = 1281/1281 (100%)
 Strand = Plus / Plus Query: 1     cttctgcaaggtccacagttaccattaacaaatcgagtcctgcagtaaaggaatatgaaa 60
             ||||||||||||||||||||||||||||||||||||||||||||||||||||||||||||
Sbjct: 1     cttctgcaaggtccacagttaccattaacaaatcgagtcctgcagtaaaggaatatgaaa 60

Query: 61    tgagacaatcctacaattttctggagcacctatgggggatcagttcaaattcatagca 120
             ||||||||||||||||||||||||||||||||||||||||||||||||||||||||||||
Sbjct: 61    tgagacaatcctacaattttctggagcacctatgggggatcagttcaaattcatagca 120
```

FIG.5B-2

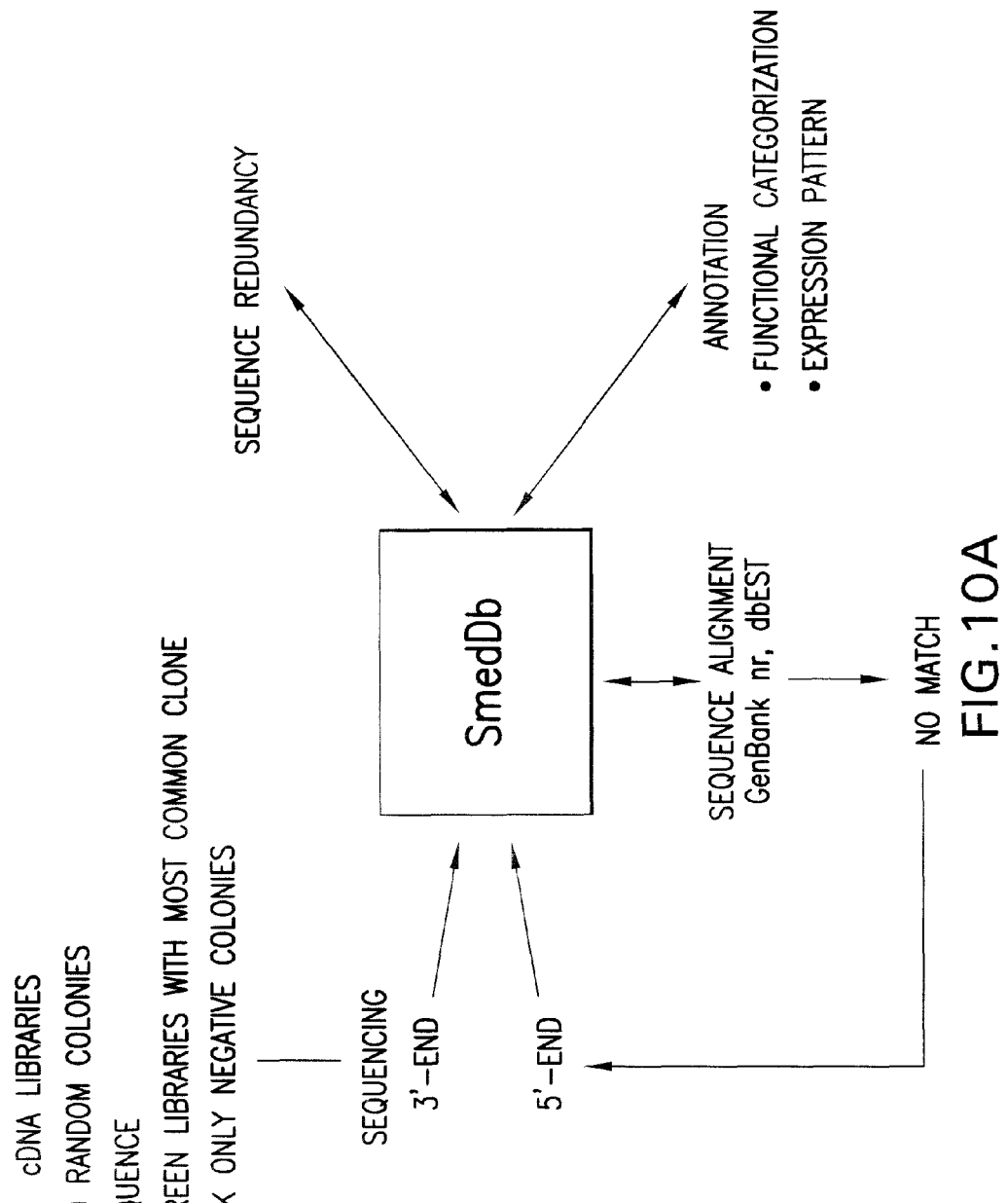

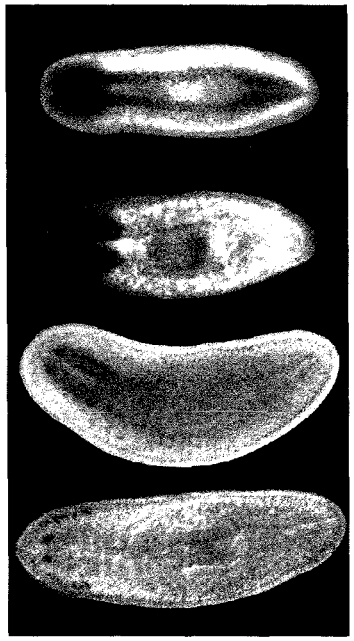
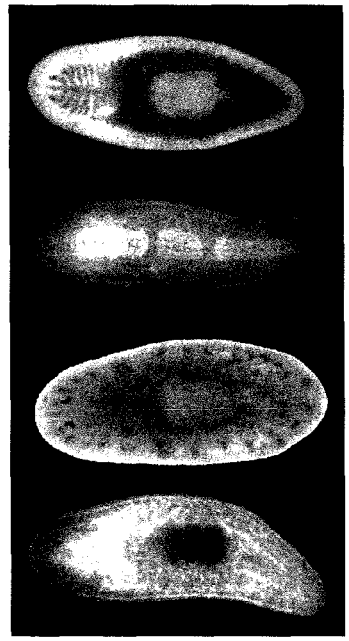
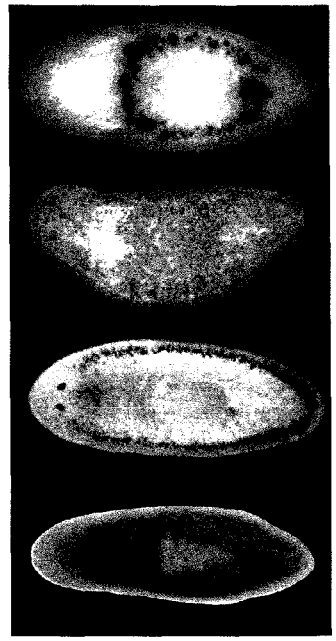
FIG.11A  FIG.11B  FIG.11C
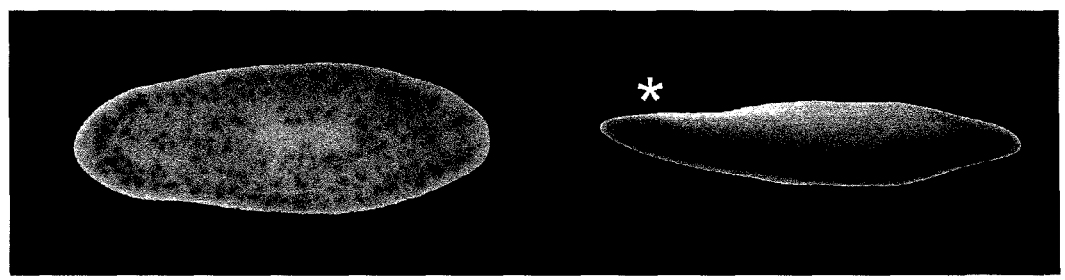
FIG.11D

```
#!/usr/sbin/perl

#check if this is a first time search on the input files

print "Is this a first time search on datafiles in \$HOME/newsearch (reply yes or no): ";
chomp($flag1 = <STDIN>);

if ($flag1 eq 'yes') {
$direct = newsearch;
}

#if not a first time search

if (#flag1 eq 'no') {
$direct = search;
}

#check if new db available - if no then exit
```

FIG.14A

```

$max = @dirs[0];
foreach $n (@dirs) {
    if ($n gt $max)
        {$max = $n;}
}

# Now, $max is the latest date-coded directory

$Dir_ID = $max;

$date_last = qx (grep Posted /ufs/inscc.utah.edu/common/home/planaria/$direct/$Dir_ID/1x12.htm | uniq |cut -d "
" -f 8,9,10);

#Again change format
#Turn date_last into something useful

($m, $d, $y) = split(/ ,?/, $date_last);
if ($m eq 'Jan')
    {$month = '01';}
if ($m eq 'Feb')
    {$month = '02';}
if ($m eq 'Mar')
    {$month = '03';}
if ($m eq 'Apr')
    {$month = '04';}
if ($m eq 'May')
    {$month = '05';}
if ($m eq 'Jun')
    {$month = '06';}
if ($m eq 'Jul')
    {$month = '07';}
```

FIG.14B-1

```
if ($m eq 'Aug')
   {$month = '08';}
if ($m eq 'Sep')
   {$month = '09';}
if ($m eq 'Oct')
   {$month = '10';}
if ($m eq 'Nov')
   {$month = '11';}
if ($m eq 'Dec')
   {$month = '12';}

$d =~ s/,//;
if ($d < 10)
   {$d = '0' . $d} chomp ($y);

$date_last_useful= "$y-$month-$d";
print "Date of last database: ", $date_bd_useful,"\n";

print "Date of last search db: ", $date_last_useful,"\n";

#Compare two dates-if first not later than second exit with message

```

FIG.14B-2

```
if (date_db_useful le $date_last_useful)
    {die "No database update since last search. Try again tomorrow as updates are checked for nightly\n";}
}

#check if both searches or only first to be done

print "Do you want to do the first search only (enter 1) or fist search and tblastx search (enter 2): ";
chomp($flag = <STDIN>);
print "The information that follows are the jobids for the batch jobs submitted to complete the search.\n";
print"\n";

#do first stage of search

#figure out how many nodes are free to use for search

$busy = qx(showq|grep Nodes|cut -d " " -f26);
$active = qx(showq|grep Nodes|cut -d " " -f31);
$noes = $active - $busy;
if ($nodes == 0)
    {$nodes = 1;}
print "NODE TO BE USED: ", $nodes, "\n";

#make necessary directory for output of search

($DAY, $MONTH, $YEAR) = (localtime)[3,4,5];
$MONTH++;
if ($MONTH < 10)
    {$MONTH = '0'.$MONTH;}
if ($DAY < 10)
    {$DAY = '0'.$DAY;}
```

FIG.14C-1

```
$YEARS = $YEAR + 1900;
if ($flag eq 1)
{system("mkdir -p \$HOME/$direct/$YEARS-$MONTH-$DAY");}
else
{system("mkdir -p \$HOME/$direct/$YEARS-$MONTH-$DAY/TBLASTX");}

#set up scripts for first search

$source = "$ENV{HOME}/$direct/searchlist.in";
open(IN, " $source");
@line = <IN>;
foreach (@line)
{chomp;}

#Write out PBS header to each of the SCRIPT files being written

foreach (1..$nodes){
    $name = "#ENV{HOME}/$direct/SCRIPT-S_";
    open ($name, ">$name");
    print $name ("#PBS -S /bin/csh\n");
    print $name ("#PBS -q sequence\n");
    print $name ("#PBS -W qos=2\n");
    print $name ("#PBS -l walltime=500:00:00,nodes=1:ppn=2\n");
    print $name ("#PBS -N Blast", "$_", "\n");
    print $name ("#PBS -e blast", "$_", ".stderr\n");
    print $name ("#PBS -o blast", "$_", ".stdout\n");
```

FIG.14C-2

```perl
print $name ("setenv BLAST_CLI_HOME /uufs/sequence/sys/pkg/blast/std\n");
print $name ("setenv BLAST_DB /scratch/local/sofia/db\n");
print $name ("setenv WORKDIR \$HOME/$direct\n");
print $name ("cd \$WORKDIR/",$YEARS,"-",$MONTH,"-",$DAY,"\n");
print $name ("ln -s \$BLAST_CLI_HOME/.ncbirc .ncbirc\n");

print $name ("rm -r /scratch/local/sofia/db\n");
print $name ("mkdir -p /scratch/local/sofia/db\n");
print $name ("cp /uufs/sequence/sys/pkg/blast_db/std/nr.* /scratch/local/sofia/db/.\n");
print $name ("cp /uufs/sequence/sys/pkg/blast_db/std/nt.* /scratch/local/sofia/db/.\n");
print $name ("cp /uufs/sequence/sys/pkg/blast_db/std/sts.* /scratch/local/sofia/db/.\n");
print $name ("cp /uufs/sequence/sys/pkg/blast_db/std/est.* /scratch/local/sofia/db/.\n");
print $name ("cp /uufs/sequence/sys/pkg/blast_db/std/gss.* /scratch/local/sofia/db/.\n");
print $name ("cp /uufs/sequence/sys/pkg/blast_db/std/htgs.* /scratch/local/sofia/db/.\n");
}
$x = 1;

# Loop through input sequence file name in the file searchlist.in and generate
# the actual part of the PBS scripts that does the searches

foreach $line (@line) {
    $name = "$ENV {HOME}/$direct/SCRIPT-$x";
    if ($line =~ m/#x#/)
    {print $name ("\$BLAST_CLI_HOME/blastall -a 2 -p blastx -e 1 -b 5 -v 5 -d \$BLAST_DB/nr -i ../$line -o $line.htm -T T \n");
    if ($flag eq 2)
        {print $name ("perl /uufs/sequence/sys/pkg/blast/tblast_single.pl $line\n");
        print $name ("cd TBLASTX\n");
        $line =~ s#x#t#;
        print $name ("\$BLAST_CLI_HOME/blastall -a 2 -p tblastx -e 1 -b 5 -v 5 -d \"\$BLAST_DB/nt
```

FIG. 14D-1

```
\$BLAST_DB/sts \$BLAST_DB/est\$BLAST_DB/gss\$BLAST_DB/htgs\" -i ../$line -o $line.htm -T T \n");
        print $name ("cd ..\n");
    }
    if ($line =~ m#n#)
        {print $name ("\$BLAST_CLI_HOME/blastall -a 2 -p blastn -e 1 -b 5 -v 5 -d \"\$BLAST_DB/nt
\$BLAT_DB/sts \$BLAST_DB/est \$BLAST_DB/gss \$BLAST_DB/htgs\" -i ../$line -o $line.htm -T T \n");
    $x++;
    if ($x > $nodes)
        {$x = 1;}
}

#submit search jobs

foreach (1..$nodes){
    $name = "$ENV{HOME}/$direct/SCRIPT-$_";
    close ($name, ">$name");
    qx(qsub $name);
}

# Print message to user that script have been successfully submitted

print "All batch jobs have been submitted . Check periodically by logging into sequence and doing a showq. Output
files will be found in $ENV{HOME}/$direct/$YEARS-$MONTH-$DAY for the first stage search and
$ENV{HOME}/$direct/$YEARS-$MONTH-$DAY/TBLASTX for the second stage search\n";
```

FIG.14D-2

```
#first get date of current database and store in date_db

qx(ln -s /uufs/sequence/sys/pkg/blast/std/.ncbirc .ncbirc);
$date_db = qx(/uufs/sequence/sys/pkg/blast/std/fastacmd -d /uufs/sequence/sys/pkg/blast_db/std/nr -I|grep Date|
cut -d " " -f5,6,7);

# Turn date_db into something useful

($m, $d, $y) = split(/ ,?/, $date_db);
if ($m eq 'Jan')
    {$month = '01';}
if ($m eq 'Feb')
    {$month = '02';}
if ($m eq 'Mar')
    {$month = '03';}
if ($m eq 'Apr')
    {$month = '04';}
if ($m eq 'May')
    {$month = '05';}
if ($m eq 'Jun')
    {$month = '06';}
if ($m eq 'Jul')
    {$month = '07';}
if ($m eq 'Aug')
    {$month = '08';}
if ($m eq 'Sep')
    {$month = '09';}
if ($m eq 'Oct')
    {$month = '10';}
```

FIG.14E-1

```
if ($m eq 'Nov')
    {$month = '11';}
if ($m eq 'Dec')
    {$month = '12';}

$d =~ s/,//;
if ($d < 10)
    {$d = '0'.$d} chomp ($y);

$date_db_useful = "$y-$month-$d";

#get date of database used in last search and store in date_last
#Parse date format to find newest directory

#@files is a list of all files in the search directory
#@dirs is a list of only the date directories in that search directory

@files = qx(ls #ENV{HOME}/$direct);
foreach (@files)
    {chomp;}
foreach (@files) {
    if (m#\d+-\d+-\d+#)
        {push @dirs, $_;}
}

#Find the greatest string in @dirs
```

FIG. 14E-2

```
#PBS -S /bin/csh
#PBS -q sequnce
#PBS -W qos=2
#PBS -l walltime=222:00:00,nodes=1:ppn=2
#PBS -N Blast2
#PBS -e blast2.stderr
#PBS -o blast2.stdout

# set all environment variables needed

setenv BLAST_CLI_HOME /uufs/sequence/sys/pkg/blast/std
setenv BLAST_DB /scratch/local/sofia/db
setenv WORKDIR $HOME/seq_dev_2/search

#move to proper directory

cd $WORKDIR/2003-07-16

#link needed so Blast works

ln -s $BLAST_CLI_HOME/.ncbirc .ncbirc

#Clean up local scratch from last run and get local copy of all
#necessary databases

rm -r /scratch/local/sofia/db
mkdir -p /scratch/local/sofia/db
cp /uufs/sequence/sys/pkg/blast_db/std/nr.* /scratch/local/sofia/db.
cp /uufs/sequence/sys/pkg/blast_db/std/nt.* /scratch/local/sofia/db.
```

FIG. 15A

```
cp /uufs/sequence/sys/pkg/blast_db/std/sts.* /scratch/local/sofia/db.
cp /uufs/sequence/sys/pkg/blast_db/std/est.* /scratch/local/sofia/db.
cp /uufs/sequence/sys/pkg/blast_db/std/gss.* /scratch/local/sofia/db.
cp /uufs/sequence/sys/pkg/blast_db/std/htgs.* /scratch/local/sofia/db.

#The rest of the script runs the searches for the given input files (2x12, 9x12, and 16x12 shown)
#This particular script does both the first and second stage searches on each file;
#between the two stages the output of the first stage is parsed to check for searches
#in which "No hits found"; for these searches the second stage input files are then created.

$BLAST_CLI_HOME/blastall -a 2 -p blastx -e 1 -b 5 -v 5 -d $BLAST_DB/nr -i ../2x12 -o 2x12.htm -T T
perl /uufs/sequence/sys/blast/tblast_single.pl 2x12
cd TBLASTX
$BLAST_CLI_HOME/blastall -a 2 -p tblastx -e 1 -b 5 -v 5 -d "$BLAST_DB/nt $BLAST_DB/sts $BLAST_DB/est
$BLAST_DB/gss $BLAST_DB/htgs" -i ../2x12 -o 2x12.htm -T T
cd ..
$BLAST_CLI_HOME/blastall -a 2 -p blastx -e 1 -b 5 -v 5 -d $BLAST_DB/nr -i ../9x12 -o 9x12.htm -T T
perl /uufs/sequence/sys/blast/tblast_single.pl 9x12
cd TBLASTX
$BLAST_CLI_HOME/blastall -a 2 -p tblastx -e 1 -b 5 -v 5 -d "$BLAST_DB/nt $BLAST_DB/sts $BLAST_DB/est
$BLAST_DB/gss $BLAST_DB/htgs" -i ../9x12 -o 9x12.htm -T T
cd ..
$BLAST_CLI_HOME/blastall -a 2 -p blastx -e 1 -b 5 -v 5 -d $BLAST_DB/nr -i ../16x12 -o 16x12.htm -T T
perl /uufs/sequence/sys/blast/tblast_single.pl 16x12
cd TBLASTX
$BLAST_CLI_HOME/blastall -a 2 -p tblastx -e 1 -b 5 -v 5 -d "$BLAST_DB/nt $BLAST_DB/sts $BLAST_DB/est
$BLAST_DB/gss $BLAST_DB/htgs" -i ../16x12 -o 16x12.htm -T T
cd ..
```

MANAGING BIOLOGICAL DATABASES

This application claims priority to U.S. provisional patent application 60/420,216, filed Oct. 22, 2002, which is herein incorporated by reference in its entirety.

I. ACKNOWLEDGEMENTS

This work was partially funded by the National Institutes of Health, National Institute of General Medical Sciences RO-1 GM57260 and National Center for Research Resources grant 1 S10 RR17214-01 and F32-GM19539.

II. BACKGROUND

There has been a tremendous increase in the amount of sequence information that has been produced. The management of sequence information has become more and more complicated as the number of sequences and the number of sequenced genomes increases. There is a tremendous need for data analysis systems capable not only of handling the continually increasing amount of sequence information, but also managing other information that is associated with a given sequence, such as functional information, expression information, homology information, an the like. Disclosed are methods and systems which aid in the storage, analysis, and updating of biological information. Also disclosed is an extensive EST database for the planarian worm, *S. mediterranea*. The database containing the sequence information related to *S. mediterranea* exemplifies the disclosed database systems and methods. Also disclosed are clonal lines of *S. mediterranea* which can be used, for example, as tools in the study of flatworms, including, using them in studies designed to isolate therapeutic agents targeting planaria in general, and *S. mediterranea* in particular.

III. SUMMARY

Disclosed are methods and compositions related to database formation and comparison. Also disclosed are methods of creating a database, as well as methods of using the database. Also disclosed are systems for managing the disclosed databases. Also disclosed are clonal lines of *S. mediterranea* as well as methods of using these clonal lines as well as making them.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 is a frequency distribution of clones isolated from *S. mediterranea*. The results indicate the complexity of the libraries utilized. Of 5,561 cDNA clones randomly selected from these libraries, almost 3,000 were unique, and over 2,000 of these were selected only once. The Poisson distribution results are meant to be an approximation only.

FIG. 2 is an individual EST record interface. Each EST record includes identification name (EST ID), GenBank accession number, cDNA sequence, functional category and subcategory, in situ data (if available), and GenBank BLAST results. The GenBank BLAST results contain links to Entrez-PubMed. All individual entries are updated automatically once a week.

FIG. 3 is a search interface of SmedDb, accessible anywhere within the site by selecting "SmedDB Search" from the top or side menus. Clones can be searched by name or accession number. Also, an internal BLAST search is available for researchers to compare their cDNA sequences against the planarian sequence database.

FIG. 4 is a query result interface. Provides basic information such as clone name and accession number, description, categorization and availability of in situ data.

FIG. 5 is a Blast search and results interface. Section A illustrates that BLAST in SmedDb can be accessed from the side and top menus as well as at the bottom of the "SmedDb Search" interface (FIG. 3). This interface requires the input of a search name and a query sequence. Currently, SmedDb BLAST can run BLASTn for nucleotide vs. nucleotide comparisons, and tBLASTn for amino acid vs. nucleotide comparisons. Section B illustrates that after submitting a comparison query SmedDb will produce a search return containing all matches with score and expentancy values. In order to facilitate interpretation, all SmedDb cDNAs identified by the search as potential homologues are hyperlinked to the individual EST interface (FIG. 2).

FIG. 6 is a block diagram 100 illustrating the database manager and output generator software 102. The database manager and output generator 102 stores data in the database 104 and uses the database 104 to generate output data and forms 106. The database manager and output generator 102 also is in periodic communication with GenBank 108 and other publicly available servers such as Pfam, Prodom, Prosite, Tmpred and Signal P, among others. Many different kinds of data can be stored in the database 104. It will be appreciated that the *Schmidtea mediterranea* Database (SmedDb) is only one possible database embodiment out of many. With the system 100 as shown in FIG. 6, a user can upload multiple sequences. The system can handle hundreds at a time in various formats (e.g., ABI *.Seq format). The program checks 102 for redundancy with other sequences that have been stored. If the sequence is unique the program 102 will add this sequence to the database 104 with the sequence identifier (file name). The program 102 will also send all the unique sequences to GenBank 108 and/or other relevant servers (Pfam, Prodom, etc.) for comparison. When all the GenBank 108 replies have been received an option can be chosen which will save all of the GenBank 108 replies in the database 104 and the scores and expect values are extracted and input into the database 104. If the score is of an appropriate value, the matching description is also extracted from the GenBank 108 returned and saved in the database 104. The sequences can be sorted by categories, subcategories and keywords. Images displaying the expression patterns of these sequences can also very easily be uploaded individually or in batches and added to the database 104 for convenient viewing of GenBank 108 return, sequence quality and expression pattern. If the sequence which is initially uploaded and compared to the database 104 is a copy of a record already in the database 104, the sequence name will be stored as being a copy of the original sequence. This program 102 also has the ability to search sequence data by name, description (from GenBank 108 returns), data of receipt of GenBank 108 returns, category, subcategory, keyword and accession number. In addition, it is web-browser savvy allowing users to access and analyze sequence information easily via the Internet using a web browser. The database manager and output generator 102 can embed hyperlinks and web-browser data into the output forms and data 106 so that the output 106 can be easily viewed through use of a web browser.

FIG. 7 is a block diagram 200 illustrating the database manager and output generator software 202 operating through use of one or more computer networks 210. The database manager and output generator 202 stores data in the database 204 and uses the database 204 to generate output data and forms 206. The database manager and output generator 202 also is in periodic communication with GenBank 208 and/or other publicly available databases 209 such as Pfam, Prodom, Prosite, Tmpred and Signal P, among others. Many different kinds of data can be stored in the database 204. It will be appreciated that the *Schmidtea mediterranea* Database (SmedDb) is only one possible database embodiment out of many. The database manager and output generator 202 allows for streamlining of sequence data analyses, including expression patterns, microarray data, and GenBank 208 information. Such seamless integration of capabilities facilitates data mining and extraction of biologically relevant data that are suitable for wet-lab experimental testing. The database manager and output generator 202 can be implemented through one or more computer programs, whether scripts, executables, libraries, etc.

FIG. 8 is a flow diagram of the SmedDb database as disclosed herein. As shown and as discussed above, the SmedDb includes cDNA sequences and checks for sequence redundancy. The SmedDb can include annotations including functional categorizations and expression patterns.

FIG. 9 is a diagram illustrating one possible relational database that can be used as the database 104, 204. Of course, changes can be made by those skilled in the art based on any additional records that need to be stored or based on the deletion of any records that can not be needed. The various records and relationships shown in FIG. 9 are labeled and correspond with the disclosure herein and/or will be appreciated by those skilled in the art.

FIG. 10 shows a bioinformatics and categorization of *S. mediterranea* sequences. (A) Organigram depicting the steps performed to produce a non-redundant collection of *S. mediterranea* cDNA sequences (SmedDb). Bioinformatic analyses compared the database against itself to identify and remove redundant clones before sending sequences to the public databases. The GenBank protein and nucleotide collections as well as the EST database (dbEST) were queried using the BLAST algorithm. Sequences returning significant matches (E less than or equal to $10^{-4}$) were subjected to annotation into functional categories based on the identity/function of the GenBank match. (B) Distribution of informative sequences by functional categories. For simplicity the cell signaling category includes the cell/cell communication and internal signaling categories. Metabolism is an amalgamation of the general metabolism, mitochondria and protein metabolism categories. (C) Distribution by percentage of planarian genes displaying highest similarities with members of either the vertebrates or invertebrates.

FIG. 11 shows the representative results of high-throughput, whole-mount in situ hybridization. (A-C) Probe identity corresponding to the images is given from top to bottom with each clone ID in parentheses as follows. (A) Gene expression patterns within the nervous system of *S. mediteraizea*: synaptotagmin (H.6.7h); quinoid dihydropteridine reductase (H.9.5b); pax6 (H.109.7h) and degenerin (H.112.3c). (B) Gene expression patterns in organ systems: gastrovascular system (D.14; unknown function), dorsal epithelium (H.7.1e; gp25L/p24 family), excretory system (H.14.9d; carbonic anhydrase); and pharynx (H.14.11f; unknown function). (C) Gene expression in discrete cell types: matrix metalloproteinase (A115) in central secretory cells; epithelial cells (H.12.11a; intermediate filament); subepidermal marginal adhesive gland cells (H.1.3b; zonadhesin); and free-mesenchymal cells (neoblasts) expressing piwi (H.2.12c). (D) Ventral view (left) of clone H.8.1f (unknown function), and lateral view of the same specimen (right) demonstrate a dorsoventral segregation of differentiation. The red asterisk indicates the position of the pigmented photoreceptor. Anterior is to the left in all panels.

FIG. 12 shows regulation of cell number in planarians of different lengths. (A) In situ hybridization of clone H112.3c, showing distribution of putative chemoreceptive neurons underlying anterior margin. Nomarski DIC view. Scale bar: 100 mm. (B) Number of H112.3c-positive cells/side in organisms of different lengths. Mean number of H112.3c-positive cells (±s.d.) is indicated (for 1 mm, n=14; 2 mm, n=9; 6 mm, n=10; 8 mm, n=7).

FIG. 13 shows the final hardware configuration for the cluster (Example 3) consists of eight dual processor AMD Athlon MP 2000+ search nodes each with 2 GB of RAM and a moderate (60 GB) amount of local disk provided for the option of using local space for storage of the database files. The core file server, used to provide the global disk space, is also a dual AMD Athlon MP 2000+ with 1 GB of RAM and 240 GB of usable space in a RAID array configuration, optimized for NFS read performance. This node is also used to provide cluster services like scheduling, accounting, etc. A specialized node was added for processing the daily updates of the database files.

FIG. 14 shows A perl script, which was developed to create the necessary PBS script files which distribute the searches among the available nodes in the cluster. This script is based on a file structure in which there is a directory $HOME/search which contains the input files. The $HOME/search directory also contains one additional file, searchlist.in, which is a list of the filenames, one per line, of the files containing sequences on which the stage one search must be completed. Each of these input files must exist in the $HOME/search directory. The researchers can add new search sequences by either adding them to an existing input file or creating a new input file. In the later case the filename, which must match the existing convention and have an n or x in the name, must be added to the searchlist.in file.

FIG. 15 shows the perl script then generates the #nodes scripts, named SCRIPT-1 through SCRIPT-#nodes. The necessary PBS headers are written to each of these script files, along with the necessary environmental variables and links. In addition, the first portion of each of these scripts involves cleaning up the local scratch space from previous searches followed by installing the necessary databases for the current search onto the local scratch system of each node. This is followed by a round robin process dividing up the searches among the #node script files, with the first input file name in searchlinst.in going to SCRIPT-1, the second to SCRIPT-2, etc until the last PBS script file is reached then returning to SCRIPT-1 and repeating the cycle until the end of searchlist.in is reached. Once the PBS script files are generated they are submitted by the perl script.

FIG. 16 shows the architecture of SmedDb as it relates to the cluster search system in Example 3. The FASTA files generated from SmedDb containing the sequences (ESTs) that need to be compared with the most recently updated version of NCBI databases are uploaded manually to the cluster search system using secure copy (scp). Using the script described above the required the BLAST searches are executed and the output files are downloaded to the SmedDb system also using scp. These search results are stored with the corresponding EST as well as being parsed by a Bioperl (A. Sanchez Alvarado, et al., "The *Schmidtea mediterranea* database as a molecular resource for studying platyhelminthes, stem cells and regeneration," *Development*, vol. 129, pp. 5659-65, 2002) script.

FIG. 20 shows a flow diagram for processing biological information.

V. DETAILED DESCRIPTION

Figure 1:
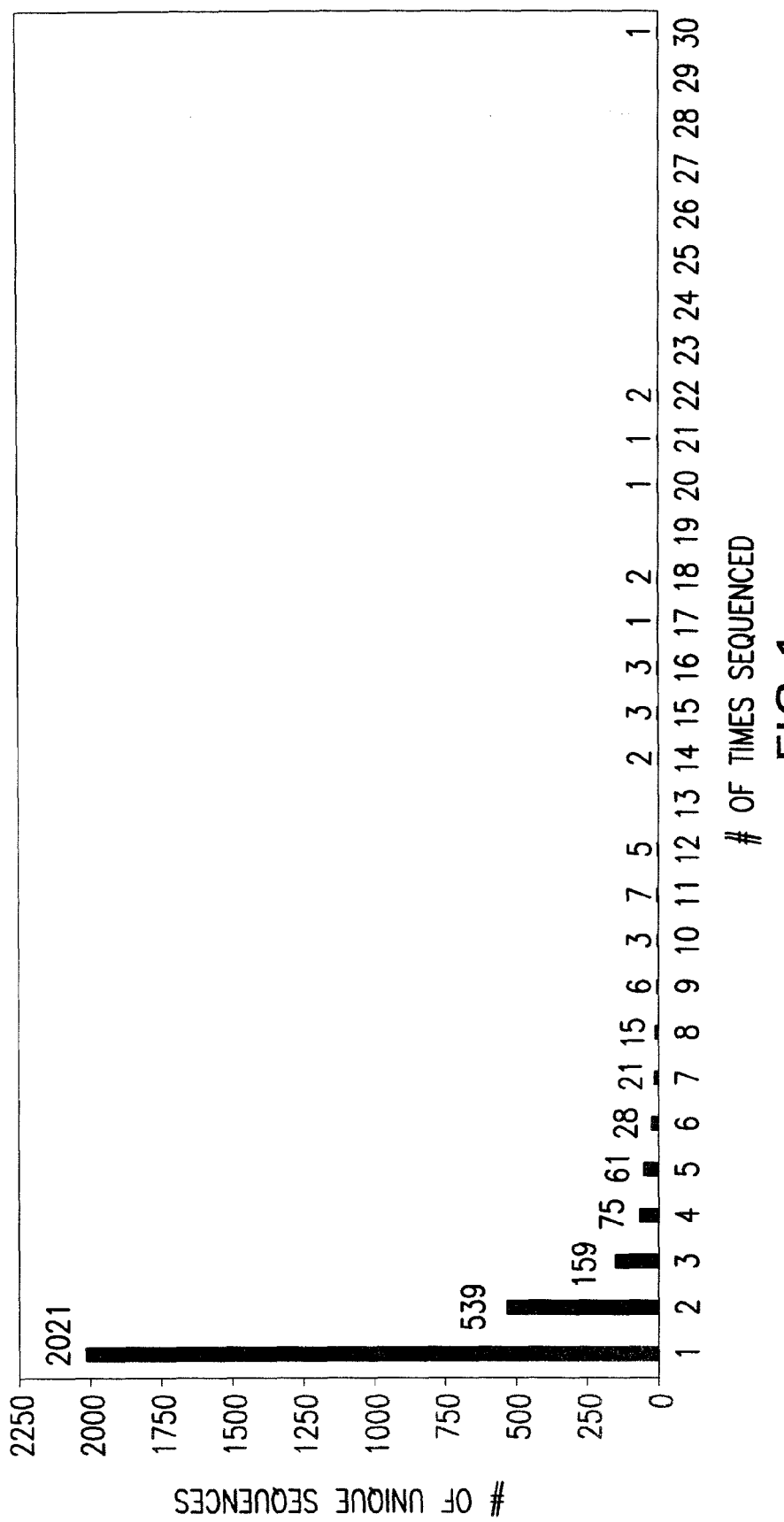

The disclosed compositions, methods, and systems relate to the management of database information, particularly biological database information. These compositions, methods, and systems can be used for any database, and are exemplified here with a database called SmedDb. SmedDb is a database that was based on the acquisition of over 3000 EST obtained from a clonal line of planaria, *Schmidtea mediterranea*. Not only are methods and systems disclosed for the management of databases, such as biological databases, but methods for the creation, organization, and presentation of biological databases is also disclosed. Method of using the databases and using the clonal lines are also disclosed. The systems and methods for managing the databases is discussed below, followed by a discussion of the presentation of the databases, which is followed by a discussion of the organisms known as planaria, their role in human disease, and the clonal lines which are disclosed herein and which can be used to screen for gene activity, as well as used, for example, as models for pharmaceutical development and testing.

A. DATABASE MANAGEMENT PROTOCOLS

Database management has at its core the storage of information and the manipulation of the records that contain that information, and importantly the access and searching of the records that contain that information. In many cases today, information is stored in computer systems which are remote to each other, but which are connected via the Internet or similar network system. Furthermore, there is unprecedented growth in the collection of information contained in databases, and unprecedented access to databases of information over the internet, but there are lacking systems and methods for managing the flow information between the plethora of databases that exist and are coming into existence each day. There is an ever growing need for databases to be able to communicate efficiently with one another in an efficient, and equally important, cost effective manner. The management of biological databases and the problems associated therein illustrate these general issues well, as information collection has grown tremendously in the last decade.

The development of methodologies such as high-throughput sequencing, DNA and protein microarrays as well as RNA interference has created an unprecedented opportunity to carry out functional genomic studies in organisms not readily suitable to genetic analyses, but have also led to almost unimaginable levels of sequence and functional information creation. In order to store, organize, manage and extract biologically significant information from the large datasets usually generated by such methodologies, it is imperative to create readily accessible, interactive, and easy to navigate repositories of data, and furthermore, to be able to manage the interaction between different databases that house different pieces of information.

In 1982, the number of sequences deposited in GenBank at the National Center for Biotechnology Information (NCBI), which has become one of the main, if not the main, repository for such information, was 606, comprised of only 680,338 base pairs. By 1996, the number of sequences reached a little over one million with a total of nearly 652 million base pairs. Today, GenBank is made up of over 22 million sequences representing almost 29 billion base pairs (http://www.ncbi.nlm.nih.gov/Genbank/genbankstats.html). Behind the precipitous rise of sequencing data during the past four years has been the equally rapid improvement of DNA sequencing methodologies. Such improvements have today made possible what in the mid-1990's was thought to be nearly impossible: to completely sequence the genomes of multicellular organisms, including *Homo sapiens* (R. Sachidanandam, et al., "A map of human genome sequence variation containing 1.42 million single nucleotide polymorphisms," *Nature*, vol. 409, pp. 928-33, 2001). In fact, in the next two years alone genome sequences for the chimpanzee, rhesus macaque, mouse, dog, cow, pig, chicken, zebrafish, the frog *Xenopus tropicalis*, sea urchin, honeybee, and the planarian *Schmidtea mediterranea* will be obtained and deposited in GenBank (http://www.genome.gov/page.cfm?pageID=10002154). The combined sequence data from these animals is expected to total 27 billion nucleotides, or roughly the same amount of sequence information available in GenBank today, thus doubling again the amount of information to be managed. It is clear, therefore, that the exponential growth of GenBank is unlikely to abate any time soon.

A further issue of the management of all of this sequence information is that because genetic sequences do not provide any direct biological information, researchers have to conduct experiments to determine the relationships between a genetic sequence and its biological function. These experiments include "wet" experiments, which are traditional experiments using physical materials and hypothesis to test and define the biological function and relationships of a particular sequence or the protein that it encodes. However, the experiments also include those that are founded in the comparison of one sequence to another or a set of other sequences, and comparing the function of one sequence to the function of another related sequence or set of sequences, in other words, by database comparisons and updating. This process can be significantly accelerated if one takes into account that there are significant similarities between genetic sequences associated with similar biological functionality across different species. Therefore, when determining the biological functionality of a new sequence it is of great value to find homologous sequences from other organisms in which their functionality is better understood. The disclosed compositions, methods, and systems are designed to facilitate the acquisition of biological information and to facilitate the mining, the comparison, and the collection of the different databases of such information. One type of data comparison that is used as an example herein is the comparison of one DNA sequence to another DNA sequence, looking for homologies and information regarding their relatedness, i.e. are they homologs or orthologs etc., and forming an alignment of the sequences. It is understood that the methods and systems and compositions disclosed herein can be used for any type of information comparison or acquisition or updating, and in fact, one beneficial aspect of the disclosed compositions, methods, and systems, is that they are scalable and can be utilized to address any kind of or set of data comparison or acquisition.

It is generally easy today to compare one sequence to each sequence contained in the national database for sequences, Genbank. Programs, such as BLAST, discussed herein can be accessed and run over the Internet and readily provide sequence comparison information for that sequence. Thus, the comparison of a single sequence to the set of 22 million or so sequences can be performed relatively quickly at any given moment of time. Two issues are beginning to arise in the current world of sequence comparison, and in data comparison in general: 1) the amount of database at Genbank (representative of different databases) is changing on a daily, or even continually, basis, meaning that to have an up-to-date analysis for any given sequence the single sequence needs to be continually compared to the Genbank database (which begins to cause significant time and resource issues, and 2) many laboratories and researchers are no longer focusing on a single sequence in their research, but rather are beginning more and more to focus on complete genomes, which causes the obvious problem of, for example, having to compare, each sequence in the genome to each sequence in Genbank, on a periodic, such as daily or continual basis. This clearly causes more time and resources problems.

As moderate- to high-throughput sequencing capabilities have become commonplace in many research institutions, the number of laboratories engaged in relatively large sequencing projects has increased. Therefore, individual groups obtaining thousands of new sequences in a matter of a few weeks are confronted by the impracticality of submitting each sequence individually for comparison. As discussed above, although possible, this practice is made unrealistic by the fact that such comparisons do not remain up-to-date for long due to the growth of the databases, and thus require frequent resubmission. Therefore, non-batched queries to the NCBI or institutional web based sites would make the proper analysis of the large amounts of DNA sequencing data an almost impossible task for the individual investigator.

In order to overcome the difficulties described the storage and organization of sequences and their BLAST results has been integrated with a low cost commodity based cluster computer system that can automatically, semi-automatically, or manually, if desired, process thousands of sequence to sequence comparisons, i.e. BLAST searches, when the NCBI databases change. The end result for the investigator is a dynamic database that is regularly and automatically updated to obtain the most up-to-date sequence comparisons available. The disclosed system and methods for managing this information can used for any type of database updating that is desired. The disclosed systems, take advantage of cluster computing, and implement methods and scripts that control the clusters capable of performing massive database comparisons and updating efficiently.

Cluster computing (G. F. Pfister, *In Search of Clusters*. Upper Saddle River, N.J.: Prentice Hall PTR, 1998) has always provided an attractive approach to provide computer resources to scientific problems. In recent years the introduction of commodity clusters using the LINUX operating system has provided special impetus to the use of cluster architectures in 5 technical and scientific environments, including Grid computing (F. Berman, G. Fox, and T. Hey, "Grid Computing: Making The Global Infrastructure a Reality." London: John Wiley & Sons, 2003, pp. 1080). Most reports in the literature address the design and implementation of these types of architectures as general purpose systems with an intended workload encompassing many scientific applications. None-the-less the ample configuration space available when designing a system using commodity hardware allows for specialization when desired.

The design, implementation and deployment of a computer cluster dedicated to perform periodic BLAST searches and the manner in which the output of these searches is integrated into a laboratory database, SmedDb, are described herein. It is understood, however, that the methods and systems can be used for the management of any type of database comparison or updating, and the searching example and SmedDb example, are merely exemplary.

1. Computer Clusters

Figure 13:
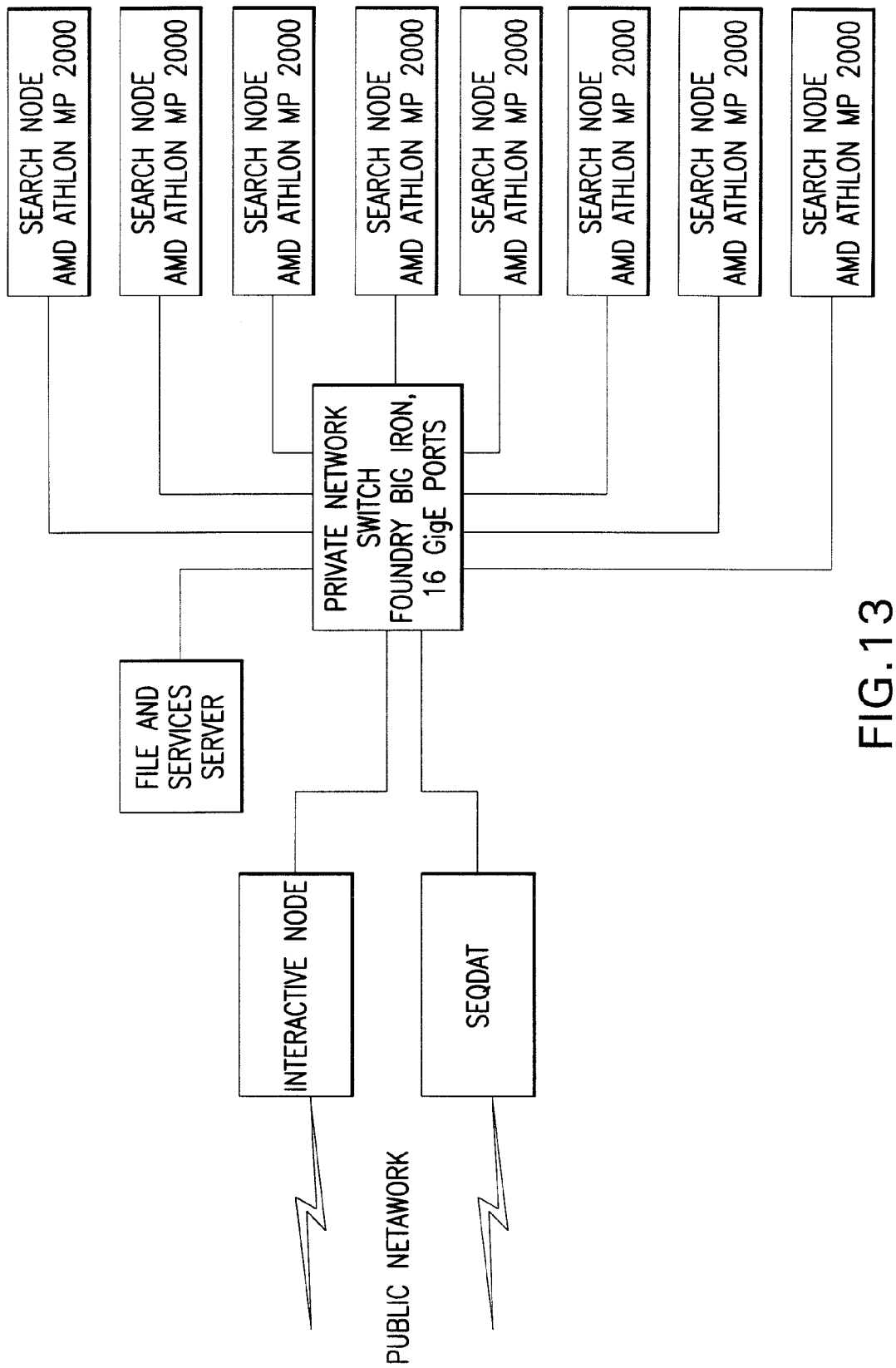

As used herein, a computer cluster is a set of at least two computers that are networked together, and which can share computing resources. One exemplary cluster is shown in FIG. 13. Thus, the a cluster is a connection of computers, or nodes, that can be managed in a coordinated fashion. The disclosed clusters comprise nodes. These nodes are separate pieces of hardware that can be configured or controlled to perform one or more tasks, or used to store, for example, one or more pieces or sets of information. For example, typically, the clusters disclosed herein will comprise a network switch node, which is capable of directing the movement of information between the computers in the cluster as well as information from outside the cluster. For example, the cluster can have functional nodes that perform a particular function, such as searching, for example, BLAST searching. Other DNA or protein homology search algorithms could be incorporated that take advantage of the processing power of computer clusters such as Entrez Structure databases, and 3D domains. The cluster can also have storage nodes that are repositories of specific sets of information, such as one or more databases. A given cluster can have as many nodes as desired, and furthermore, as the computing demands in a particular environment change, nodes can be added to handle, for example, the increased demand, or to add new and different functionalities. The clusters are designed to facilitate the exchange of information between the storage nodes and the functional nodes, and between different storage nodes, so for example, the information on one storage node can be used to update the information on another storage node.

A key aspect of the disclosed clusters is that they are expandable. Thus, the cluster can contain, for example, one target database node and one mirrored database node, such as one SmedDb node and one Genbank node, as disclosed herein. The cluster, however, could also contain any combination of nodes desired. For example, the cluster could comprise 3 different target nodes, such as a first, second, and third target node, and 5 other nodes, including a Genbank node, a Pubmed node, a Yeast genome node, a Human genome node, and a Human Map node. The number of database nodes, both target and mirrored as well as other types of stand alone or internet accessible database nodes are unlimited.

Thus, the disclosed computer clusters comprise at least two nodes that contain some type of database. The clusters also typically comprise at least one network switch node, but can have multiple switch nodes, such as 2, 3, 4, 5, 6, 7, 8, 9, 10, or more switch nodes. The network switch node can have a number of different functions. For example, the network switch node functions to direct the flow of information between the database nodes and the functional nodes. Furthermore, the network switch functions to monitor the activity on the functional nodes so as to maximize the efficiency of the cluster node resources. These functions can be controlled using any script achieving these functions. An example of scripts is found in FIGS. 14 and 15.

On certain embodiments the disclosed clusters can allow for the simultaneous updating of one or more databases on the database nodes and the comparison or other functional performance of the information on the database nodes in the cluster against each other. For example, if one database node contains the Genbank database and another of the database nodes is a target database node, such as the SmedDb, the disclosed clusters can continually update the Genbank database, which is constantly changing, and at the same time, compare the sequences in the SmedDb to the Genbank sequences on one or more of the functional nodes.

a) Storage Nodes

Typically a cluster as described herein will have at least one storage node, such as a database node. A database node is a node that houses in its memory one or more databases. While there can be any type of database, and thus database node, two types of databases are query databases and target databases which can reside on query database nodes and target database nodes. Typically the database node will house only a single database, but more than one database could be housed on a single database node. It is understood, however, that when more than one database are housed on a given node, the performance of the node, relative to just one of the databases being housed on the node will typically decrease. When there is only a single database on a node, performance will typically increase, all other parameters being the same. The database node can be a stand alone database, meaning that its main storage and handling occur on the node, or it can be a database that is derived or maintained from outside the computer cluster, i.e. a remote site. For example, the database can be a mirrored database, from a site extra to the computer cluster. Examples of these types of database would be any database, for example, at the National Center for Biotechnology Information (NCBI) (described herein), such as the GenBank DNA sequence database.

(1) Query Databases and Query Database Nodes

A query database is any database that contains information that can be used to update a module in another database, such as a target database. Often the query database is a database that is updated routinely, such as daily. When a database is a database that is obtained, for example, by mirroring another database, or obtaining information from a database accessible on the Web or outside the computer cluster, the database can be continually updated, while residing on its node. This is beneficial, as many of the databases that might reside outside the node originally, are changing constantly. A query database can be this type of databse.

A node that comprises a query database can be referred to as a query node. The disclosed computer clusters, allow for this updating of the databases to be performed continuously, or semi-continuously on in an automated way and furthermore, these operations can be performed in a way that allows them to be performed in the background of the cluster activity, for example, when the node is not being queried for a search, such as by the network switch. Furthermore, in certain embodiments, a database that is continually being updated, can maintain multiple generations of itself on the node that the main database resides on, or each generation could be stored on a different node if desired. For example, a node dedicated to a database that is continually being updated, such as a node dedicated to Genbank, could retain three generations of the Genbank database on it at any given time. These generations could be cataloged based on their date of creation, and the oldest generation could be removed from the node at the completion of a new generation caused by the updating of the database on a new day. Having multiple generations of the database on the node or nodes can be helpful in allowing updating or creation of the latest generation to occur simultaneously to the use of a previous generation in some type of activity, for example, performed on a functional node, such as searching.

One type of query database could be a database obtained from the NCBI discussed below.

(a) NCBI Databases

NCBI databases include the Protein Sequence database, the Nucleotide sequence database, Genbank, Genomes, Structure, Taxonomy, Population Study data sets, the Online Mendelian inheritance in Man (OMIM), ProbeSet, 3D domains, CDD, and Unigene.

The Protein sequence database, which contains as protein sequence entries compiled from a variety of sources including Swiss-Prot, PIR, PRF, PDB, and translations from annotated coding regions in GenBank and RefSeq. The Nucleotide sequence database contains nucleotide sequences from several sources, including GenBank, RefSeq, and PDB. Genbank is a collection of nucleic acid and protein sequences collected from individual submissions, as well as constant updating and data exchange with other main sequence databases, such as the European Molecular Biology Laboratory (EMBL) database and the DNA Database of Japan (DDBJ). Genbank also is in a data exchange with the United States Patent and Trademark Office for sequences submitted in published patent applications and issued patents. The Genomes database contains the partial or complete, when available, genomes of over 800 organisms and is continually updated. The Structure database contains the Molecular Modeling Database, which contains. 3-dimensional macromolecular structures, including proteins and polynucleotides. The Taxonomy database contains the names of all organisms that are represented in the genetic databases with at least one nucleotide or protein sequence. The Population study data sets database contains a collection of DNA sequences that have been collected to analyze the evolutionary relatedness of a population. The Online Mendelian Inheritance in Man (OMIM) contains a collection of human genes and genetic disorders authored and edited by Dr. Victor A. McKusick and colleagues. The ProbeSet database contains NCBI's gene expression and hybridization array repository (GEO) data. The 3D Domains database contains protein domains from the Entrez (NCBI) Structure database.

The CDD database stands for the Conserved Domain Database, a collection of sequence alignments and profiles representing protein domains conserved in molecular evolution.

There are a variety of nucleotide and protein databases at the NCBI, such as Genbank, the EST database, the GSS database, Homologene database, HTG database, SNP database, RefSeq database, and STS database, UniSTS and UniGene.

The EST database contains expressed sequence tags, or short, single-pass sequence reads from mRNA (cDNA). The GSS database contains genome survey sequences, or short, single-pass genomic sequences. The HomoloGene database compares nucleotide sequences between pairs of organisms in order to identify putative orthologs. The HTG database is a set of high-throughput genome sequences from large-scale genome sequencing centers, including unfinished and finished sequences. The SNP database contains both single nucleotide substitutions and short deletion and insertion polymorphisms. The RefSeq database is a database of non-redundant reference sequences standards, including genomic DNA contigs, mRNAs, and proteins for known genes. Multiple collaborations, both within NCBI and with external groups, support our data-gathering efforts. The STS database contains sequence tagged sites, or short sequences that are operationally unique in the genome. The UniSTS database contains a unified, non-redundant view of sequence tagged sites (STSs). The UniGene contains a collection of ESTs and full-length mRNA sequences organized into clusters, each representing a unique known or putative human gene annotated with mapping and expression information and cross-references to other sources.

There are a number of databases at the NCBI related to genomes of organisms, including the Bacteria, Eukaryotic Organelles, Fruit Fly, Human, Malaria, Mouse, Nematode, Plant Genomes, Plasmids, Rat, Retrovirus, Viroids, Yeast, and Zebrafish. The NCBI provides access to the whole genomes of over 1,000 organisms, both partial and complete The Bacteria database contains graphical representations of complete bacterial genomes, which can be viewed in their entirety or explored in progressively greater detail, with links to associated sequence data. The Eukaryotic Organelles database contains information about eukaryotic organelles, a description of organelle reference sequences, and links to a list of completely sequenced organelles shown in taxonomic hierarchy and alphabetically by organisms. The Fruit fly database contains resources for the fruit fly, and graphically displays all of the chromosomes of the fruit fly and allows you to search both cytogenetic and sequence data across the whole genome. The Human database contains human genome data resources, including bulletins and progress reports on the Human Genome Project. The Malaria database contains malaria genetics and genomic information and data. The Mouse database is a set of mouse-related resources from multiple centers including, sequence, mapping, and clone information as well as pointers to strain and mutant resources. The Nematode database contains the *C. elegans* sequence data. The Plant Genomes database contains graphics of plant chromosomes from many different plants which can be viewed in their entirety or explored in progressively greater detail, with links to associated sequence data. The Plasmid database contains graphics of complete plasmids with links to associated sequence data. The Rat database contains rat-related resources from multiple centers, including sequence, mapping, and clone information as well as pointers to strain and mutant resources. The Retroviruses database contains a set of resources specifically designed to support research efforts. The Viroids database contains graphics of complete viroid genomes with links to associated sequence data. The Yeast database contains graphical representations of chromosomes that can be viewed in their entirety or explored in progressively greater detail, with links to associated sequence data. The Zebrafish database contains zebrafish-related resources from multiple centers, including sequence, mapping, and clone information as well as pointers to strain and mutant resources.

The NCBI also contains a number of databases containing maps of organisms such as, Map Viewer, Arabidopsis Map, Fruit Fly Map, GeneMap '99, Human Map, Human-Mouse Homology Maps, Malaria Map, Model Maker, Mosquito Map, Mouse Map, Nematode Map, OMIM Gene Map, OMIM Morbid Map, Rat Map, and the Zebrafish Map.

The NCBI database also includes a number of databases related to cancer, such as Spectral Karyotyping (SKY) and Comparative Genomic Hybridization (CGH) Database, Cancer Chromosome Aberration Project (CCAP), Cancer Genome Anatomy Project (CGAP), Mitelman Database of Chromosome Aberrations in Cancer, SAGE Analysis, SAGEmap:

The SKY and CGH Database contains publicly submitted SKY and CGH data. The CCAP database contains the definition and detailed characterization of the distinct chromosomal alterations that are associated with malignant transformation. The CGAP database contains identified human genes in different cancerous states. The Mitelman Database of Chromosome Aberrations in Cancer contains a genome-wide map of chromosomal breakpoints in human cancer, by Drs. Mitelman, Mertens, and Johansson. SAGE stands for Serial Analysis of Gene Expression. The SAGE Analysis databse contains differential expression of SAGE tags in cancer libraries. (See SAGEmap). The SAGEmap Web site contains a differential analysis of CGAP SAGE libraries, and includes a comprehensive analysis of SAGE tags in human GenBank records, in which a UniGene identifier is assigned to each human sequence that contains a SAGE tag.

Other NCBI databases include the Molecular Modeling Database (MMDB) of 3D protein structures, the Unique Human Gene Sequence Collection (UniGene), a Gene Map of the Human Genome, the Taxonomy Browser, and the Cancer Genome Anatomy Project (CGAP), in collaboration with the National Cancer Institute.

The NCBI has a number of literature related databases including PubMed which links citations in MEDLINE, and additional life sciences journals, including abstracts and links to full articles where available on line. The literature databases currently at NCBI are PubMed Central, Journals, Bookshelf, and PROW.

PubMed Central is a digital archive of life sciences journal literature, developed and managed by NCBI. The Journals database allows searching for a journal and then link to records for that journal in the database. Bookshelf (Books) is a database of adapted textbooks and monographs which are web-linked with other resources, such as Genbank, OMIM, and LocusLink. The goal of Bookshelf (Books) is to become completely integrated with the other databases provided by the NCBI. PROW stands for Protein Reviews On the Web and is an online resource that features PROW Guides—authoritative short, structured reviews on proteins and protein families. The Guides provide approximately 20 standardized categories of information for each protein.

The NCBI also provides a variety of software tools that can be downloaded and used, for example, on the disclosed nodes of the computer clusters. For example, BLAST is a program for sequence similarity searching developed at NCBI, and is used for identifying genetic features, similarities, functional domains, and other types of comparisons between nucleic acid or protein sequences. BLAST currently can execute sequence searches against the entire DNA database in Genbank in less than 15 seconds. Additional software tools provided by NCBI include: Open Reading Frame Finder (ORF Finder), Electronic PCR, and the sequence submission tools, Sequin and BankIt.

Many of the databases and tools from NCBI can be downloaded via FTP or other protocols. For example, some databases that can be downloaded include GenBank as the most recent fall release and/or daily cumulative or non-cumulative update files in flat file format, ASN.1 format, or FASTA format. RefSeq and LocusLink can also be downloaded. LocusLink provides a single-query interface to curated sequence and descriptive information about genetic loci by searching a browsable list that includes items such as gene names, descriptive terms, and LocusID numbers. dbSNP a database containing single nucleotide polymorphisms, small-scale insertions/deletions, polymorphic repetitive elements, and microsatellite variation can also be downloaded, as well as Human Genome Project Data, which contains one folder for each chromosome, which includes genomic contigs built from finished and unfinished sequence data. The contigs are available in various formats, including ASN.1 format, FASTA format, GenBank flat file format, and GenBank summary format. Other Genomes database can also be downloaded which includes genomes including bacteria, nematode, mouse, and others, can be downloaded from one of two directories: ftp://ftp.ncbi.nih.gov/genomes/ or ftp://ftp.ncbi.nih.gov/genbank/genomes/. Data from the Map Viewer can be downloaded. The Repository of Databases including Uni-Gene, GeneMap, dbEST, dbGSS, dbSTS, can be downloaded. Furthermore, OMIM, and a number of externally curated and maintained specialized databases can be downloaded. The Taxonomy database can also be downloaded.

A variety of software can be downloaded including BLAST, Cn3D which is a stand-alone software for viewing structures in three dimensions, Client/Server Programs, including Sequin for submission of one or many submissions, long sequences, complete genomes, alignments, population/phylogenetic/mutation studies and Network Entrez, which is a TCP/IP-based client server version of WWW Entrez and makes a direct connection with the NCBI databases over the Internet to retrieve data. Client software is available for PC, Mac, and Unix. Network-Client BLAST (blastc13) which can accesses the NCBI BLAST search engine. Blastc13 can search all the sequences in a FASTA file and produce one-to-many alignments in text or HTML format. It can also perform searches against multiple databases. The NCBI Software ToolBox, which is a set of software and data exchange specifications used by NCBI to produce portable, modular software for molecular biology can also be downloaded.

One of skill in the art understands how to use the NCBI databases, including those not listed here, and furthermore knows what these programs are and where and how to obtain them. Furthermore, one of skill understands the function that the programs perform, and that other programs can perform the same function, and these other programs are considered disclosed herein. Thus, programs and databases having the function of any of the NCBI databases and programs identified in herein are also disclosed, as well as the function of these programs and databases understood in the art is disclosed.

(b) Other Examples of Query Databases

One type of database that can be a query database and added to the disclosed clusters is the ProDom database. ProDom is a comprehensive set of protein domain families automatically generated from the SWISS-PROT and TrEMBL sequence databases (http://prodes.toulouse.inra.fr/prodom/current/html/home.php).

Another type of database is the Prosite database. Prosite is a database of protein families and domains. It consists of biologically significant sites, patterns and profiles that help to reliably identify to which known protein family (if any) a new sequence belongs (http://us.expasy.org/prosite/).

Another type of database is the DNA binding site matrices database. The DNA binding site matrices database is a collection of known consensus sequences for DNA binding proteins (TRANSFAC: http://www.cbil.upenn.edu/tess/) and (JASPAR: http://forkhead.cgb.ki.se/JASPAR/).

One of skill in the art understands how to use the databases, including those not listed here, and furthermore knows what these programs and databases are and where and how to obtain them. Furthermore, one of skill understands the function that the programs perform, and that other programs can perform the same function, and these other programs are considered disclosed herein. Thus, programs and databases having the function of any of the NCBI databases and programs identified in herein are also disclosed, as well as the function of these programs and databases understood in the art is disclosed.

(2) Target Databases and Target Nodes

Another type of database that the computer cluster can comprise on a node is a database that can be referred to as a target database. The target database is a database in which the manager of the computer cluster is interested in maintaining and updating with information from any other source. Typically the target database can be considered a stand-alone database in that it can be unique to the computer cluster that it resides on. A node comprising a target database can be referred to as a target database node. An example of a target database as used herein is the SmedDb as disclosed herein. The SmedDb contains a set of ESTs and cDNAs related to the *Schmidtea mediterranea* organism, along with other unique collected information from a variety of sources, such as Genbank. Thus, for example, the target database can contain sequence information from an organism which is in the process of being sequenced, i.e. the database is continually being changed, with new records being added each day. Another attribute of the target database can be that it contains additional information other than just sequence information, such as in situ hybridization data, or functional data, or mRNA expression data, or structure information. Thus, a target database can be a database that represents a collection of many different types of information, all associated with a unique identifier, and all of which can be or can desired to be updated. This type of other information can often be collected or mined from other sources found on the Web or from other computer clusters. Furthermore, the target database typically can be displayed in a way that allows one to see all of the collected information for a Particular record, such as the base EST or cDNA.

(a) Modules

As described above, the system can contain individual modules containing discreet bundles of information, which can be associated with a unique identifier and displayed in an executive summary. What is meant by "module" is a component of information containing a discrete set of parameters. For example, one module can contain the biologically significant information, such as the original sequence information in FASTA format, such as for cDNAs and ESTs. Another module can contain hybridization informatinh, such as in situ hybridization, two hyrid information. Yet another module can contain sequence comparison information found in the BLAST search and derived from the second database. The module can contain information from publicly accessible databases such as those listed above. Other modules can contain immunohistological information, pharmacology data, gene expression patterns, for example. A module can contain any information to be associated with a given record.

For example, one module can contain the biologically significant information, such as the original sequence information in FASTA format, such as for cDNAs and ESTs. Another module can contain hybridization information, such as in situ hybridization, two hyrid information. Yet another module can contain sequence comparison information found in the BLAST search and derived from the second database. The module can contain information from publicly accessible databases such as those listed above. Other modules can contain immunohistological information, pharmacology data, gene expression patterns, for example. A module can contain any information to be associated with a given record. The SmedDb exemplifies the use of modules. It is understood that any type of information that can be associated with the record can be considered a module, and be associated with the record. This module can then be utilized as any other module disclosed herein.

(b) SmedDb

SmedDb is an example of a type of target database. It is understood that the general characteristics, however, of the SmedDb, that are discussed herein, for example, the modules that make up SmedDb, can be applied to any genomic database that is based on sequence ESTs or cDNAs or protein sequence, for example. Here the following describes features of SmedDb, a DNA sequence and gene expression pattern database for the planarian *Schmidtea mediterranea* designed to serve the bioinformatic needs of the growing communities of planarian biologists in particular, and regeneration researchers in general.

The SmedDb is a database that comprises a number of modules, where each module is a unique type of information, such as sequence information or functional information or structural information. These modules are linked together through association with a common identifier. In one aspect, each module can be updated through activity on the disclosed clusters and the contents of each module for each identifier can be displayed or outputted in an executive summary.

(i) Sequence Module—SmedDb EST Information

The freshwater planarian *Schmidtea mediterranea* (A. Sanchez Alvarado, et al., "The *Schmidtea mediterranea* database as a molecular resource for studying platyhelminthes, stem cells and regeneration," *Development*, vol. 129, pp. 5659-65, 2002) has been studied in order to identify genes that are active during a variety of biological processes such as tissue regeneration and stem cell biology. A total over of 6,600 unique gene sequences of expressed genes, also known as expressed sequence tags (ESTs), have been accumulated. ESTs are key reagents for printing DNA microarrays, carrying out large-scale spatial expression pattern studies, and the functional characterization of proteins. The utility of an EST collection depends in great part on determining if the obtained sequence has been identified in other organisms, as these types of comparisons allow for the refinement of functional characterization and experimental design. However, comparing over 6,500 ESTs to the NCBI databases on an individual basis would take hours if not days of supervised activity, not only during the performance of the BLAST searches themselves, but also in the archiving of the results of the searches into a laboratory database known as the *Schmidtea mediterranea* Database (SmedDb) (A. Sanchez Alvarado, et al., "The *Schmidtea mediterranea* database as a molecular resource for studying platyhelminthes, stem cells and regeneration," *Development*, vol. 129, pp. 5659-65, 2002).

In order to overcome the difficulties described above, the SmedDb used for the storage and organization of sequences and their BLAST results has been integrated with a low cost commodity based cluster computer system that can semi-automatically process thousands of BLAST searches when the NCBI databases change. The end result for the investigator is a dynamic database that is regularly and automatically updated to obtain the most up-to-date sequence comparisons available.

The SmedDb comprises nearly 3,000 non-redundant cDNA sequences from the freshwater, diploid planarian *Schmidtea mediterranea*, as well as the application of automated whole-mount in situ hybridizations to study gene expression patterns has served as a platform for the development of a relational database for this organism. The *Schmidtea mediterranea* Database (SmedDb) is a web-accessible repository of cDNA sequences, gene expression patterns, immunohistological reagents and bioinformatic tools all of which are integrated to aid in the molecular study of tissues undergoing temporal transformation and promote interphyletic molecular comparisons of biological events.

Figure 2:
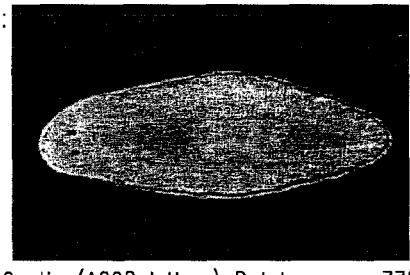

A large number of randomly selected cDNAs from clone CIW4 of *Schmidtea mediterranea* is contained in SmedDb. The complexity of the libraries utilized to carry out the EST project is shown in FIG. 1. Approximately 68% of all clones sequenced (2021) had a frequency distribution equal to 1. If the distribution of all sequenced clones is assumed to follow a Poisson function, nearly 73% of all unique cDNAs were recovered and represented in the library (FIG. 1). After sequencing, each non-redundant EST deposited in the database becomes an individual record. The record consists of the EST identification name (EST ID), GenBank accession number, cDNA sequence, functional category and subcategory, in situ data (if available), and GenBank BLAST results (Altschul, S., et al., (1990), *J. Mol. Biol.* 3, 403-410) containing links to Entrez-PubMed (FIG. 2). The description of the *S. mediterranea* cDNA sequence is determined by the expectancy value of the obtained GenBank return. Records retrieving significant matches from GenBank (E value $\leq -4$) are appended with the top scoring gene description. Low scoring hits (E value $\geq -4$) are tagged as "No Significant Match" and a sequence without a homologue or "hit" is noted as "No Match". Reciprocally, access to SmedDb from GenBank is facilitated by hyperlinks to SmedDb found in every *Schmidtea mediterranea* GenBank entry.

(ii) Immunohistology Marker Module

Immunohistological data can also be associated with a module. For example, regarding the SmedDb database, two lists of antibodies comprising nearly 140 different polyclonal and monoclonal antibodies that have been tested for cross-reactivity with planarian tissues (Robb S M C, Sánchez Alvarado A. 2002, Genesis 32:293-298) can be found in SmedDb. Information on the source, dilution and type of secondary antibodies utilized is also provided. Confocal images of the immunohistological patterns obtained with cross-reacting antibodies can also be found in the database and new entries are added to the list as more antibodies are tested and characterized. This should provide a reagent and pictorial reference of suitable antibody markers to the research community working on flatworms for the purpose of characterizing, for example, RNAi-induced phenotypes. As more markers are identified and published, it is expected that this list will expand by including contributions from other planarian laboratories.

(iii) Function Module

The descriptions assigned to each sequence by the above-described procedure serves to place each sequence into putative functional categories (FIG. 3). The nomenclature for such categories were derived from the expressed gene anatomy database (EGAD; http://www.tigr.org) and the gene ontology (http://www.geneontology.org) functional classification systems. For example, there can be twelve functional categories, each of which is composed of specific subcategories for a total of forty six subcategories (FIG. 3, Example 1). Examples of functional categories are "Cell defense", "Cell-cell communication", "General metabolism", genes of unknown function with homologues in the extant databases ("Unknown Function") and genes with no known homologues ("No Match"). Approximately 69% of the ESTs share significant similarities with sequences present in GenBank and therefore belong to categories other than "no match". For instance, there are at present 56 ESTs defined as being similar to cell cycle/cell division genes, 44 putatively involved in RNA processing, and 77 cDNAs with high homology to transcription factors.

Figure 4:
Figure 6:
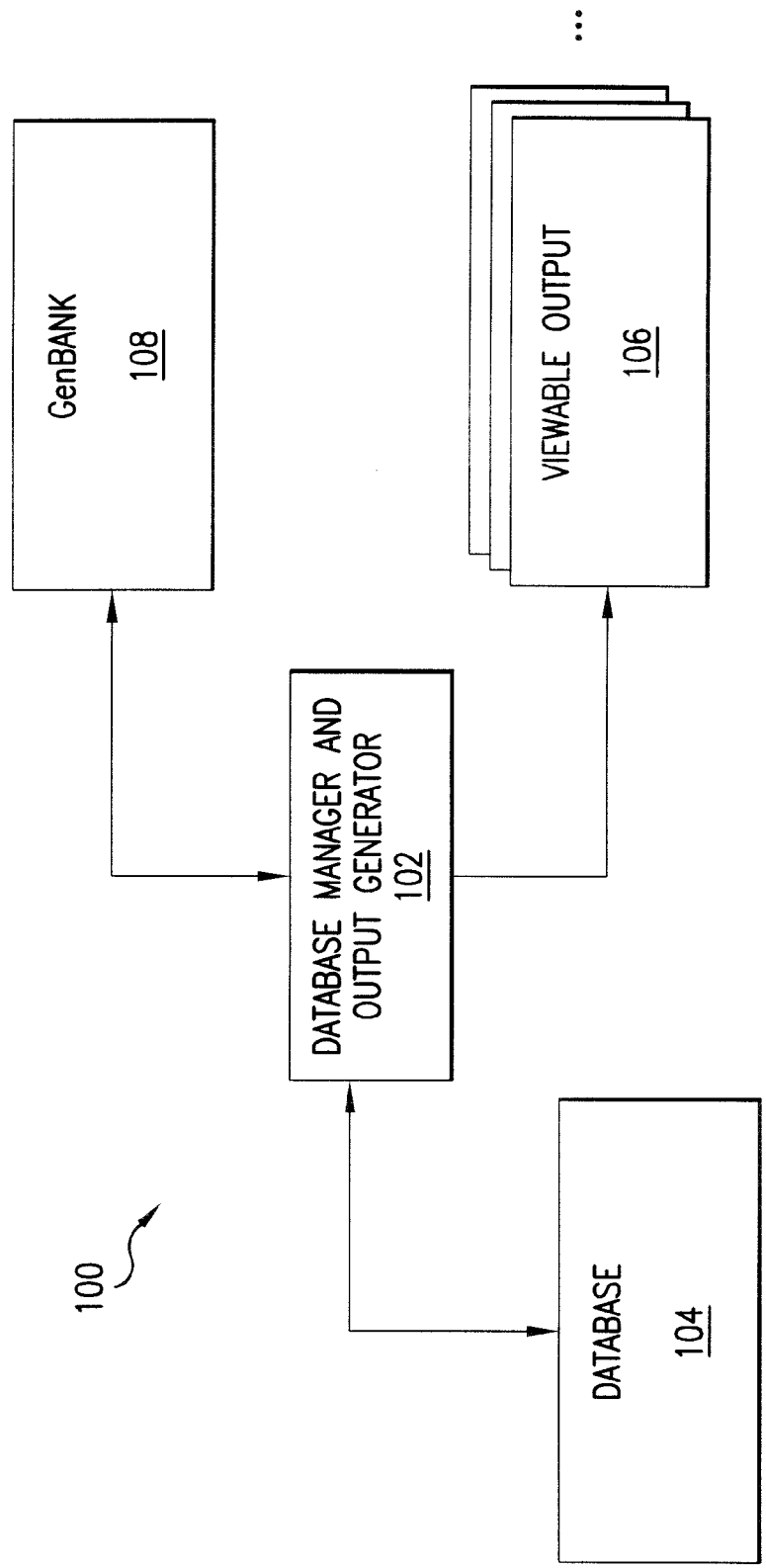
Figure 7:
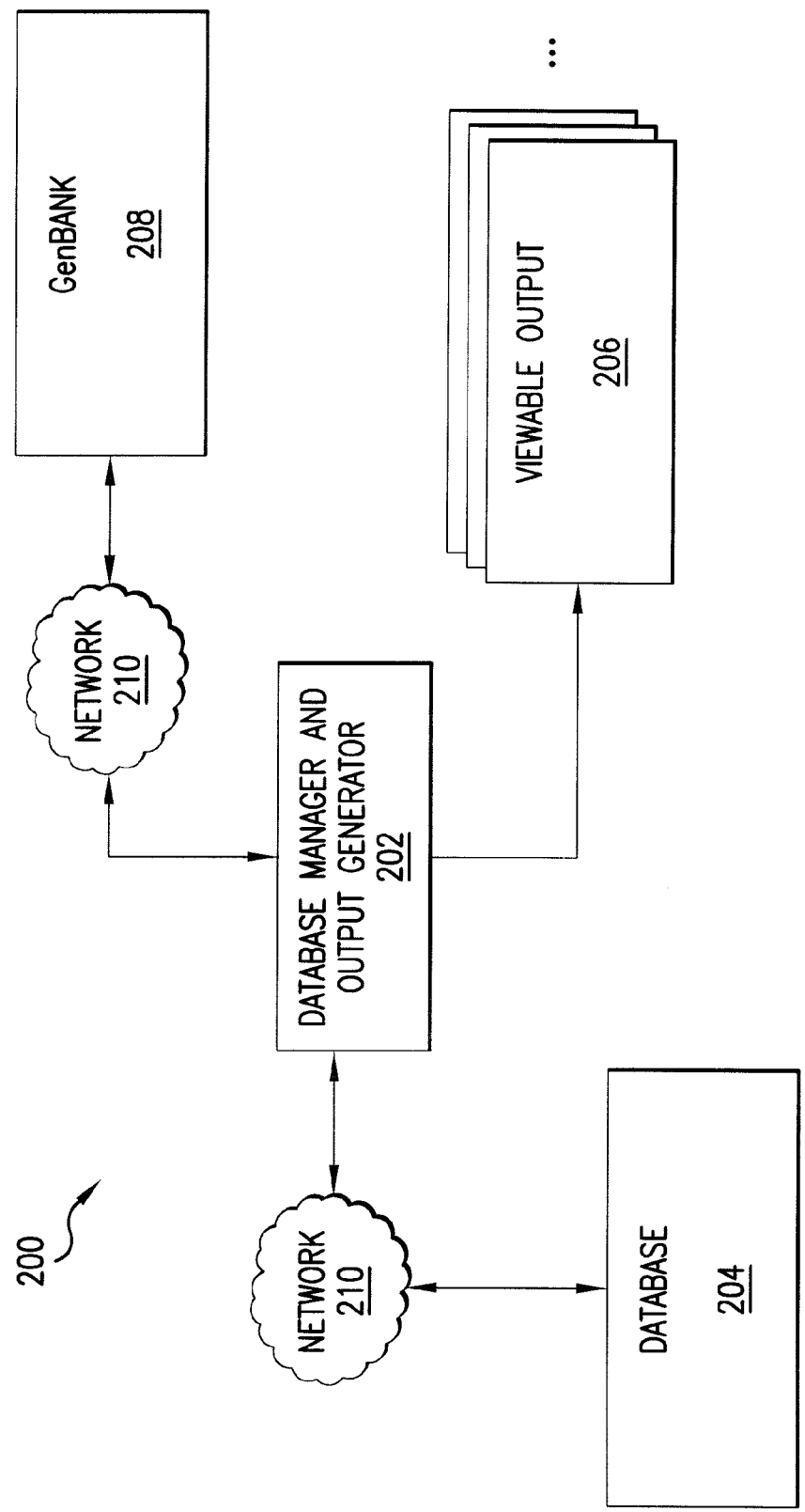
Figure 8:
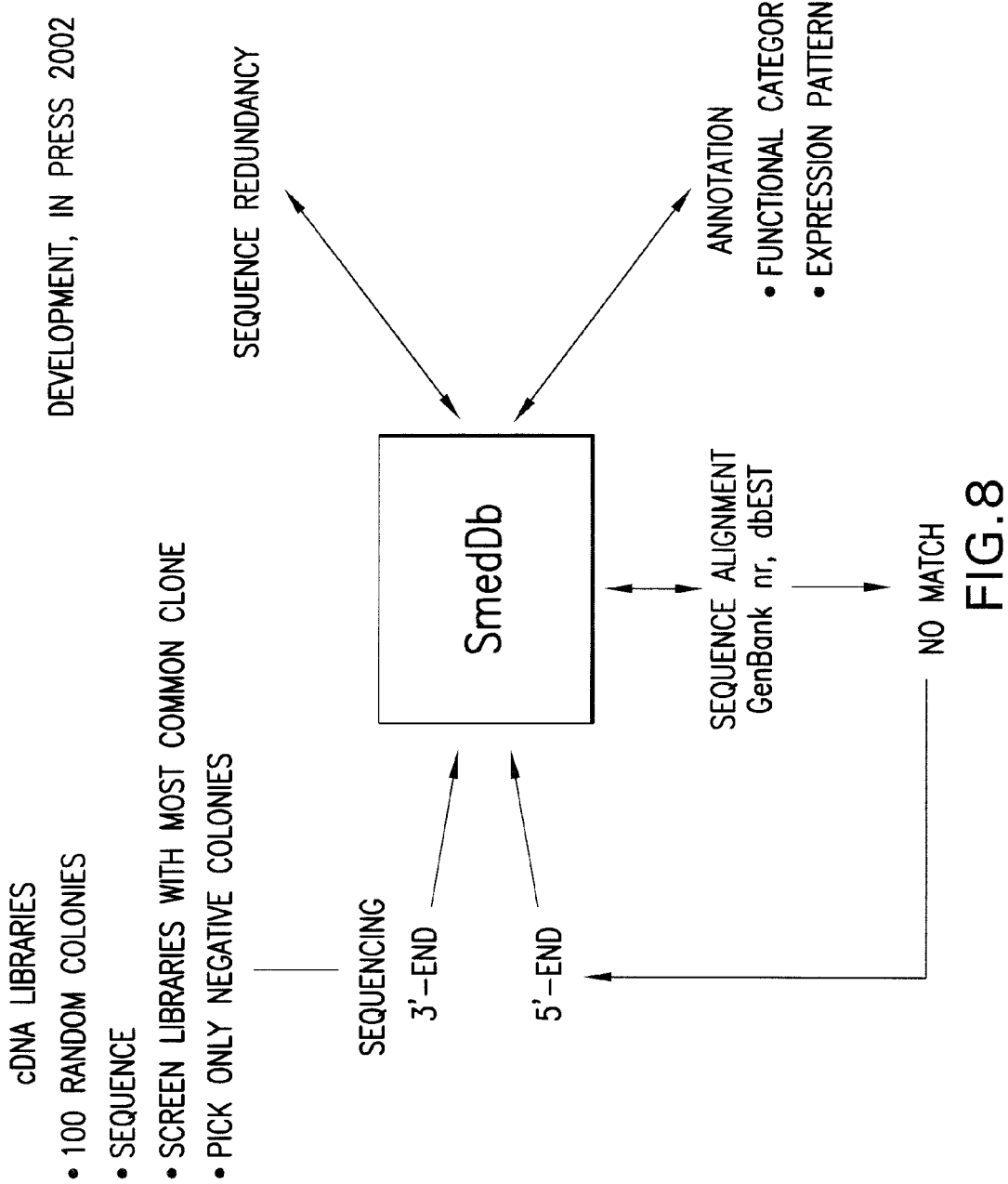
Figure 9:
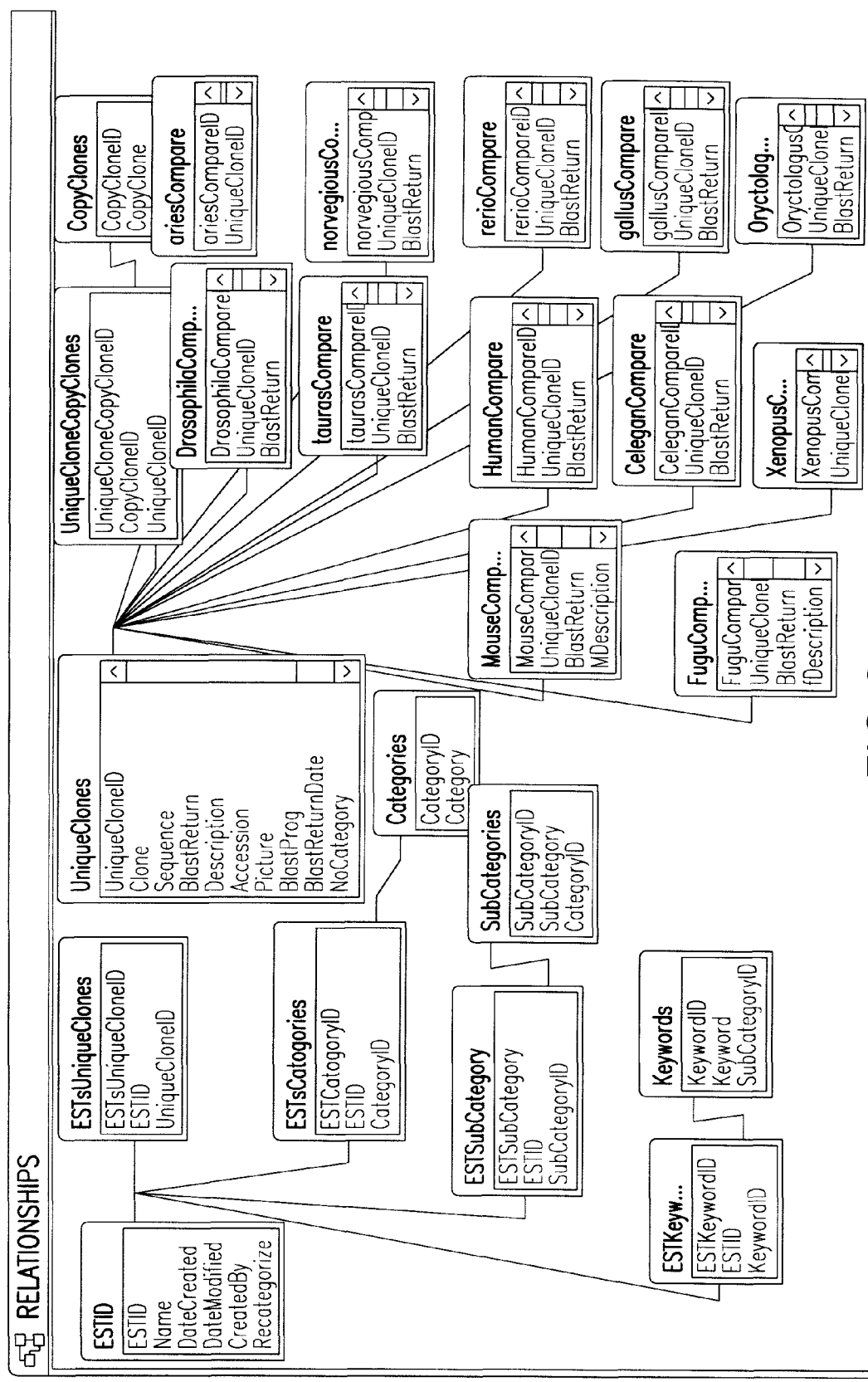
Figure 10B:
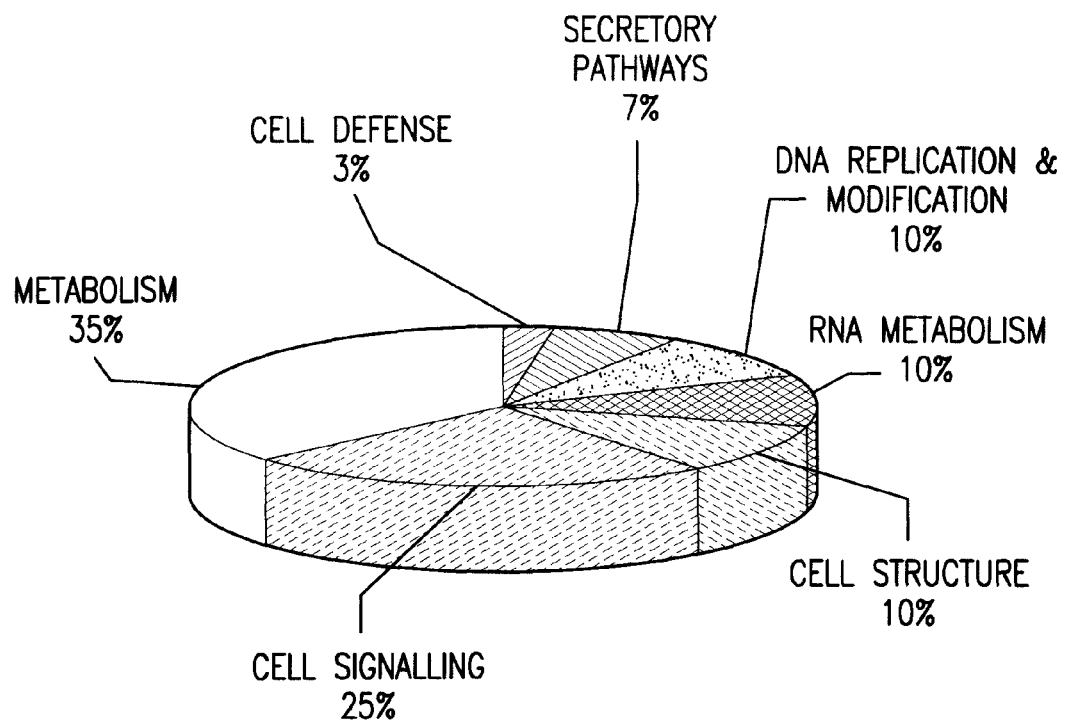
Figure 10C:
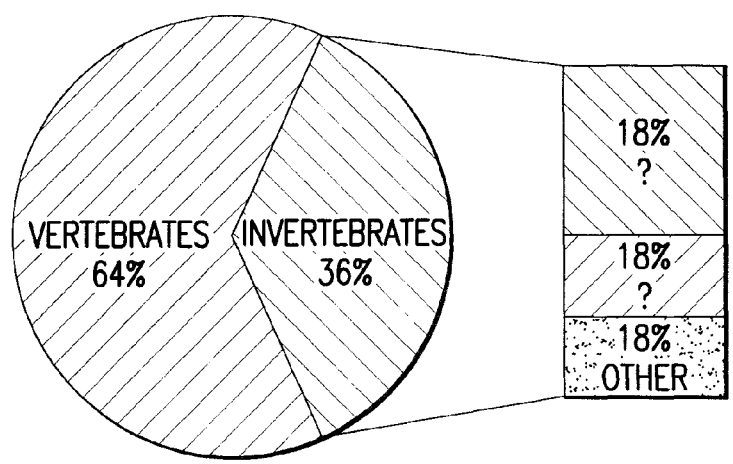

The database can be searched by accession number, category and subcategory, or by carrying out direct sequence comparisons of sequences of interest against the first database using a stand-alone BLAST application, for example. The database can then be searched by any of the following methods (these methods are intended to be examples and are in no way limiting):

Accession Number. If the accession number is known it can be used to find the corresponding record by typing it into the text box found at the top of the search page (FIG. 3). Once the "search by Accession Number" button has been selected, an executive summary of the record will be displayed. Included in this output are the EST ID, accession number, description, category, subcategory, a link to the entire record ("More Info"), and a link to the in situ data if it is available (FIG. 4). Categories. If an accession number is not known and one wishes to review specific types of genes, the database can be searched by functional categories on the same "search" page (FIG. 3). When using this search tactic, different combinations of categories and subcategories can be selected. In order to avoid redundancy of search results by using this method, each record is present only in one subcategory, which in turn is unique to a given functional category. When one category check box is selected all records, belonging to this category, will be displayed. If only one subcategory is selected only the records belonging to that subcategory will be presented. Since category selection supersedes subcategory selections, an uninformative combination of choices would be, for example, the selection of a category and one of its subcategories. The resulting output would include all records belonging to the chosen functional category. However, if two subcategories from two different categories are selected, only the records belonging to the chosen subcategories will be returned. To narrow or broaden the results of any of the category/subcategory searches, the "refine search" button (found at the bottom of the results page) can be used. This action will return the browser to the previous search page with all former search guidelines intact. The prior search can now be appropriately altered.

A search interface can also be provided which is accessible by a web browser as well understood in the art.

(c) Executive Summaries

The various modules can be viewed in an executive summary. An "executive summary" is a summary of all the information associated with a record (unique identification record.) An example of an executive summary can be found in FIG. 4. The executive summary displays the information found in the individual modules associated with the given record. The biologically significant information can be sorted by any of the characteristics associated with the modules and displayed in the executive summary.

b) Functional Nodes

As discussed herein, the clusters can comprise functional nodes. A functional node can be a stand alone computer which is designed to perform a particular function, such as sequence comparison, using for example, BLAST. A general function that a functional node can perform is the collection of information from one database, such as a query database, and then comparing that to the existing information in a module in a target database, and then updating the target database as needed.

(1) Exemplary Functions that can be Performed on the Functional Nodes (a) BLAST

The tools used to find sequence similarities between a researcher's protein or DNA sequence and the entries in the GenBank are the suite of BLAST—Basic Local Alignment Search Tool—programs (blastx, blastn, blastp, tblastx) (S. F. Altschul, et al., "Gapped BLAST and PSI-BLAST: a new generation of protein database search programs," *Nucleic Acids Res*, vol. 25, pp. 3389-402, 1997) available from the National Center for Biotechnology Information (NCBI) of the National Library of Medicine of the National Institutes of Health, but the disclosed methods can be used with any sequence comparison program. These programs are described in detail on the NCBI's main BLAST web site (http://www.ncbi.nlm.nih.gov/BLAST). The NCBI also maintains a number of databases available for download that are derived from the sequences deposited in GenBank. The NCBI site offers several search methods (webblast, networkblast and blast URL API) that are sufficient for the needs of many laboratories working on a relatively small number of genes. NCBI also offers the tools necessary for individuals and institutions to maintain their own web site with local copies of the various NCBI databases; this can be used in order to relieve part of the high demand on the NCBI maintained web site. Disclosed herein is a system set up on the High Performance Computing (CHPC) at the University of Utah. However for laboratories in need of analyzing many, for example, thousands, of individual sequences on a regular basis, these tools are not sufficient. For these cases, the NCBI offers also the standalone BLAST executables necessary for any individual to establish an in-house system as described in herein this paper. Executables exist for a variety of platforms including Linux, AIX, Solaris, Windows, MACos, HPux, Irix, and Decosf. All the executables can be readily obtained at the NCBI ftp site: ftp://ftp.ncbi.nih.gov/blast/executables.

Figure 5A:
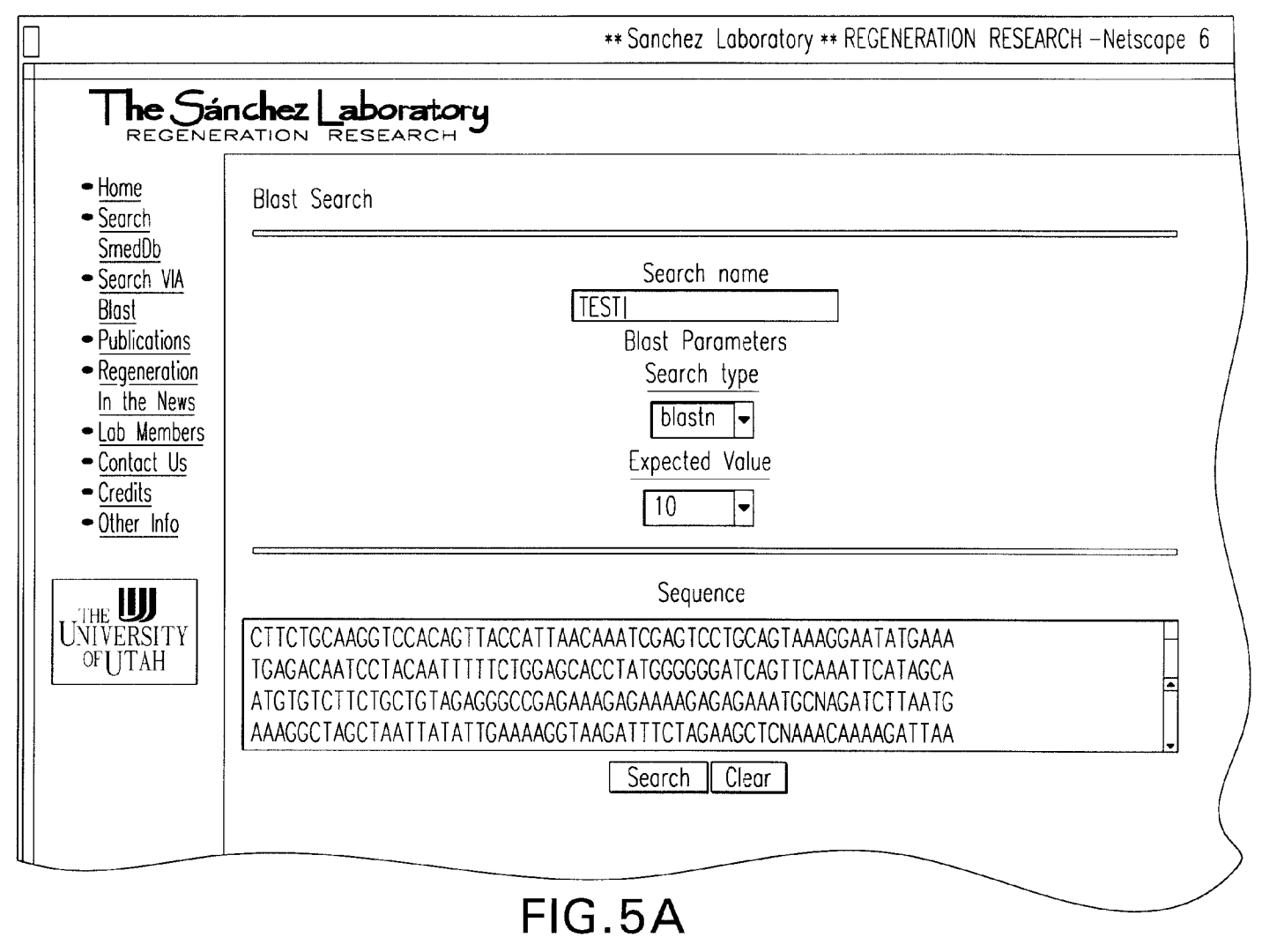

An example of how BLAST (Altschul, S., et al., (1990), *J. Mol. Biol.* 3, 403-410) can be used follows. The database can also be searched via a query sequence can be used to identify any similar planarian EST. A link, "Search via BLAST", located at the bottom of the "search" page and also on the side and top bars can be visited to utilize this search (FIG. 3). For output purpose, this search requires the typing of a search name into the first textbox (FIG. 5a). BLAST can support BLASTn for nucleotide comparisons and tBLASTn for comparing amino acid sequences, as well as any other types of sequence comparison information. If deemed necessary, the expected value can be altered from the default value of 10. The query sequence (nucleotides or single-letter amino acids) is then entered in the "Sequence" textbox (FIG. 5a). Once the search is complete a new window will appear with the results (FIG. 5b). EST IDs can be displayed in a list, and are hyperlinked to the corresponding EST record in the first database. This type of search is useful to determine which of the sequences match an investigator supplied query sequence (nucleotide or amino acid) and to view the corresponding spatial expression patterns of the planarian homologue.

(b) Display Functions

One type of general function that could be performed on a functional node would be the function of updating a three dimensional structure display for example for a particular sequence within a record. As three dimensional structure information becomes available it can be used to update the target database, for example. Exemplary types of programs that can be used to perform this function would be for example, CHIME. Chime can be obtained as a plugin at for example, http://mirrors.rcsb.org/SMS/STING-L/help/chime.html. Chime supports most of the popular structure display formats that scientists use including MDL Information Systems' Molfile and Rxnfile and many of the popular 3D display formats such as the Brookhaven Protein Databank (PDB) format (3D rendering and RasMol scripting code courtesy of Roger Sayle).

Other types of display can be models that for example, display graphically the domains of a given protein. For example, the database called Pfam contains a large collection of multiple sequence alignments and hidden Markov models covering many common protein families (http://pfam.wustl.edu/) and can produce domain structures of proteins as they are aligned in the protein. This database is continually updated, and a functional node can act to update, for example, a target database, with the information in, for example, a mirrored Pfam database, when the target database contains as one of its modules the domain structure of the record in the database.

(c) Motif Comparison

For analysis of genomic sequence to identify motifs that exist motif analysis can be performed on functional node. For example, the function can be performed by the program called Gibbs Motif Sampler. This program will allow the identification of motifs and conserved regions in DNA or protein sequences. This software was developed by Eric C. Rouchka and Bill Thompson based on work by C. E. Lawrence, J. S. Liu, A. F. Neuwald and others as part of the Bayesian Bioinformatics Program at the Biometrics Laboratory of Wadsworth Center. (Lawrence, C. E., et al., (1993), "Detecting Subtle Sequence Signals: A Gibbs Sampling Strategy for Multiple Alignment," Science, 262, 208-214; Lawrence, C. E., and Reilly, A. A. (1990), "An Expectation Maximization Algorithm for the Identification and Characterization of Common Sites in Unaligned Bipolymer Sequences," PROTEINS: Structure, Function, and Genetics, 7, 41-51; Liu, J. S., et al., (1995), "Bayesian Models for Multiple Local Sequence Alignment and Gibbs Sampling Strategies," Journal of the American Statistical Association, 90, 432, 1156-1170; Liu, J. S. and Lawrence, C. E. (1999), "Bayesian Inference on biopolymer models" Bioinformatics 15, 38-52; Martin, D. I. K and Orkin, S. H. (1990), "Transcriptional activation and DNA binding by the erythroid factor GF-1/NF-E1/Eryf1," Genes & Development, 4, 1886-1898; McCue, L. A., et al., (2001) "Phylogenetic footprinting of transcription factor binding sites in proteobacterial genomes" Nucleic Acids Res. 2001 29: 774-782; Neuwald, A. F., et al., (1995), "Gibbs Motif Sampling: Detection of bacterial outer membrane repeats," Protein Science, 4, 1618-1632; Omichiniski, J. G., et al., (1993) "NMR Structure of a Specific DNA Complex of Zn-Containing DNA Binding Domain of GATA-1," Science, 261, 438-446; Orkin, S. H. (1995), "Regulation of globin gene expression in erythroid cells," Eur. J. Biochem. 231, 271-281; Stormo, G. D., Hartzell, G. W. (1989) "Identifying protein-binding sites from unaligned DNA fragments," Proc. Natl. Acad. Sci. USA 86:1183-1187; Liu, J., Neuwald, A., Lawrence, C. E., (1999) Markovian Structures in Biological Sequence Alignments, J. Amer. Stat. Assoc., 94, 1-15; Wasserman, W., et al., (2000) Human-mouse genome comparisons to locate regulatory sites, Nature Genetics, 26, 225-228; Warner, B. L., (1996) Phosphorous Assimilation and Control of the Phosphate Regulon. In Neihdhardt, F. C. (ed.) *Escherichia coli* and *Salmonella*: Cellular and Molecular Biology. ASM Press, Washington, D.C., pp 1357-1381, and all of these references are incorporated by references herein at least for material related to motif and sequence comparison functions and programs).

(d) Other Functions

For example, other functions can be found in TmPred and SignalP. TmPred is Prediction of Transmembrane Regions and Orientation. The TMpred program makes a prediction of membrane-spanning regions and their orientation (www.ch.embnet.org/software/TMPRED_form.html). The SignalP program, The SignalP World Wide Web server, predicts the presence and location of signal peptide cleavage sites in amino acid sequences from different organisms: Gram-positive prokaryotes, Gram-negative prokaryotes, and eukaryotes. The method incorporates a prediction of cleavage sites and a signal peptide/non-signal peptide prediction based on a combination of several artificial neural networks (http://www.cbs.dtu.dk/services/SignalP/).

A non-limiting list of functional activities that can be acquired and performed on a functional node for viewing or otherwise manipulating structures include, but are not limited to; Midas (UCSF), MidasPlus (UCSF), MOIL (University of Illinois), Yummie (Yale University), Sybyl (Tripos, Inc.), Insight/Discover (Biosym Technologies), MacroModel (Columbia University), Quanta (Molecular Simulations, Inc.), Cerius (Molucular Simulations, Inc.), Alchemy (Tripos, Inc.), LabVision (Tripos, Inc.), Rasmol (Glaxo Research and Development), Ribbon (University of Alabama), NAOMI (Oxford University), Explorer Eyechem (Silicon Graphics, Inc.), Univision (Cray Research), Molscript (Uppsala University), Chem-3D (Cambridge Scientific), Chain (Baylor College of Medicine), O (Uppsala University), GRASP (Columbia University), X-Plor (Molecular Simulations, Inc.; Yale University), Spartan (Wavefunction, Inc.), Catalyst (Molecular Simulations, Inc.), Molcadd (Tripos, Inc.), VMD (University of Illinois/Beckman Institute), Sculpt (Interactive Simulations, Inc.), Procheck (Brookhaven National Laboratory), DGEOM (QCPE), RE_VIEW (Brunel University), Modeller (Birbeck College, University of London), Xmol (Minnesota Supercomputing Center), Protein Expert (Cambridge Scientific), HyperChem (Hypercube), MD Display (University of Washington), PKB (National Center for Biotechnology Information, NIH), ChemX (Chemical Design, Ltd.), Cameleon (Oxford Molecular, Inc.), and Iditis (Oxford Molecular, Inc.). One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node, for example, is ScanProsite, MotifScan, InterProScan, ps_scan, and PRATT. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for protein identification and characterization is AACompIdent, AACompSim, MultiIdent, PeptIdent, TagIdent, FindMod, GlycoMod, GlycanMass, FindPept, PeptideMass, PeptideCutter, PepMAPPER, Mascot, PepSea, PeptideSearch, ProteinProspector, PROWL, PFMUTS, and CombSearch. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for DNA to Protein analysis and function is Translate, Transeq, Graphical Codon Usage Analyser, BCM search launcher, Backtranslation, Genewise, FSED, and LabOnWeb. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for similarity searches is BLAST and WU-BLAST, BLAST, BLAST at EMBnet-CH/SIB (Switzerland), BLAST at NCBI, WU-BLAST at Bork's group in EMBL (Heidelberg), WU-BLAST and BLAST at the EBI (Hinxton), BLAST at PBIL (Lyon), Bic ultra-fast rigorous (Smith/Waterman) similarity searches using the Bioccelerator [At DKFZ or at Weizmann], MPsrch, DeCypher, Fasta3, FDF, SAMBA, SAWTED, and Scanps. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Pattern and profile searches is InterPro Scan, Pfam, ScanProsite, MotifScan, Frame-ProfileScan, Pfam HMM search, FingerPRINT-Scan, FPAT, ELM, PRATT, PPSEARCH, PROSITE scan, PATTINPROT, SMART, HITS, and TEIRESIAS. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Post-translational modification prediction is SignalP, ChloroP, MITOPROT, Predotar, PlasMit, PATS, NetOGlyc, NetNGlyc, DictyOGlyc, YinOYang, big-PI Predictor, DGPI, NetPhos, NetPicoRNA, NMT, Sulfinator, and SUMOplot. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Topology prediction is PSORT, TargetP, DAS, HMMTOP, PredictProtein, SOSUI, TMAP, TMHMM, Tmpred, and TopPred 2. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Primary structure analysis is ProtParam, MW, pI, Titration curve, REP, REPRO, Radar, SAPS, Coils, Paircoil, Multicoil, 2ZIP, PESTfind, HLA_Bind, SYFPEITHI, ProtScale, Drawhca, Protein Colourer, Three To One, Colorseq, HelixWheel/HelixDraw, and RandSeq. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Secondary structure prediction is AGADIR, BCM PSSP, Prof, GOR I, GOR II, GOR IV, HNN, Jpred, nnPredict, PredictProtein, PHDsec, PHDacc, PHDhtm, PHDtopology, PHDthreader, MaxHom, EvalSec, PSA, PSIpred, SOPM (Geourjon and Deleage, 1994), and SOPMA (Geourjon and Deléage, 1995). One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Tertiary structure is SWISS-MODEL, Geno3d, CPHmodels, DisEMBL, preGlobPlot, 3D-PSSM, Foldfit, ProSup, SWEET, and Swiss-PdbViewer. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Sequence alignment is Binary, SIM+LALNVIEW, SIM, LALNVIEW, LALIGN, Dotlet, Multiple, CLUSTALW [At EBI, PBIL or at EMBnet-CH], T-Coffee [At EMBnet Switzerland or at CMBI], ALIGN, DIALIGN, Match-Box, MSA, Multalin [At INRA or at PBIL], MUSCA, AMAS, Bork's alignment tools, CINEMA, ESPript, WebLogo, plogo, GENIO/logo, and Sequence logos. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

A non-limiting list of functional activities that can be acquired and performed on a functional node for Biological text analysis is AcroMed, AbXtract, MedMiner, Protein Annotator's Assistant, and XplorMed. One of skill in the art understands what these programs are and where and how to obtain them. Furthermore, one of skill understands the function that the programs perform, and that other programs can perform the same function, and these other programs are considered disclosed herein. Thus, programs having the function of any of the programs identified in this paragraph are also disclosed, as well as the function of these programs understood in the art is disclosed.

c) Network Switch Nodes

All of the nodes in the cluster can be internally connected via a GigE network using a Foundry Big Iron 15000 switch supporting jumbo frames, or any similar type of equipment The switch acts as network concentrators, taking multiple network inputs, and combining them into one network feed. In addition the switch provides multifunction wire-speed switching and multi-protocol routing on a single, chassis-based platform. This platform supports a variety of interfaces including 10/100 Ethernet, Gigabit Ethernet Packet over Sonet (POS), and ATM interface modules. As disclosed herein the switch node can control the parsing out of subsets of databases to the functional nodes and can monitor the activity on the functional nodes.

d) Hardware

An example of the type of hardware that can be used in the disclosed clusters can be found in Example 3. Generally, however, it is understood that the disclosed clusters comprise various pieces of computer hardware. For example, there are clusters can comprise processors and memory means, as well as machine-readable storage mediums.

Disclosed are machine-readable storage mediums comprising a data storage material encoded with machine readable data. Furthermore, the data can be extracted and manipulated by machines configured to read the data stored on the machine readable storage media, and in fact, when performing for example sequence comparisons, as discussed herein, typically the data will be retrieved or stored on a machine readable storage media.

The disclosed data can be manipulated on any appropriate machine, having for example, a processor, memory, and a monitor. The data can also be manipulated and accessed by a variety of connected items, including printers, LCDs, for example.

The hardware architecture used for structural analysis and manipulation according to the present invention will include a system processor potentially including multiple processing elements where each processing element can be supported via, for example, a G5 processor such as provided in a G5 workstation (Apple computers); alternative processors such as Intel-compatible processor platforms using at least one PENTIUM III or CELERON (Intel Corp., Santa Clara, Calif.) class processor, UltraSPARC (Sun Microsystems, Palo Alto, Calif.) or other equivalent processors could be used in other embodiments. The system processor can include combinations of different processors from different vendors. In some embodiments, analysis and manipulation functionality, as further described below, can be distributed across multiple processing elements. The term processing element can refer to (1) a process running on a particular piece, or across particular pieces, of hardware, (2) a particular piece of hardware, or either (1) or (2) as the context allows.

The hardware includes a system data store (SDS) that could include a variety of primary and secondary storage elements. In one preferred embodiment, the SDS would include RAM as part of the primary storage; the amount of RAM might range from 32 MB to 100 GB or more, although these amounts could vary and represent overlapping use. The primary storage can in some embodiments include other forms of memory such as cache memory, registers, non-volatile memory (e.g., FLASH, ROM, EPROM, etc.), etc.

The SDS can also include secondary storage including single, multiple and/or varied servers and storage elements. For example, the SDS can use internal storage devices connected to the system processor. In embodiments where a single processing element supports all of the analysis and manipulation functionality, a local hard disk drive can serve as the secondary storage of the SDS, and a disk operating system executing on such a single processing element can act as a data server receiving and servicing data requests.

It will be understood by those skilled in the art that the different information used in the processes and systems according to the present invention can be logically or physically segregated within a single device serving as secondary storage for the SDS; multiple related data stores accessible through a unified management system, which together serve as the SDS; or multiple independent data stores individually accessible through disparate management systems, which can in some embodiments be collectively viewed as the SDS. The various storage elements that comprise the physical architecture of the SDS can be centrally located, or distributed across a variety of diverse locations.

The architecture of the secondary storage of the system data store can vary significantly in different embodiments. In several embodiments, database(s) can be used to store and manipulate the data; in some such embodiments, one or more relational database management systems, such as DB2 (IBM, White Plains, N.Y.), SQL Server (Microsoft, Redmond, Wash.), ACCESS (Microsoft, Redmond, Wash.), ORACLE 8i (Oracle Corp., Redwood Shores, Calif.), Ingres (Computer Associates, Islandia, N.Y.), MySQL (MYSQL AB, Sweden) or Adaptive Server Enterprise (Sybase Inc., Emeryville, Calif.), can be used in connection with a variety of storage devices/file servers that can include one or more standard magnetic and/or optical disk drives using any appropriate interface including, without limitation, IDE, EISA and SCSI. In some embodiments, a tape library such as Exabyte X80 (Exabyte Corporation, Boulder, Colo.), a storage attached network (SAN) solution such as available from (EMC, Inc., Hopkinton, Mass.), a network attached storage (NAS) solution such as a NetApp Filer 740 (Network Appliances, Sunnyvale, Calif.), or combinations thereof can be used.

In other embodiments, the data store can use database systems with other architectures such as object-oriented, spatial, object-relational or hierarchical or can use other storage implementations such as hash tables or flat files or combinations of such architectures. Such alternative approaches can use data servers other than database management systems such as a hash table look-up server, procedure and/or process and/or a flat file retrieval server, procedure and/or process. Further, the SDS can use a combination of any of such approaches in organizing its secondary storage architecture.

In one preferred embodiment, coordinate data is stored in flat ASCII files according to a standardize format. In one such embodiment, the standardized format is PDB as which is used through out the protein structure industry. The column content of the Tables containing coordinate data disclosed herein follows the PDB formatting and nomenclature.

The hardware platform would have an appropriate operating system such as WINDOWS/NT, WINDOWS 2000 or WINDOWS/XP Server (Microsoft, Redmond, Wash.), Solaris (Sun Microsystems, Palo Alto, Calif.), or IRIX (or other UNIX/LINUX variant). In one preferred embodiment, the hardware platform includes an IRIX operating system running on a SILICON GRAPHICS INDIGO$^2$ IMPACT workstation.

2. Systems

Contemplated herein is a computer system for comparing a first set of sequences to a second set of sequences, the system comprising a first database containing a first set of sequences, a second database containing a second set of sequences, and a network switch in communication with both the first and second databases.

The network switch can also be in communication with a set of computer search nodes. The system, including the search nodes, can be scalable, and as described above, there can be multiple search nodes.

As described above, the database system can use Cold Fusion, Oracle, Windows NT, SQL and MYSQL or any other database capable of storing the necessary data.

The network can be the Internet, and can use FTP, such as GridFTP or CuteFTP.

Also disclosed is a computer system having a memory means, a data input means, and a visual display means, the memory means containing the first set of sequences, and modules containing information to be coordinated with the first set of sequences, and the memory means being operable to retrieve coordinate data from the memory means and to display an executive summary on the visual display means, the executive summary containing a representation of the first set of sequences, and information from the modules.

Also disclosed is a computer system comprising a cluster computer, wherein the system can semi-automatically process a plurality of Blast searches when the databases change, producing a dynamic database that is regularly and automatically updated.

Described herein is a computer cluster comprising a first database node, a second database node, a network switch and at least two computer search nodes, wherein the network switch is in communication with the first database node, the second database node, and the computer search nodes. The first database node can comprise a database of biologically significant information. The second database node can comprise a database that is mirrored. The network switch can upload the information from the first database and upload the information from the second database as well. The network switch can parse the information from the first database into a number of subsets equal to the number of computer search nodes and distribute one subset to each computer search node. Furthermore, the network switch can download the second database to each computer search node. The network switch can also monitor the activity on the computer search nodes and when the activity on one computer search node is complete identifies the activity remaining to be completed on the other computer search nodes, parse the remaining activity into a second set of subsets equal to the number of computer search nodes in the system, and distributes one second subset to each computer search node. The second database node can be continually updated, as described above.

The first database can have at least 0.1, 0.2, 0.3, 0.4, 0.5, 0.6, 0.7, 0.8, 0.9, 1, 3, 5, 8, 10, 12, 15, 20, 30, 40, 50, 75, or 100 gigabytes of data.

The periodic search can be performed at least three times, producing a first, second, and third generation of the periodic output. Each generation of the periodic output represents updated information obtained from a database containing such information. The second database can be a dynamic database, in which there are at least a first generation, a second generation, and a third generation of the database. The generations can be accessed separately. The information uploaded will generally come from the most recent generation, however the system can be overridden such that any of the generations can be uploaded. At least two generations of the first database can be stored in globally accessible space, and at least one generation of the first database can be stored remotely. More generations can be stored remotely, such as 2, 3, 4, 5, or more. More generations can also be stored in globally accessible space, such as 3, 4, 5, 6, 7, 8, 9, 10, or more. At least two generations of the first database can be stored locally, such as on a local hard drive, and can be globally accessible as well. The analysis search can optionally query the first database stored globally or can copy the first database to a local node. The first database can also be transferred from globally accessible space using remote copy. Examples of transfer means to transfer from globally accessible space include using GridFTP. The periodic search can be performed on a dedicated node called a periodic search node.

The second database node can comprise a storage means large enough to store at least two generations of the first database. Furthermore, the periodic search node can utilize an updating scheme, wherein the updating scheme allows updating of the first database and analysis searching of the database without interference.

3. Exemplary Methods

Described herein are methods for creating a database for managing multiple types of biological information comprising obtaining a form of biological information, inputting the biological information into the database as a new record, wherein the record is associated with a unique identifier, comparing the information in the record to the information already present in the database, determining whether the information in the new record already exists in the database, adding the information to the database if it is not redundant to the database information, thereby forming a set of records in the database, where each record is associated with a unique identifier, creating at least one module for a specific type of biological information that is associated with each unique identifier, obtaining a form of biological information associated with a module in the database, associating the biological information with the correct module in the database, and associating the biological information with the correct unique identifier.

By "biological information" is meant any type of information that can be derived for any type of biological system. For example, the information can be nucleotide or amino acid sequence information.

The unique identifier can be any form of identification, unique to the biological information, which forms a record of that information and allows it to be subsequently retrieved. For example, the information can be associated with a unique number, or letters, or a combination of numbers or letters. The record can also be associated with any form of symbol.

Also disclosed is a method of creating an executive summary of biologically significant information, the method comprising inputting biologically significant information in a database; checking the biologically significant information against the database for redundancy; sending sequences from the biologically significant information to a second database for comparison; receiving replies from the second database in response to a comparison query; saving the replies in the database, thereby creating a module; collecting all of the modules associated with each identifier; and outputting the information contained in the modules for each unique identifier in an executive summary.

Also disclosed is a method of displaying an executive summary of biologically significant information on a computer wherein the computer comprises a processing means, a memory means, an input means and an output means comprising: collecting information from individual information modules related to a unique identifier, wherein the unique identifier is associated with a particular record; producing a coordinated display of information from the individual modules; and displaying the information from the individual modules using a visual display means producing the executive summary.

Described herein are methods of displaying an executive summary containing information related to a unique identifier associated with a first set of sequences comprising: determining a first set of sequences; providing a computer system having a memory means, a data input means, and a visual display means, the memory means containing the first set of sequences, and modules containing information to be coordinated with the first set of sequences, and the memory means being operable to retrieve coordinate data from the memory means and to display an executive summary on the visual display means, the executive summary containing a representation of the first set of sequences, and information from the modules; uploading information from a second database containing sequence comparison data to the computer system; creating a module based on information obtained from the second database containing sequence comparison data; searching for other modules associated with the unique identifier; creating an executive summary containing information from the modules; and displaying the executive summary containing information on the first set of sequences and all the modules associated therewith.

Described herein are methods of comparing a first set of sequences to a second set of sequences, the method comprising: uploading the first set of sequences associated with a unique identifier contained as a module in a record in a first database into a network switch node, uploading the second set of sequences contained in a second database into the network switch node, parsing the first set of sequences into subsets of sequences, allocating each subset of sequences to a search node, downloading the second set of sequences to each search node, comparing the subset of sequences to the second set of sequences on the search node, thereby forming an alignment, or comparison, of the first set of sequences and the second set of sequences, monitoring the status of each comparison on each search node, until a particular search node completes the comparison of the subset of sequences being performed, thereby forming a completed node, identifying the sequences in the subset of sequence on each node other than the completed node that have not yet been compared to the second set of sequences forming a set of remaining sequences, parsing the set of remaining sequences into a second subset of sequences, allocating the second subset of sequences onto each node, and comparing the second subset of sequences to the second set of sequences, and repeating the above steps until each sequence in the first set of sequences has been compared to each sequence in the second set of sequences, updating the information in the first database with the results of the comparison of the first set of sequences to the second set of sequences.

In one embodiment, comparing biological information means aligning a first set of sequences with a second set of sequences, thereby generating comparison data between the sequences.

In the above methods, the network database can be in communication with a set of computer nodes and can be scalable. By "scalable" is meant that the network database is able to monitor the work load of the nodes and distribute work to them accordingly, so as to constantly have a relatively even amount of work distributed between the nodes at any given time. For example, the network switch can monitor the activity on the computer search nodes and when the activity on one computer search node is complete identifies the activity remaining to be completed on the other computer search nodes, parse the remaining activity into a second set of subsets equal to the number of computer search nodes in the system, and distributes one second subset to each computer search node.

There can be 2, 3, 4, 5, 6, 7, 8, 9, 10, 11, 12, 13, 14, 15, 16, 17, 18, 19, 20, or more search nodes operating in the system and in communication with the network database.

With the methods described herein, it is possible to identify which records in the first database have changed after the step of updating. For example, a report can be generated that indicates which records have changed since the last updating. The report can be automatically sent via e-mail to a predetermined address, or the changed information can be flagged, the flags being searchable in the database.

The second database described above can be a mirror database. By "mirror database" is meant a database that reflects information found on another database. For example, the National Center for Biotechnology Information maintains a database that is accessible to users. In order to expedite use of this database, users are able to upload information from this database into their own, and utilize the data found on the mirror site instead of the home site. The mirror database can mine, for example Genbank, Pfam, Prodom, and Prosite database.

The second database can be continually updated on a separate node. For example, when a mirror database is used, the information contained therein is periodically updated and that new information must be transmitted to the second database in order to keep it up to date. Updating of the second database can occur over the Internet, and can utilize FTP, for example, to download the information. One example of a type of FTP that can be used is GridFTP. Another example is CuteFTP.

If the information utilized by the search node is sequence information, the search node can perform a BLAST search, for example. The sequence comparison data can also be analyzed to determine categories, subcategories and keywords for the unique identification number.

Throughout the application, an example of a first database is referred to as SMEDDb. This is an example of a name given to the database, but is not intended to be limiting in any way to a certain type of organism.

The first database can comprise a module for spatial information and a module for temporal information.

The second database can comprise an HTML file readable by a web browser. The HTML file can incorporate an image relating to a sequence, for example the HTML file can also be accessed remotely through a computer network.

Figure 16:
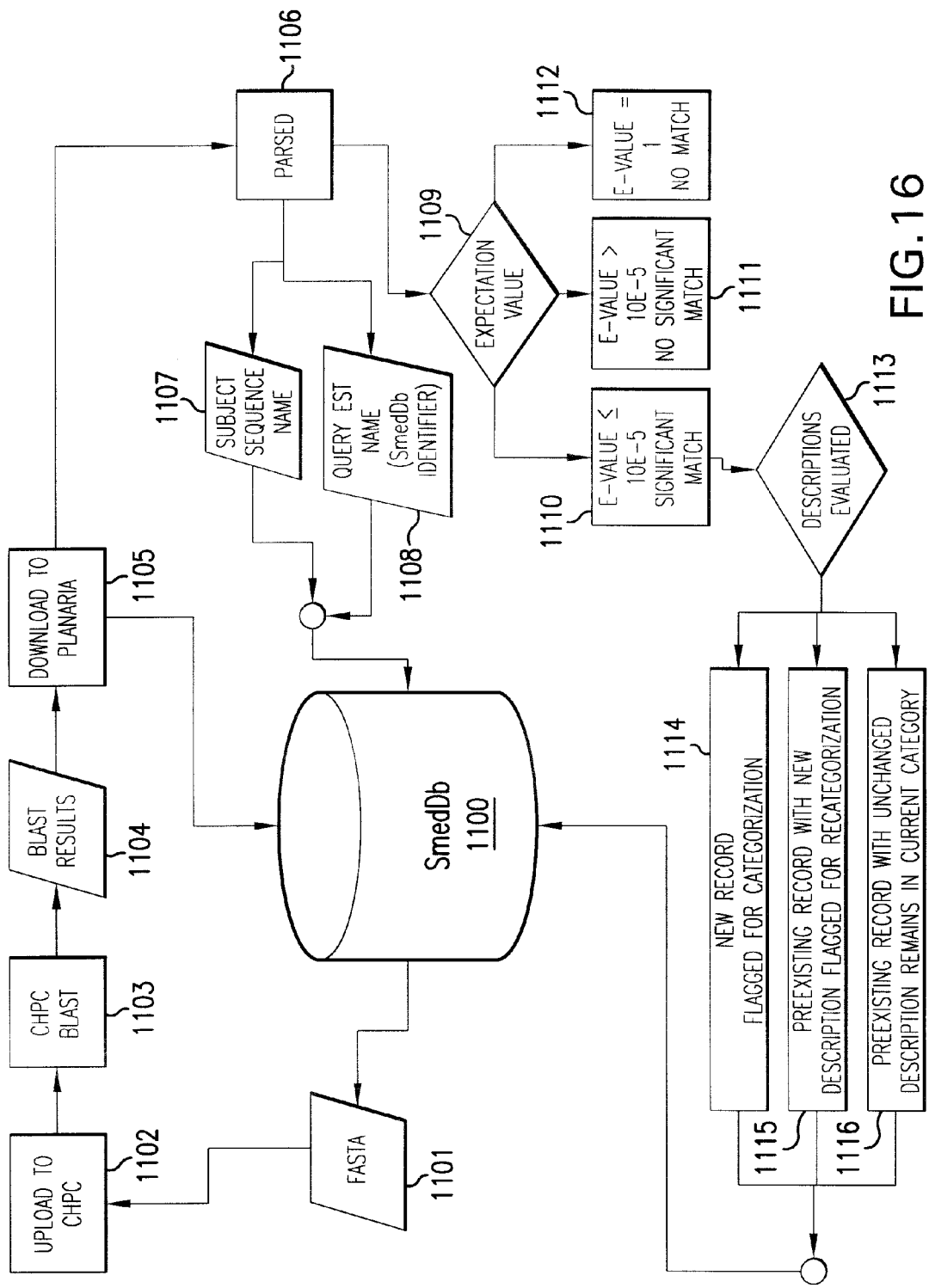

FIG. 16 shows a flowchart for an embodiment of the disclosed methods and system. Box 1100 represents, for example, a first database or a target database, such as the SmedDb, which outputs a fasta file of its sequence contents (1101). These FASTA files are uploaded to a node, such as a switch node, 1102, which are then downloaded to a functional node, that can, for example, perform a BLAST search (1103). The function results are then downloaded to the original database (1105). Concurrently, prior to, or after, the downloaded results are collected and parsed (1006) and they are given a subject sequence name (1107) and a query EST name, the database identifier (1108). The parsed sequences are given an expectation value (1109) and depending on what the value is the database is either updated in one of three ways or the database is not updated (1110, 1111, 1112, 1115, 1114, 1115, and 1116). This embodiment can be combined with any of the embodiments and other variations as disclosed herein.

Figure 17:
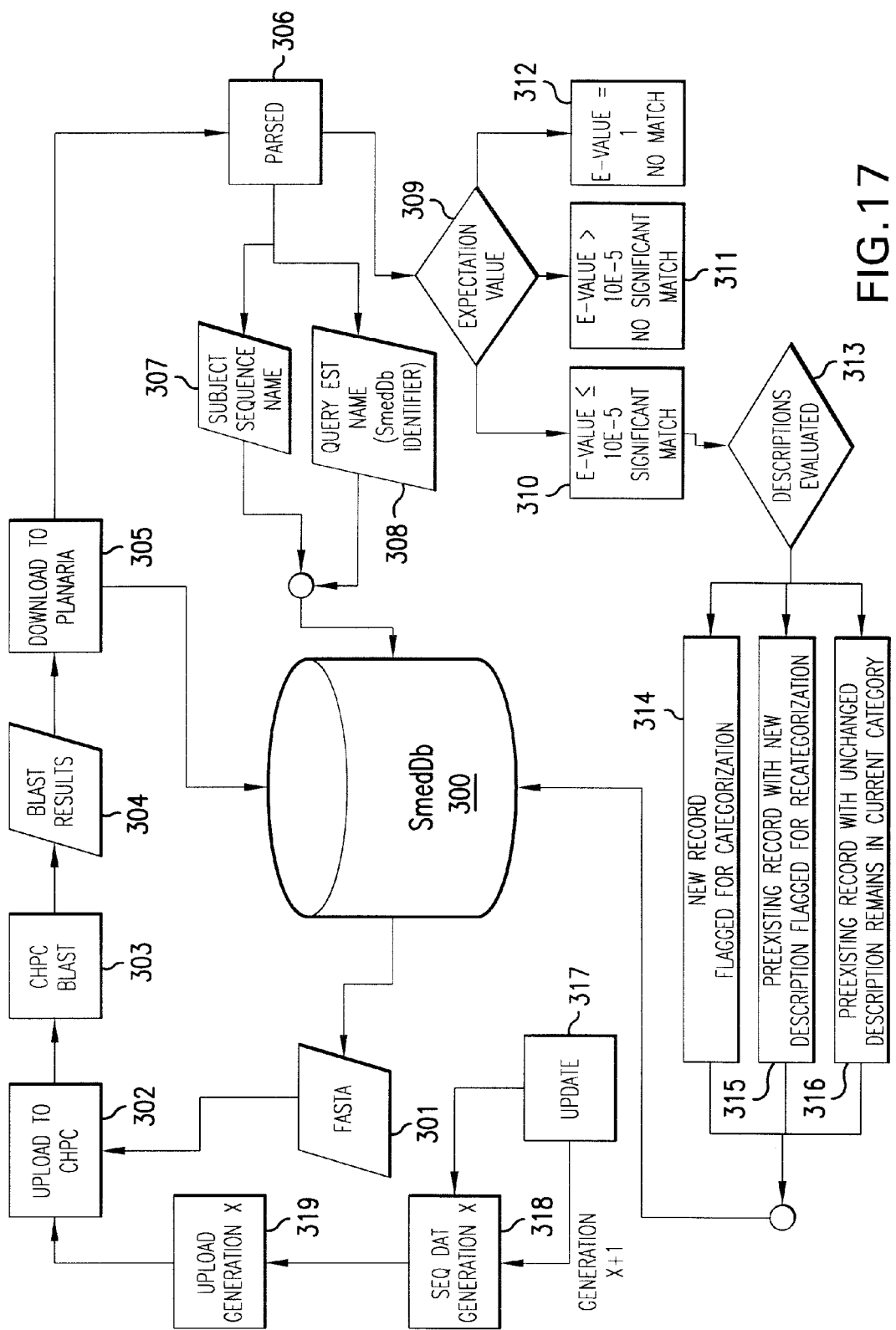
FIG. 17 shows a flow diagram for the SmedDb database.

FIG. 17 is similar to FIG. 16. Boxes 300, 301, 302, 3003, 304, 305, 306, 307, 308, 309, 310, 311, 312, 313, 314, 315, and 316 are like boxes 1100, 1101, 1102, 1103, 1104, 1105, 1106, 1107, 1108, 1109, 1110, 1111, 1112, 1113, 1114, 1115, and 1116 respectively. Boxes 317, 318, and 219 show a routine where a second database, such as a SEQ DAT, or second database, or query database, such as Genbank is also uploaded to the network switch (319). The diagram shows that the second database is either continually or periodically updated (317) and that the database node is has multiple generations of the second database on it, and the updated version at any given time is generation X+1 and the generation that is downloaded to the network switch is generation x or generation X−1, for example.

Figure 18:
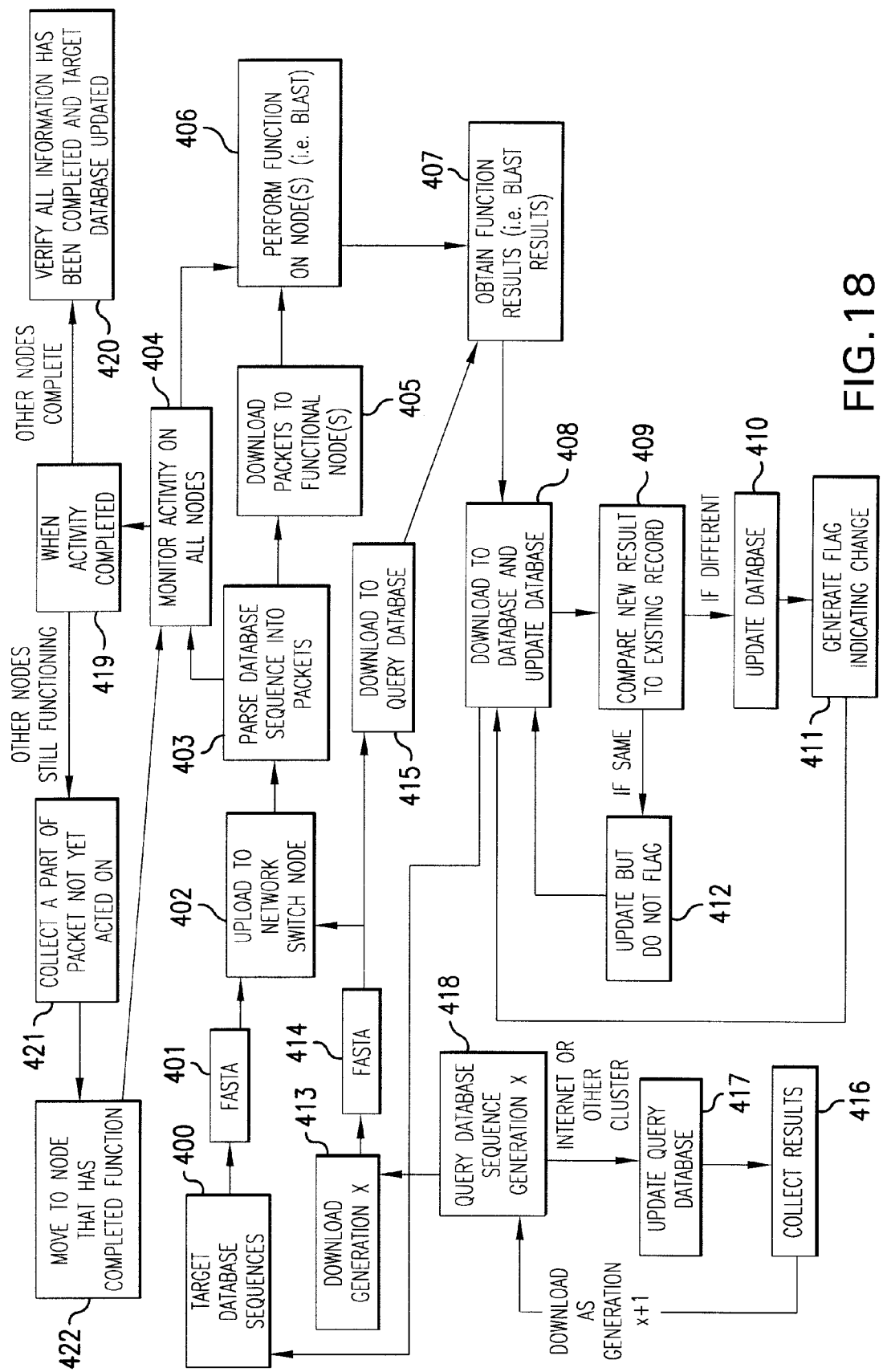
FIG. 18 shows a flow diagram for the processing of target database sequences.

FIG. 18 shows a flowchart that describes an embodiment of the disclosed methods for managing databases. Box 400 shows a target database sequence set as described herein. This set of sequences can be turned into FASTA files (401) and uploaded to a network switch node (402) which will parse the sequences into packets or subsets, of sequences. (403). These packets are downloaded to one or more functional nodes (405) and the functional nodes can begin performing the designated function, such as a BLAST search (406) against a generation (413) of a query database, such as a Genbank database which has been downloaded to the functional node as well (415) after being turned into a FASTA file (414). The query database resides on a node (418) in multiple generations, and is updated, either periodically or continually, (417) and the results of the update are completed in the background and then downloaded to the query database node as generation x+1 of the query database (416). The network switch can monitor what is happening on the functional nodes (404) and if the activity is completed on one or more nodes (419) and there are other nodes still functioning the network switch will collect a part of the remaining unfinished packets on the other node(s) (421) and move this repacketed or new subset of information to a node that has completed the function. (422). It is understood that this can be done singularly, i.e one running node can have its remaining sequences parsed, or more than one node could have the remaining sequences collected and redistributed on the nodes from which the remaining sequences were collected along with the node that was no longer functioning, or a subset of these nodes. Many variations of this monitoring can occur, and can be controlled in part based on the physical set up of the cluster. If the other nodes are complete when the activity is completed (420) the network switch node can verify the information that has been completed and monitor the updated target database. When the functional node performs its function, such as a BLAST search (406), it produces a result (407) which is then downloaded to the target database (408). While this downloading is occurring, prior to, or after, the downloaded result can be compared to the existing information in the module in the record that the information is related to (409) and if the information is the same, the module in the record can be updated, but does not need to be, but the record is not flagged as an updated record (412). If the result is different after the comparison, the database can be updated (410) and when this occurs a the changed record can be flagged (411) and if desired a report, such as an executive summary can be generated containing all of the information of the record. Furthermore, automatic e-mail notifies, for example, can be created to indicated a record has changed. This method can be performed with many variations as discussed herein on the systems disclosed herein.

Figure 19:
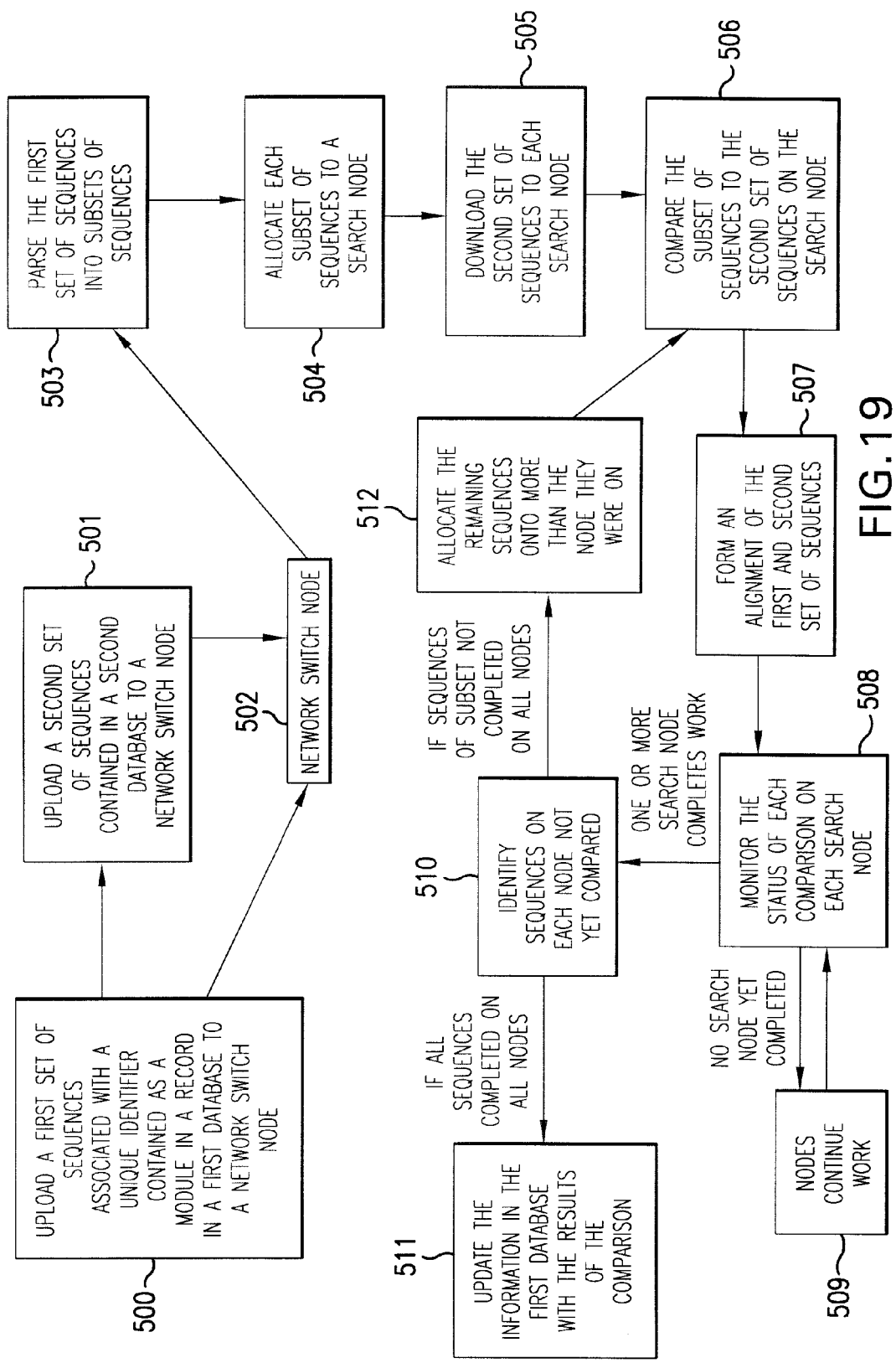
FIG. 19 shows a flow diagram for uploading sequence information to a switch node.

FIG. 19 shows a flow chart of an embodiment of the disclosed methods. In box 500, a first set of sequences that is associated with a unique identifier contained as a module in a record in a first database is uploaded to a network switch node (502). Either concurrently, prior to, or after, a second set of sequences contained in a second database is also uploaded (501) to the network switch (502). The network switch parses the first set of sequences into subsets of sequences (503) and then allocates each subset of sequences to a search node (504). Either prior to, concurrently, or after the subsets are downloaded, the second set of sequences is downloaded to each search node (505). The search nodes then perform a comparison of the subsets of sequences to the second set of sequences on the search node (506) and form an output, such as an alignment, (507). The system is continually monitored as to the status of each search node (508), by for example, the network switch, and if no node is complete with it comparison, such as a BLAST, the node work continues (509). If one or more search nodes completes the work, the sequences in the subsets on one or more nodes that have not yet been compared are identified (510). The sequences not yet completed in a search are identified and the allocated onto more than the node they were on (512) and the comparison of the subsets of sequences with the second set of sequences continues (506), until all sequences in all subsets have been compared to the second set of sequences (509). When everything has been completed or concurrently, the comparison information is outputted and the first database is updated (511). It is understood that many variations of this method exist and that different parts and subparts can be used or added or subtracted. For example, the second database can be periodically or continually updated as disclosed herein.

Figure 20:
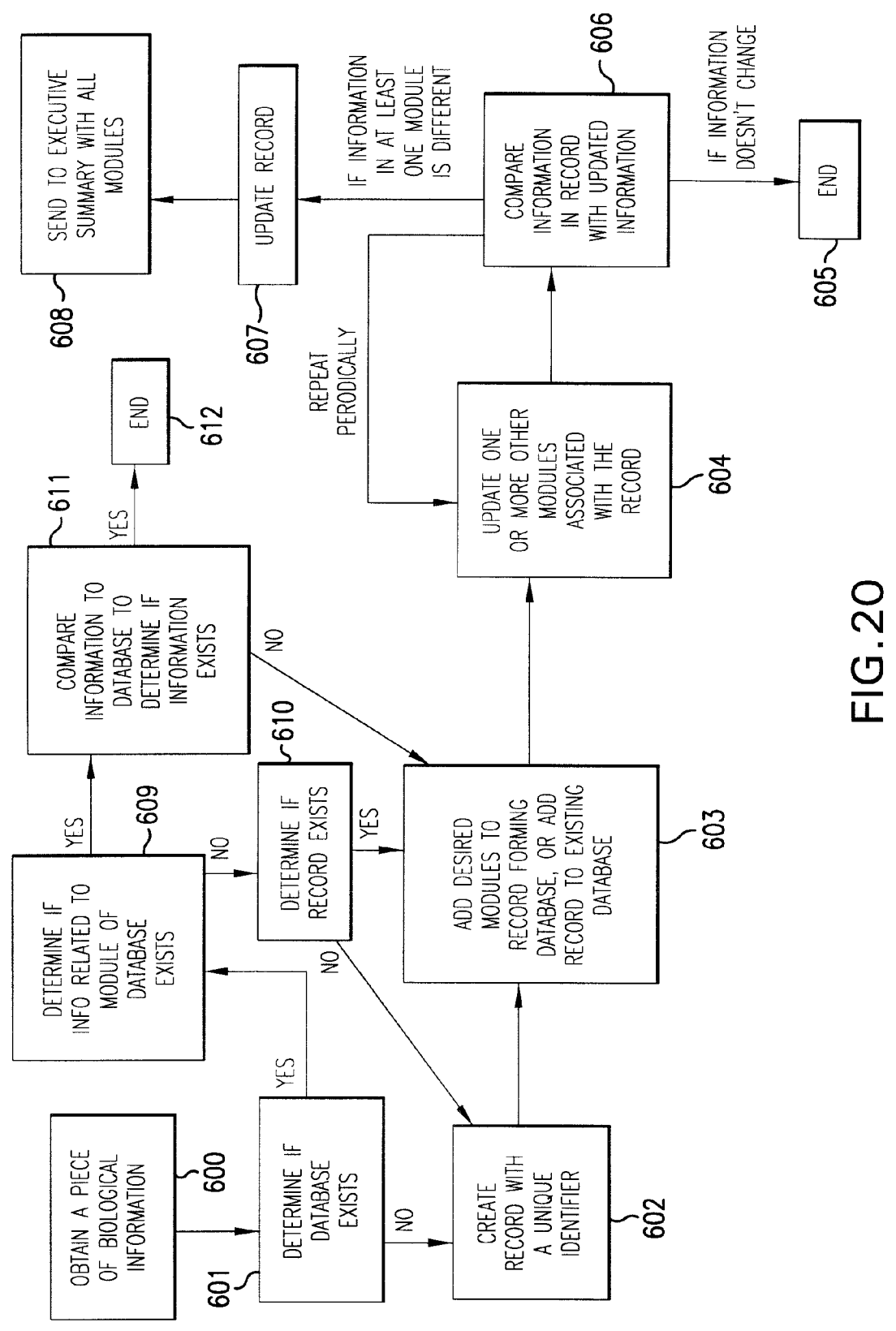

FIG. 20 shows a flowchart for creating a database that can be used herein, such as a target database, such as SmedDb. In box 600, a piece of information, any type of biological information such as an EST or cDNA, is collected, and it is determined if there is already a database in existence that this piece of information could be added to (601). If there is already a database, it is determined if the information is related to a module contained in the database (609). If the answer to 601 is no, a record with a unique identifier is created (602) and the desired modules are added to the record either creating the database if it is the first record or adding a new module to the records if the database is already existing (603). If the answer to box 609 is no, whether a record exists is determined (610) and if a record does exist a new module is created (603). If no record exists (601), a new record is created (602) and then a new module is created (603). If the answer to box 609 is yes, then the information is compared to the information already contained in the database to see if the information is present in the database (611). If the information exists, nothing more is done (612). If the information does not exist, then a new module is created (603). Once a new module is created then one or more modules can be periodically or continually updated, including the module that has just been created (604). This can be repeated periodically or continually and each time the appropriate modules in the database are updated and potentially flagged if information has changed as disclosed herein. If the information is contained in the database (606) then the database does not change (605). If the information in the update is new, the record is updated (607), and an executive summary with one or more or all of the pieces of information associated with the record is created (608). It is understood that variations and additions can be performed with this embodiment as disclosed herein.

Figure 21:
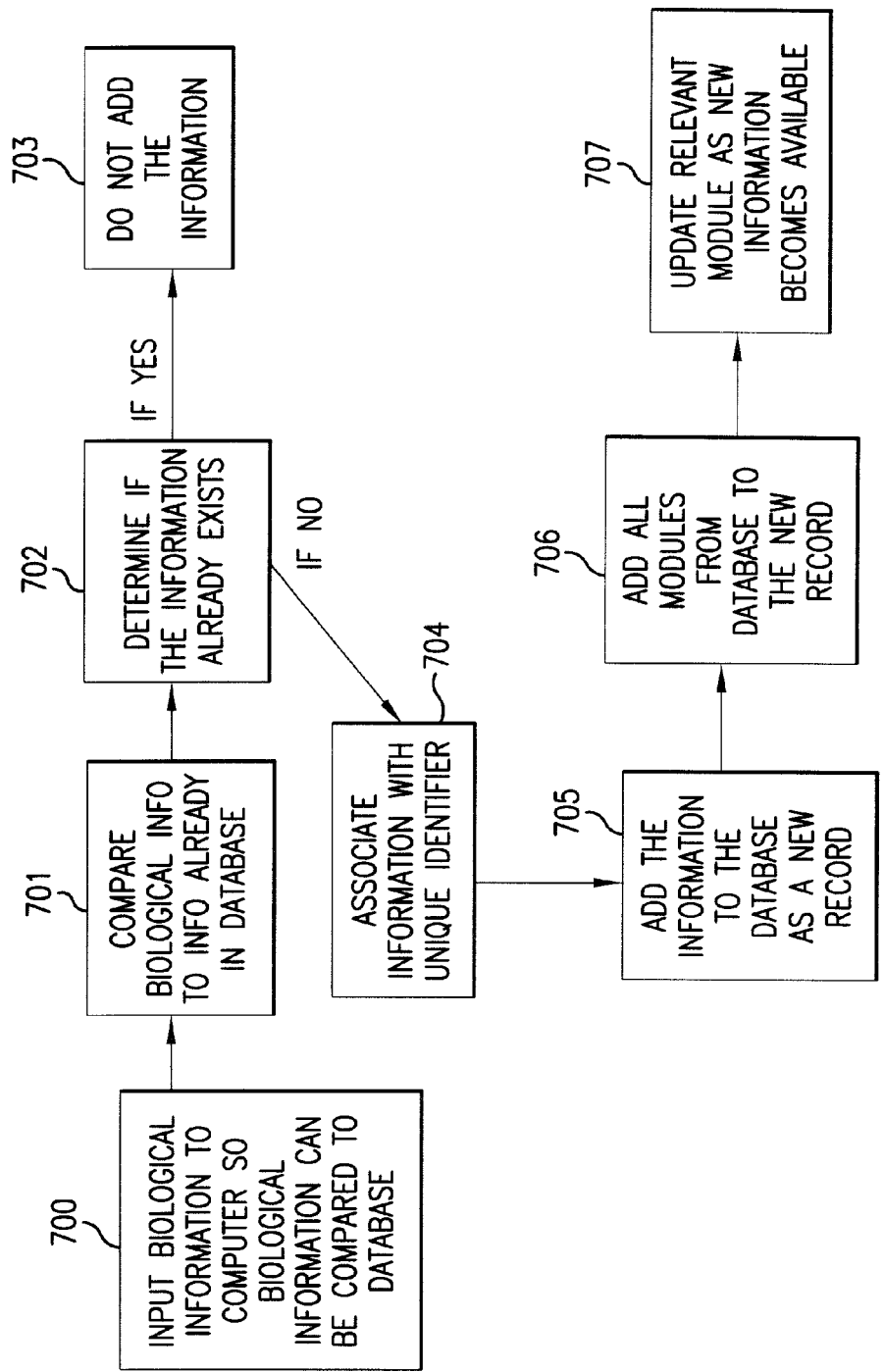
FIG. 21 shows a flow diagram for comparing biological information to a database.

FIG. 21 shows a flowchart for creating a database that can be used herein, such as a target database, such as SmedDb. In box 700, a piece of biological information is inputted into a computer so that the biological information can be compared to the database the information is potentially going into (700).

The information is then compared (701) to the information already in the database. It is determined whether the information already exists (702) and if it does the information is not added (703). If the information does not exist then the information is associated with a unique identifier (704) and the information is added to the database as a new record (705). Then the record is completed by making sure that all of the different types of modules that the database contains for each record are associated with the new record (706). The modules of all the records including the new record can be updated as desired as disclosed herein, for example, periodically or continually.

Figure 22:
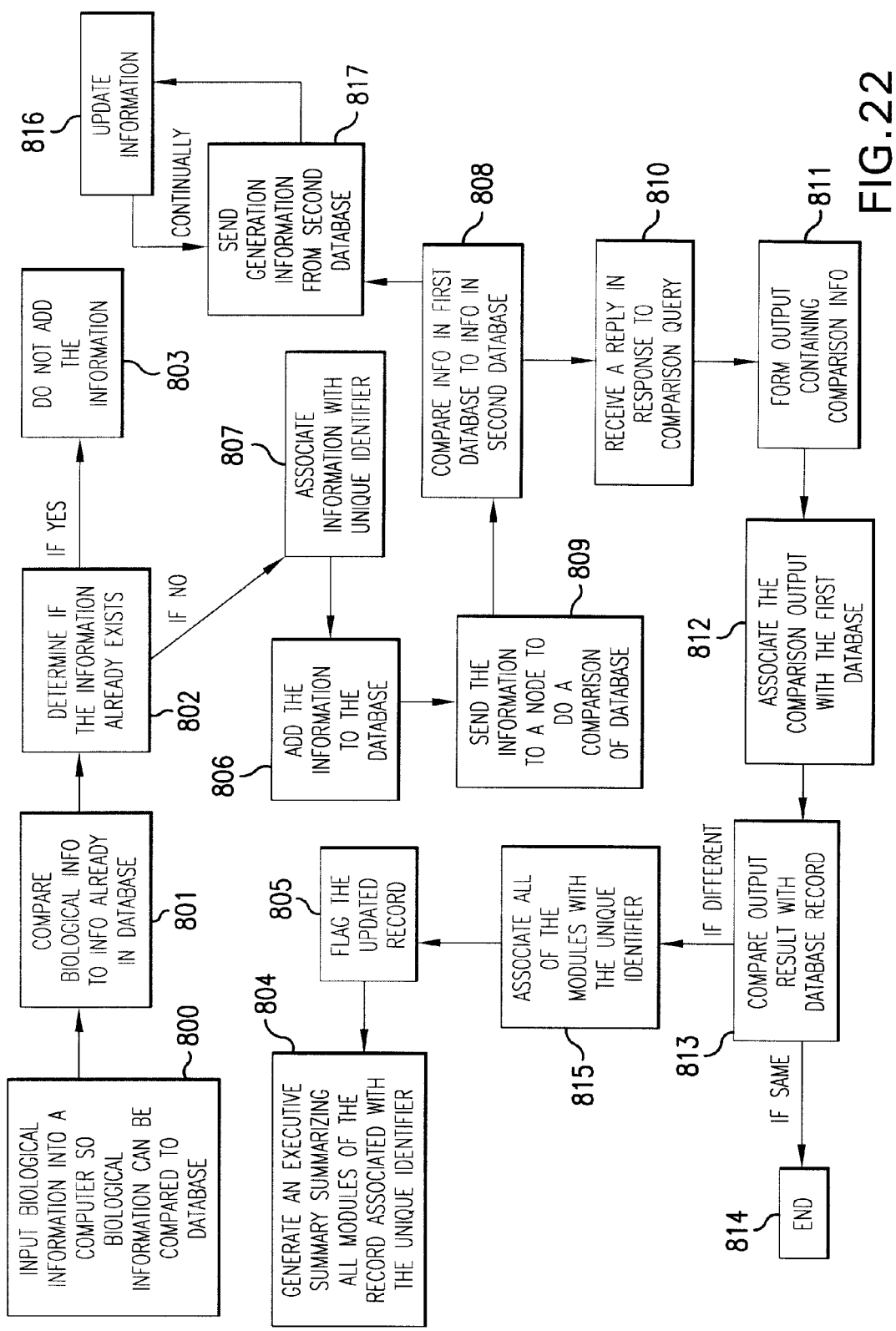
FIG. 22 shows a flow diagram for comparing biological information to a database.

FIG. 22 shows a flow chart for an embodiment of the disclosed methods and database formation as disclosed herein. Boxes 800, 801, 802, 807, 803, 806, are similar to boxes 700, 701, 702, 704, 703, and 705 respectively, of FIG. 21. After the information is added to the database (806) the information can be sent to a node to do a comparison of another database (809) and for example, the information in the first database can be compared to the information in a second database (808) and a reply can be received in response to the comparison query (810). An output can be created containing the comparison information (811 (and the comparison output can be associated with the first database (812)). The output can be compared with the database records to determine if it is the same as any record (813) and if they are the same, the method can stop (814). If the output is different then all of the modules can be associated with the unique identifier (815) and the updated record is flagged (805) and an executive report can be generated (804).

Figure 23:
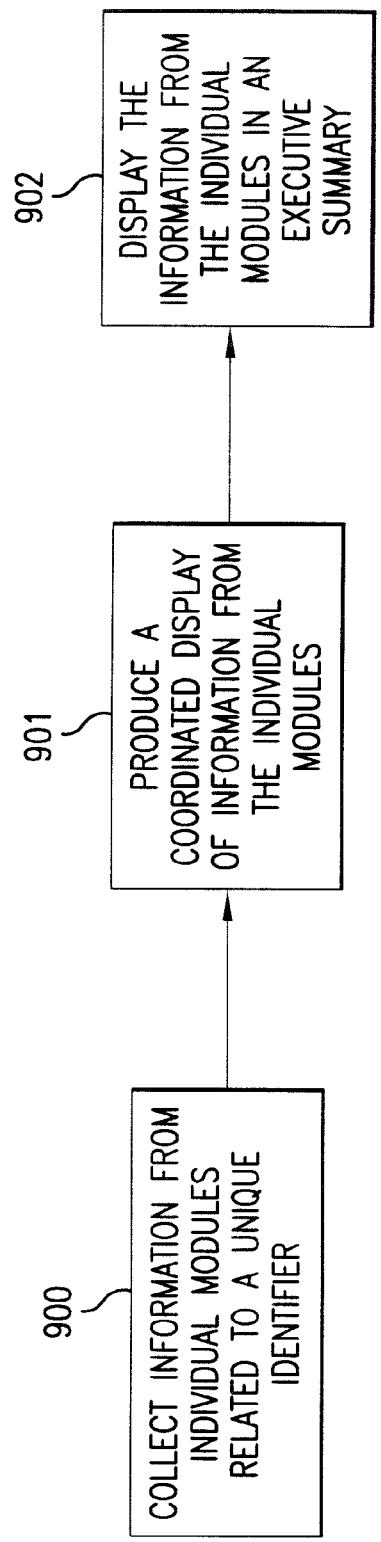
FIG. 23 shows a flow diagram for collecting information from individual modules related to a unique identifier.

FIG. 23 shows a flowchart for producing an executive summary as disclosed herein. In box 900 information can be collected from individual modules related to a unique identifier (900) and these can be used to produce a coordinated display of information from the individual modules (901). The information of all the modules can be displayed in an executive summary (902).

Figure 24:
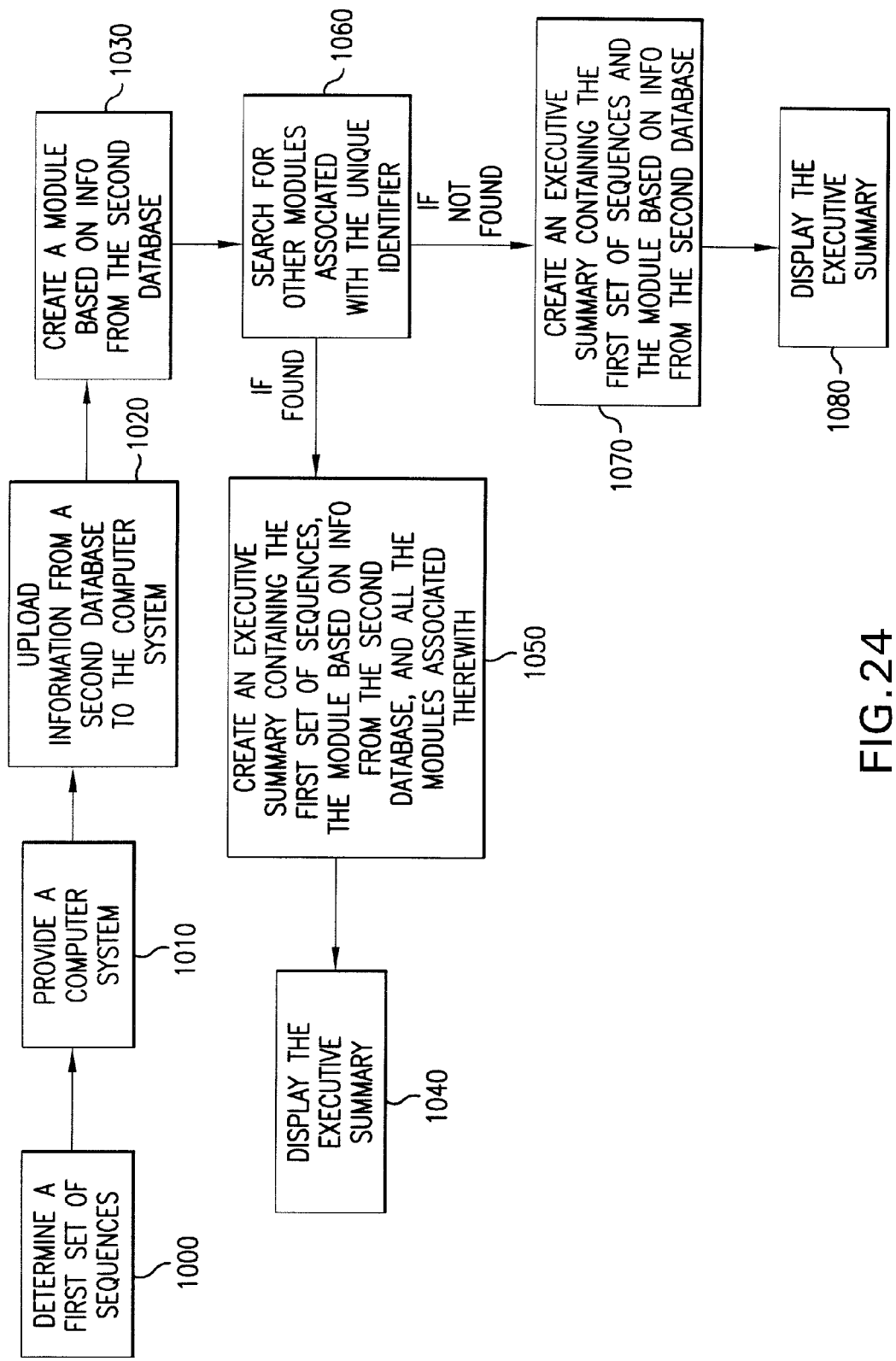
FIG. 24 shows a flow diagram for creating an executive summary.

FIG. 24 shows a flowchart for displaying information and creating executive summaries of biological information that has been grouped together in modules and a complete report. In box 1000 a first set of sequences is determined, a a computer system is provided in box 1010. Information from a second database is uploaded to the computer system (1020). A module is created based on the information from the second database (1030) and other modules are searched to see if the information is associated with a unique identifier (1060). If it is found then an executive summary is created (1050) and the summary is displayed (1040). If there is not a finding of the information in the other modules an executive summary is created that contains the first set of sequences and the module based on the info from the second database (1070) and the executive summary is displayed (1080).

B. PLANARIA

The phylum Platyhelminthes (flatworms) consists of approximately 50,000 different species that populate a remarkable variety of niches (Littlewood, T. J. and Bray, R. A. (2001), *Interrelationships of the Platyhelminthes*. London, New York: Taylor and Francis). In addition to free-living forms, it encompasses parasitic organisms responsible for inflicting debilitating diseases upon hundreds of millions of people throughout the world (see World Health Organization fact sheet 115 at http://www.who.int/inf-fs/en/fact115.html). Platyhelminthes are considered by many to occupy an important position in the evolution of the Metazoa (Adoutte, A., et al., (1999), *Trends Genet*. 15, 104-108; Henry, J. Q., et al., (2000), *Dev. Biol*. 220, 285-295; Tyler, S. (2001). The early worm: origins and relationships of the lower flatworms. In *Interrelationships of the Platyhelminthes* (ed. T. J. Littlewood and R. A. Bray), pp. 3-12. London, New York: Taylor and Francis; Willmer, P. (1994). *Invertebrate Relationships*. New York: Cambridge University Press), and the panoply of developmental properties displayed by these organisms has attracted the attention of generations of biologists (Newmark, P. A. and Sánchez Alvarado, A. (2002), *Nat. Rev. Genet*. 3, 210-219). For example, the ability of freshwater planarians to regenerate completely from small body fragments has been known for over two centuries (Morgan, T. H. (1898), *Arch. Entw. Mech. Org*. 7, 364-397; Randolph, H. (1897), *Arch. Entw. Mech. Org*. 5, 352-372), and the life cycles of some digenetic trematodes involve as many as three different hosts as well as both sexual and asexual strategies for their reproduction (Brusca, R. C. and Brusca, G. J. (1990), *Invertebrates*. Sunderland, M A: Sinauer Associates; Hyman, L. H. (1951). *The Invertebrates: Platyhelminthes and Rhynchocoela The Acoelomate Bilateria*. New York: McGraw-Hill). Yet, as important, abundant and diverse as platyhelminthes are, little is known about the molecular events that guide their sophisticated and often plastic biological properties.

Moreover, many members of this phylum possess large populations of undifferentiated mesenchymal stem cells, the study of which could contribute significantly to fundamental biomedical research in the areas of tissue regeneration, stem cell maintenance and degenerative disorders. In most free-living species these stem cells, which are often referred to as neoblasts, are used for the regeneration of missing body parts and/or the replacement of cells that are lost during the course of physiological turnover (Gschwentner, R., et al., (2001), *Cell Tissue Res*. 304, 401-408; Ladurner, P., et al., (2000), *Dev. Biol*. 226, 231-241; Newmark, P. and Sánchez Alvarado, A. (2000), *Dev. Biol*. 220, 142-153). Similarly, free mesenchymal cells in parasitic flukes are known to produce complete larval forms (Brusca, R. C. and Brusca, G. J. (1990). *Invertebrates*. Sunderland, M A: Sinauer Associates; Hyman, L. H. (1951). *The Invertebrates: Platyhelminthes and Rhynchocoela The Acoelomate Bilateria*. New York: McGraw-Hill), and in the cestode *Taenia crassiceps* complete cysts can be reconstituted from individual cells (Toledo et al., (1997), *J. Parasitol*. 83, 189-193). Thus, platyhelminthes also provide a unique opportunity for studying the mechanisms that underlie the control of cellular pluripotentiality.

C. COMPOSITIONS AND METHODS RELATED TO *SCHMIDTEA MEDITERRANEA*

Disclosed herein is the establishment of a clonal line of a diploid, asexual form of the planarian *Schmidtea mediterranea* (Turbellaria, Tricladida), along with the isolation and sequence characterization of ~3000 non-redundant, expressed sequence tags (ESTs) from this organism. Furthermore, disclosed is the suitability of using planarians for high-throughput mapping of gene expression patterns in the whole animal, and introduce the *S. mediterranea* Database (SmedDb) in which the primary data, computational analyses and expression data reside (http://planaria.neuro.utah.edu). The cells from the clonal lines can be used in a variety of methods, including RNA interference studies (Sanchez Alvarado, A. and Newmark, P. A. (1999), *Proc. Natl. Acad. Sci. USA* 96, 5049-5054) as well as labeling studies, to for example, label the *S. mediterranea* neoblasts specifically (Newmark, P. and Sanchez Alvarado, A. (2000), *Dev. Biol*. 220, 142-153) which will permit the identification and characterization of genes involved in regenerative processes, ranging from the control of stem cell proliferation and differentiation to the regulation of polarity, growth, scale and proportion.

The difficulty of obtaining, molecularly modifying and following the fate of gametes from animals traditionally utilized to study metazoan regeneration (hydra, planarians and salamanders) have precluded the application of traditional genetics to study their molecular properties. In recent years, however, methodological advances have been introduced which will allow researchers to overcome such difficulties. High-throughput sequencing, DNA and protein microarrays and RNA interference (RNAi) are among the emerging technologies that make possible the application of reverse-genetic strategies to identify and characterize molecular pathways in non-genetic organisms. The power of these techniques lies in the breadth, extent and complexity of the large datasets they tend to generate and their usefulness depends, in turn, on the computational analyses (bioinformatics) necessary to extract meaningful information from the data. Therefore, the development of flexible and modular databases that integrate bioinformatic tools in their architecture is required to integrate and interpret not only intra- but also inter-species data.

In the past few years, several groups (Agata K, Watanabe K. 1999, Semin Cell Dev Biol 00; Newmark P A, Sánchez Alvarado A. 2002, Nature Reviews Genetics 3:210-219) have endeavored to introduce functional genomic approaches to the study of regeneration in planarians. Disclosed herein are clonal lines of the stable diploid *Schmidtea mediterranea* which aid in the minimization of genetic variability and standardize molecular analyses. In addition, and aiming to carry out systematic molecular analyses of the intriguing biological properties displayed by freshwater planarians, loss-of-function assays in planarians via dsRNA have been performed, (Sánchez Alvarado A, Newmark P A., 1999, Proc. Natl. Acad. Sci. USA 96:5049-5054), methods to label the planarian stem cell (neoblast) and its progeny have occurred, (Newmark P, Sánchez Alvarado A. 2000, Dev Biol 220:142-153; Robb S M C, Sánchez Alvarado A. 2002, Genesis 32:293-298), and nearly 3,000 non-redundant cDNAs have been isolated from *S. mediterranea*.

The disclosed compositions and methods can be used for targeted gene disruption and modification because of their clonal nature. Gene modification and gene disruption refer to the methods, techniques, and compositions that surround the selective removal or alteration of a gene or stretch of chromosome in an animal, such as a mammal, in a way that propagates the modification through the germ line of the mammal. In general, a cell is transformed with a vector which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

One of the preferred characteristics of performing homologous recombination in mammalian cells is that the cells should be able to be cultured, because the desired recombination event occur at a low frequency.

Once the cell is produced through the methods described herein, an animal can be produced from this cell through either stem cell technology or cloning technology. For example, if the cell into which the nucleic acid was transfected was a stem cell for the organism, then this cell, after transfection and culturing, can be used to produce an organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies generally take the nucleus of the transfected cell and either through fusion or replacement fuse the transfected nucleus with an oocyte which can then be manipulated to produce an animal. The advantage of procedures that use cloning instead of ES technology is that cells other than ES cells can be transfected. For example, a fibroblast cell, which is very easy to culture can be used as the cell which is transfected and has a gene modification or disruption event take place, and then cells derived from this cell can be, used to clone a whole animal.

D. DEFINITIONS

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance can or can not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Systems and Methods for the Analysis, Integration, and Hypothesis Testing of Spatio-Temporal Gene Expression Patterns a) The *Schmidtea mediterranea* Database (SmedDb)

The *Schmidtea mediterranea* database known as SmedDb (Sánchez Alvarado A, et al., 2002, Development) is a depository of immunohistological data, and nucleotide sequences of expressed sequence tags (ESTs) and their expression patterns. Immunohistological data is organized according to positive or negative cross-reactivity of all antibodies tested by a laboratory against planarian tissues (as described below), while the information for the ESTs is organized into individual, self-contained records where pertinent information for each cDNA clone such as GenBank comparisons, Entrez-PubMed hyperlinks, and in situ data can be easily retrieved.

b) Immunohistology Marker Record

Two lists of antibodies comprising nearly 140 different polyclonal and monoclonal antibodies that have been tested for cross-reactivity with planarian tissues (Robb S M C, Sánchez Alvarado A. 2002, Genesis 32:293-298) can be found in SmedDb. Information on the source, dilution and type of secondary antibodies utilized is also provided. Confocal images of the immunohistological patterns obtained with cross-reacting antibodies can also be found in the database and new entries are added to the list as more antibodies are tested and characterized. This provides a reagent and pictorial reference of suitable antibody markers to the research community working on flatworms for the purpose of characterizing, for example, RNAi-induced phenotypes (Cebrià F, et al., 2002, Nature). This list is expandable as more markers are identified and published by including contributions from other planarian laboratories.

c) SmedDb EST Records

A large number of randomly selected cDNAs from clone CIW4 of *Schmidtea mediterranea* has been recently analyzed and archived in GenBank at the National Center for Biotechnology Information (NCBI) (Sánchez Alvarado A, et al., 2002, Development) The complexity of the libraries utilized to carry out the EST project is shown in FIG. 1. Approximately 68% of all clones sequenced (2021) had a frequency distribution equal to 1. If the distribution of all sequenced clones is assumed to follow a Poisson function, nearly 73% of all unique cDNAs represented in the library (FIG. 1) were recovered. After sequencing, each non-redundant EST deposited in the database becomes an individual record. The record consists of the EST identification name (EST ID), GenBank accession number, cDNA sequence, functional category and subcategory, in situ data (if available), and GenBank BLAST results (Altschul, S., et al., (1990), J. Mol. Biol. 3, 403-410) containing links to Entrez-PubMed (FIG. 2). The description of the *S. mediterranea* cDNA sequence is determined by the expectancy value of the obtained GenBank return. Records retrieving significant matches from GenBank (E value $\leq$−4) are appended with the top scoring gene description. Low scoring hits (E value $\geq$−4) are tagged as "No Significant Match" and a sequence without a homologue or "hit" is noted as "No Match". Reciprocally, access to SmedDb from Gen-Bank is facilitated by hyperlinks to SmedDb found in every *Schmidtea mediterranea* GenBank entry.

d) Functional Categorization of ESTs

The descriptions assigned to each EST by the above-described procedure served to place each cDNA with homologues in GenBank into putative functional categories (FIG. 3). The nomenclature for such categories were derived from the expressed gene anatomy database (EGAD; http://www.tigr.org) and the gene ontology (http://www.geneontology.org) functional classification systems. There are twelve functional categories, each of which is composed of specific subcategories for a total of forty six subcategories (FIG. 3). Examples of functional categories are "Cell defense", "Cell-cell communication", "General metabolism", genes of unknown function with homologues in the extant databases ("Unknown Function") and genes with no known homologues ("No Match"). Approximately 69% of the ESTs share significant similarities with sequences present in GenBank and therefore belong to categories other than "no match". For instance, there are at present 56 ESTs defined as being similar to cell cycle/cell division genes, 44 putatively involved in RNA processing, and 77 cDNAs with high homology to transcription factors.

e) Searching SmedDb

SmedDb can be searched by accession number, category and subcategory, or by carrying out direct sequence comparisons of sequences of interest against the *S. mediterranea* cDNAs using a stand-alone BLAST application available in SmedDb. The search interfaces can be accessible on a web site by selecting "SmedDB Search" from the top or side menu bar (FIG. 3). The database can then be searched by any of the following methods:

Accession Number. If the accession number is known it can be used to find the corresponding record by typing it into the text box found at the top of the search page (FIG. 3). Once the "search by Accession Number" button has been selected, an executive summary of the record will be displayed. Included in this output are the EST ID, accession number, description, category, subcategory, a link to the entire record ("More Info"), and a link to the in situ data if it is available (FIG. 4).

Categories. If an accession number is not known and one wishes to review specific types of genes, SmedDb can be searched by functional categories on the same "SmedDb search" page (FIG. 3). When using this search tactic, different combinations of categories and subcategories can be selected. In order to avoid redundancy of search results by using this method, each EST record is present only in one subcategory, which in turn is unique to a given functional category. When one category check box is selected all records, belonging to this category, will be displayed. If only one subcategory is selected only the records belonging to that subcategory will be presented. Since category selection supersedes subcategory selections, an uninformative combination of choices would be, for example, the selection of a category and one of its subcategories. The resulting output would include all records belonging to the chosen functional category. However, if two subcategories from two different categories are selected, only the records belonging to the chosen subcategories will be returned. To narrow or broaden the results of any of the category/subcategory searches, the "refine search" button (found at the bottom of the results page) can be used. This action will return the browser to the previous search page with all former search guidelines intact. The prior search can now be appropriately altered.

BLAST. SmedDb can also be searched via BLAST (Altschul, S., et al., (1990), J. Mol. Biol. 3, 403-410). A query sequence can be used to identify any similar planarian EST. A link, "Search via BLAST", located at the bottom of the "SmedDb search" page and also on the side and top bars can be visited to utilize this search (FIG. 3). For output purpose, this search requires the typing of a search name into the first textbox (FIG. 5a). Currently, BLAST in SmedDb supports BLASTn for nucleotide comparisons and tBLASTn for comparing amino acid sequences against S. mediterranea cDNAs. If deemed necessary, the expected value can be altered from the default value of 10. The query sequence (nucleotides or sinble-letter amino acids) is then entered in the "Sequence" textbox (FIG. 5a). Once the search is complete a new window will appear with the results (FIG. 5b). SmedDb EST IDs will be displayed in a list, and are hyperlinked to the corresponding EST record in SmedDb. This type of search is useful to determine which of the Schmidtea mediterranea sequences match an investigator supplied query sequence (nucleotide or amino acid) and to view the corresponding spatial expression patterns of the planarian homologue.

f) SmedDb is Regularly and Automatically Updated to Obtain the most Recent GenBank BLAST Comparisons For SmedDb to be a useful resource for a lab and for the regeneration community, it is necessary for the data to be as up-to-date as possible. Given the large number of DNA sequences being deposited into GenBank (http://www.ncbi.nlm.nih.gov/Genbank/genbankstats.html), static databases run the chance of quickly becoming obsolete. SmedDB is kept current by an automated process that routinely sends all sequences to GenBank for homology comparisons. If the comparisons have changed the appropriate EST record is then automatically updated.

2. Example 2

The Schmidtea mediterranea Database as a Molecular Resource for Studying Platyhelminthes, Stem Cells and Regeneration Platyhelminthes are excellent models for the study of stem cell biology, regeneration and the regulation of scale and proportion. In addition, parasitic forms infect millions of people worldwide. Therefore, it is puzzling that they remain relatively unexplored at the molecular level. The characterization of 3000 non-redundant cDNAs from a clonal line of the planarian Schmidtea mediterranea are herein presented. The obtained cDNA sequences, homology comparisons and high-throughput whole-mount in situ hybridization data form part of the S. mediterranea database (SmedDb). Sixty-nine percent of the cDNAs analyzed share similarities with sequences deposited in GenBank and dbEST. The remaining gene transcripts failed to match sequences in other organisms, even though a large number of these (~80%) contained putative open reading frames. Taken together, the molecular resources presented in this study, along with the ability of abrogating gene expression in planarians using RNA interference technology, pave the way for a systematic study of the remarkable biological properties displayed by Platyhelminthes.

a) Materials and Methods (1) Planarian Culture

Clonal lines of the diploid, asexual strain of S. mediterranea from Barcelona, Spain (Benazzi, M., et al., (1972), Caryologia 25, 59-68) were generated in the laboratory by allowing individuals to undergo numerous fission cycles, feeding the regenerated fission progeny three to five times each week, and then amputating the fission progeny into multiple pieces when they had reached full size. The animals were fed on homogenized baby beef liver paste and maintained as previously described (Newmark, P. and Sánchez Alvarado, A. (2000), Dev. Biol. 220, 142-153).

(2) cDNA Library Preparation

Heads and 2-3 day regeneration blastemas were isolated from individuals of asexual clonal line CIW4. Amputated tissue was immediately frozen in liquid nitrogen and stored at −80° C. until use. Total RNA was isolated using TriZol reagent (BRL/Life Technologies); poly(A)+RNA was prepared using oligo d(T) cellulose (BRL/Life Technologies). Standard procedures were used to synthesize and size-select the oligo d(T) primed cDNAs; the resulting cDNAs were directionally cloned into the EcoRI and XhoI restriction sites of pBluescript II SK (+) and electroporated into DH10B cells. Unamplified cDNA libraries were replica plated on nitrocellulose filters and grown on LB/carbenicillin plates. One set of replicate filters was used for hybridization to identify abundant clones; these were excluded from subsequent rounds of analysis. The second set of filters served as master filters for recovery of non-redundant clones; these filters were stored on LB/glycerol plates at −80° C. Non-redundant clones were picked and grown overnight at 37° C. in Magnificent Broth (MacConnell Research) with 100 mg/ml carbenicillin. Plasmid isolations were performed using a MiniPrep24 machine (MacConnell Research).

(3) Sequence Analysis, Bioinformatics and the S. mediterranea EST Database (SmedDb)

Sequencing reactions were performed using Big Dye Terminator chemistry and the resulting products were run on an ABI Prism 377 DNA sequencer. The sequencing strategy is outlined in FIG. 1A. Obtained sequences were compared against one another using stand alone BLAST (Altschul S, et al., 1990, J Mol Biol 3:403-410) as a way to measure internal redundancy and to identify unique clones. Statistical analysis of the frequency distribution of unique sequences indicates that the non-redundant clones identified represent a significant proportion of the complexity of the libraries (50-55%). In order to allow the management and internet browser accessibility of the data, unique sequences were deposited in a server database running Cold Fusion 4.5 (Allaire) and batch analyzed at GenBank for homology comparisons using BLASTc13 running either nucleotide-nucleotide (BLASTn) or translated (BLASTx) searches. In addition, dbEST was also queried using BLASTn, BLASTx and tBLASTx. Given the number of new sequences being continuously deposited into GenBank, SmedDb has been programmed to update the BLAST results for all planarian ESTs on command and/or automatically once a week.

Whole-Mount In Situ Hydbridization

Planarians (3-5 mm in length) and starved for at least 1 week were treated with 2% HCl for 5 minutes on ice, and then fixed on ice for 2 hours in Carnoy's fixative (EtOH:CHCl3: acetic acid, 6:3:1) (Umesono et al., (1997), *Dev. Growth Differ.* 39, 723-727). After 1 hour in methanol at −20° C., the planarians were bleached in 6% $H_2O_2$ in methanol at room temperature. Bleached planarians were loaded into incubation columns in an Insitu Pro hybridization robot (Abimed/Intavis, Germany) and processed as described (Sánchez Alvarado, A. and Newmark, P. A. (1999), *Proc. Natl. Acad. Sci. USA* 96, 5049-5054) with modifications to accommodate the liquid handling characteristics of the machine.

(4) GenBank Accession Numbers

GenBank accession numbers were: AY066058-AY066260; AY066262-AY066313; AY066315-AY066438; AY066440-AY067204; AY067206-AY068336; AY068339-AY068349; and AY068675-AY069025.

b) Results (1) The *S. mediterranea* Database

Two tissue-specific cDNA libraries made from the heads (H) and head blastemas (HB) of *S. mediterranea* clonal line CIW4 were used to generate expressed sequence tags (ESTs). Previous sequence analyses of 54 different cDNA clones obtained by subtractive hybridization (Sánchez Alvarado, A. and Newmark, P. A. (1998), *Wound Rep. Regen.* 6, 413-420) demonstrated that the average length of 3¢-untranslated sequences (3¢-UTRs) in this species is ²350 nucleotides. Therefore, to maximize output, minimize the sequencing effort and reduce the complexity of the computational analyses, only the 3'-ends were sequenced of all cDNA clones isolated from the H and HB libraries. Only clones that failed to display an open reading frame (ORF), or had no homology to GenBank sequences were selected for 5'-end sequencing (FIG. 1A). cDNA clones (5561 clones) representing 2979 non-redundant gene products were sequenced and characterized as shown in FIG. 1A. Of these, 972 cDNAs were sequenced from their 5' ends and subjected to the same bioinformatic protocol (FIG. 1A). Analysis of the EST collection revealed that ~69% of the entries share similarities with sequences deposited in GenBank and dbEST. The remaining 31% bear no similarity to known sequences in other organisms, even though the majority contained putative ORFs (~80%). This subset of possibly *S. mediterranea*- or platyhelminth-specific sequences is similar in number to the percentage of genes found to be species-specific in the proteomes of *S. cerevisiae, C. elegans* and *D. melanogaster* (Rubin, G. M., et al. (2000), *Science* 287, 2204-2215).

The high percentage of planarian ESTs with putative orthologs in the public databases allowed further organization of SmedDb into functional categories (FIG. 1B). The categories employed are derived from the expressed gene anatomy database (EGAD; http://www.tigr.org) and the gene ontology (http://www.geneontology.org) functional classification systems. Each entry in SmedDb consists of the cDNA name, similarity description and expression pattern, if available (see below). Selecting an entry in the database provides additional information such as the sequence sent for analysis, the assigned functional category, in situ hybridization data and the corresponding BLAST results linked to Entrez-PubMed. Examples of SmedDb entries placed into functional categories are shown in Table 1.

TABLE 1

Examples of *S. mediterranea* sequences placed into functional categories in SmedDb

| Category | Subcategory | Clone ID | Description |
|---|---|---|---|
| RNA metabolism | Transcription factors H.119.4D Class IV POU-homeodomain protein | H.119.4 | Class IV POU-homeodomain protein |
| | | H.17.9E | Smad4 |
| | | H.38.3f(T3) | LIM/homeobox protein LIM (HRLIM) |
| | | H.8.6C | Homeobox protein DTH-2 |
| | | H.110.1c | Pre B-cell leukemia transcription factor 2 (Pbx-2) |
| DNA replication/modification | Chromosome/nuclear structure | H.90.1e(T3) | Sirtuin 6 |
| | | HB.19.8F | Histone acetyltransferase MORF |
| | | H.25.11e(T3) | Maleless gene product |
| | | H.10.6c(T3) | Karyopherin α 3 |
| | Apoptosis | H.105.11H | Apoptosis inhibitor 2 |
| | | H.8.7G | Caspase 6 precursor |
| | | H.57.1d | Probable Bax inhibitor 1 |
| Cell-cell communication | Receptors | E-99 | FGF homologous factor receptor |
| | | H.103.12E | Cysteine-rich fibroblast growth factor receptor |
| | | H.111.10F | GABAA receptor associated protein |
| | Other membrane proteins | H.110.2E | Mechanosensory protein 2 |
| | | H.119.4E | Endothelin converting enzyme |
| | | H.44.6a(T3) | Serrate 2 |

TABLE 1-continued

Examples of *S. mediterranea* sequences placed into functional categories in SmedDb

| Category | Subcategory | Clone ID | Description |
|---|---|---|---|
| Intracellular signaling | Channels/transporters | H.102.1B | Delayed rectifier K + channel |
| | | H.90.5b(T3) | Cu 2+ transporter (Menkes disease-associated protein) |
| | | H.16.11G | Na + /K + −ATPase a-subunit |
| | Transduction | H.2.10h(T3) | Rab GDP-dissociation inhibitor |
| | | H.31.11B | GTP-binding regulatory protein Gs α chain |
| | | H.56.3A | cAMP-dependent protein kinase catalytic subunit |

Complete lists for each category and their respective subcategories can be found and searched in SmedDb. POU, Pit, Oct, Unc DNA-binding domain; Smad, similar to mothers-against decapentaplegic; LIM, Liml1, Isl1, Mec3 protein-binding domain; DTH, Dugesia tigrina homeobox; Pbx, post-bithorax; MORF, monocytic leukemia zinc finger protein-related factor; Bax, Bcl2 associated X gene; FGF, fibroblast growth factor, GABA, gamma amino-butyric acid; GDP, guanosine diphosphate; GTP, guanosine triphosphate; cAMP, cyclic adenosine monophosphate.

At least 77 transcription factors, 130 DNA replication/modification molecules and 97 receptors, channels and other membrane-associated proteins were putatively identified.

Interestingly, when the planarian ESTs with significant homologies to GenBank are ranked by lowest expectancy value, 64% of the entries in SmedDb have highest overall similarities to vertebrate rather than to invertebrate sequences (FIG. 1C). When comparative BLASTx analyses between SmedDb and the proteomes of *C. elegans, D. melanogaster* and *H. sapiens* were performed, a set of 124 *S. mediterranea* ESTs with significant similarity only to proteins found in the human genome were revealed. Sixty-three of these are similar to human genes encoding proteins of unknown function. Noteworthy is the presence in *S. mediterranea* of thymidine phosphorylase/endothelial cell growth factor 1 (BLASTx $E=5\times10^{-30}$), acyl-CoA dehydrogenase (BLASTx $E=2\times10^{-21}$), epoxide hydrolase (BLASTx $E=5\times10^{-29}$) and formiminotransferase cyclodeaminase (BLASTx $E=4\times10^{-42}$). These genes were recently postulated to be present in the human genome as a result of direct horizontal gene transfer (HGT) between bacteria and vertebrates based on their absence in the genomes of *C. elegans* and *D. melanogaster* (Lander, E. et al. (2001), *Nature* 409, 860-921). However, the presence of these transcripts in planarians suggests that these loci are most probably not shared by bacteria and vertebrates via HGT, but rather by descent through common ancestry (Kyrpides, N. C. and Olsen, G. J. (1999), *Trends Genet.* 15, 298-299; Stanhope, M. J., et al. (2001), *Nature* 411, 940-944).

(2) High-Throughput In Situ Hybridization

The ~3000 independent ESTs available in SmedDb provide a wealth of material for studying the flatworms. One such use will be for identifying cell type- and region-specific markers. Thus, whole-mount in situ hybridization has been used to begin to determine the spatial expression patterns of SmedDb entries; to date, results from nearly 300 clones have been deposited in SmedDb, and more are being added regularly as they become available. The analysis has revealed some surprising complexities in the spatial expression patterns of many of the genes represented in the EST collection (FIG. 2). For example, the morphologically simple cephalic ganglia of flatworms display a diverse array of expression domains, some of which are depicted in FIG. 2A (see figure legend for explanation). In addition, other organ-system-specific genes have been identified that label the gastrovascular system, the dorsal epithelium, the excretory system and the pharynx (FIG. 2B from top to bottom). Transcripts were also found to be expressed in various subsets of cells, including the planarian neoblasts in which piwi, a transcript found in many metazoan stem cells (Benfey, P. N. (1999), *Curr. Biol.* 9, R171-172), can be detected (FIG. 2C, bottom picture). Striking expression patterns defining both dorsal and ventral boundaries have been observed as well. This is illustrated by the lateral view of in situ hybridization results using clone H.8.1f, which has no known homolog in the available databases (FIG. 2D).

(3) Cell Loss During De-Growth

Figure 12A:
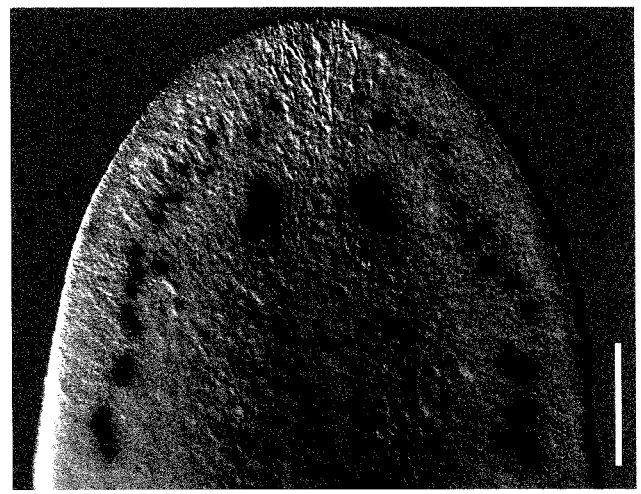
Figure 12B:
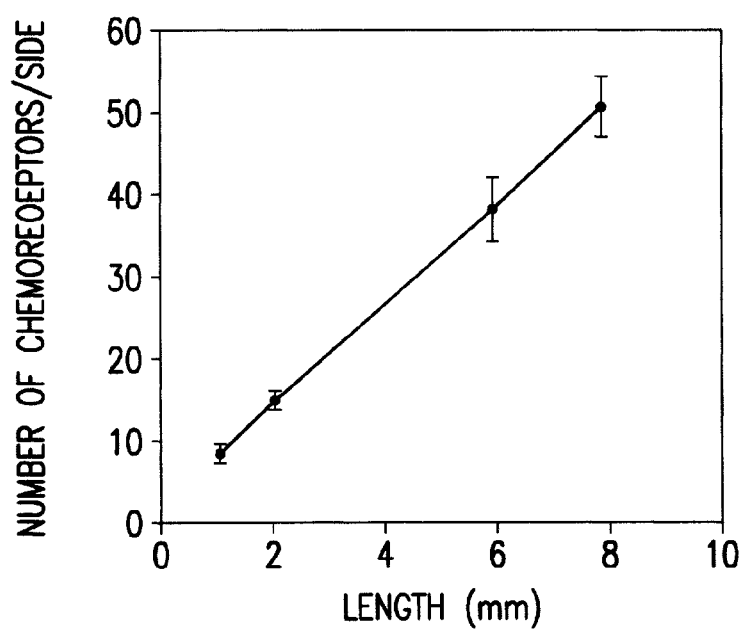

The identification of cell type-specific markers from the large-scale in situ hybridization screen provides new tools for studying morphallaxis, a classic problem first defined by Morgan in 1898 (Morgan, T. H. (1898), *Arch. Entw. Mech. Org.* 7, 364-397). Morphallaxis refers to the remodeling that occurs when small fragments of planarians (or other organisms, like Hydra) restore their appropriate proportion and pattern without adding additional tissue. In addition to this remodeling during regenerative events, planarians show a high degree of plasticity in their ability to either grow or de-grow, depending upon environmental conditions. During periods of prolonged starvation, planarians will shrink (Lillie, F. R (1900), *Am. Nat.* 34, 173-177; Schultz, E. (1904), *Arch. Entwm.* 18, 555-577; Berninger, J. (1911), *Zool. Jahrb.* 30, 181-216; Child, C. M. (1911), *J. Exp. Zool.* 11, 220-280; Abeloos, M. (1930), *Bull. Biol.* 1, 1-140): a 20 mm long worm can be reduced to less than 1 mm over the course of several months. This change in body size is due to an overall reduction in total cell number, as opposed to a reduction in cell size (Baguñà, J. and Romero, R. (1981), *Hydrobiologia* 84, 181-194; Romero, R. and Baguñà, J. (1991), *Invert. Reprod. Dev.* 19, 157-165). Previous studies of this phenomenon have used techniques in which planarians are macerated into a suspension of individual cells. Using this method, roughly 13 different cell types from organisms in varying stages of growth and de-growth were classified and quantitated (Baguñà, J. and Romero, R. (1981), *Hydrobiologia* 84, 181-194; Romero, R. and Baguñà, J. (1991), *Invert. Reprod. Dev.* 19, 157-165). Because the flatworms were dissociated into single cells in these studies, the distribution of the cells could not be monitored in the whole animal as it changed in size. Furthermore, the morphological criteria alone underestimated the true number of different cell types in the planarian.

cDNA clone H112.3c shows weak sequence similarity to degenerin 1 from *C. elegans* and is expressed in a subset of cells near the anterior margin of the planarian (FIG. 3A); these cells are likely to be involved in chemoreception through ciliated pits that lie at the ciliated anterior margin in this genus (Farnesi, R. M. and Tei, S. (1980), *Riv. Biol.* 73, 65-77). The number of H112.3c-expressing cells can be counted easily in organisms of different sizes after whole-mount in situ hybridization. Remarkably, the number of these cells increases linearly with length (FIG. 12B), suggesting that even for cell types comprising a small percentage of the body (~0.03%), their total numbers are regulated as the animal grows and shrinks.

c) Discussion

Considering that flatworms comprise the fourth largest phylum on Earth (Brusca, R. C. and Brusca, G. J. (1990). *Invertebrates*. Sunderland, MA: Sinauer Associates) and that many of its members have challenged scores of biologists and biomedical researchers, it is puzzling that the molecular biology of the Platyhelminthes has remained largely unexplored. The problems of regeneration, de-growth and proportion regulation remain as puzzling today as they were over 200 years ago. Furthermore, diseases such as Shistosomiasis, which is caused by members of this phylum, continue to be global public health problems with no signs of abating. Thus, deciphering the molecular principles underpinning the biology of these organisms should not only improve our knowledge of the phylum, but also contribute to the fields of developmental biology and biomedicine.

The establishment of a clonal line (CIW4) of the freshwater planarian *S. mediterranea* and the identification of nearly 3000 non-redundant cDNAs from this line will aid the molecular study of the most salient biological properties of this taxon. Nearly 70% of all *S. mediterranea* clones share significant homologies to sequences deposited in GenBank (FIG. 1B), and a large number of these have highest similarity to the deuterostome branch of the metazoans (FIG. 1C). These results indicate either a closer proximity of the phylum to the deuterostome lineage as recently proposed by Tyler (Tyler, S. (2001), The early worm: origins and relationships of the lower flatworms. In *Interrelationships of the Platyhelminthes* (ed. T. J. Littlewood and R. A. Bray), pp. 3-12. London, New York: Taylor and Francis), or are more likely a reflection of the poor representation of invertebrate sequences in current databases. The latter possibility is illustrated by the identification in planarians of cDNAs encoding proteins that until recently were ascribed to be present only in bacteria and vertebrates based on a comparative analysis of the human, fly and nematode genomes (Lander, E. et al. (2001), *Nature* 409, 860-921). The presence of Thymidine phosphorylase/endothelial cell growth factor 1, acyl-CoA dehydrogenase, epoxide hydrolase and formiminotransferase cyclodeaminase in *S. mediterranea* suggests that these loci reached the vertebrates by common ancestry and not by horizontal gene transfer as originally proposed (Lander, E. et al. (2001), *Nature* 409, 860-921). Therefore, even though the proteomes of both *C. elegans* and *D. melanogaster* have been deposited in GenBank, limiting sequence comparisons to these two invertebrates is not sufficient to draw sound phylogenetic conclusions, especially on the basis of BLAST results alone. Only rigorous phylogenetic analyses can most closely approximate phyletic relationships and the sequences in SmedDb contribute to the production of higher resolution intra- and inter-phyletic metazoan relationships.

In addition to sharing a large number of genes with the human, fly and nematode genomes, it should be noted that several planarian cDNAs with significant similarities to human sequences were not identified in the *C. elegans* or *D. melanogaster* genomes by BLAST searches. At least 63 of these cDNAs are similar to human genes encoding proteins of unknown function. Therefore, *S. mediterranea* is likely to expand and complement the repertoire of organisms used for the study of genes and pathways involved in various aspects of human biology and disease.

The high-throughput in situ hybridization analyses serve as a first step in deciphering the roles of genes encoding proteins of unknown function. The tissue- or cell type-specific expression patterns of these genes can provide hints as to their function. For example, cDNA clones H.14.5b and H.12.6g share similarity with human genes for which no function is known (hypothetical protein XP_044953.1; $E=5e_{-9}$ and unnamed protein product AK022687; $E=1e_{-12}$, respectively), and are expressed in neurons of both the planarian central and peripheral nervous system. The fact that double-stranded RNA can be used to inhibit gene expression in planarians (Sánchez Alvarado, A. and Newmark, P. A. (1999), *Proc. Natl. Acad. Sci. USA* 96, 5049-5054) provides the means for testing gene function on a large scale, thus allowing the functional characterization of novel, evolutionarily conserved gene products.

Furthermore, cell type-specific markers identified by large-scale in situ screens provide useful reagents for examining the processes of patterning, differentiation and remodeling in intact and regenerating planarians. It has been shown the use of such a marker (H.112.3c) to quantify cell number changes as planarians alter their size, and found that these animals also regulate accordingly the numbers of a specific cell type (FIG. 3). This maintenance of pattern and proportion is a fascinating corollary to the regenerative abilities displayed by these organisms. In addition, little is known about the heterogeneity of the stem cell population in planarians and markers such as piwi (H.2.12c) will provide necessary reagents for analyzing the processes by which neoblasts differentiate to give rise to the ~30 cell types in the animal. The tools described make these daunting problems more amenable to molecular dissection.

Finally, BLASTn and BLASTx queries also revealed that 31% of the cDNAs obtained do not share sequence similarities with the available databases. This lack of similarities with GenBank and dbEST is not due to the divergences commonly found in untranslated sequences, because only ~20% of these cDNAs lack a putative ORF. These results suggest that some of these sequences can correspond to Platyhelminth-specific genes. Therefore, in addition to its obvious advantages for studying the problem of regeneration, the easily manipulatable planarian provides a free-living counterpart likely to complement current research efforts on the parasitic forms, in particular *Schistosoma mansoni* and *S. japonicum*, for which abundant sequence data are being obtained (Snyder, S. D., Loker, E. S., Johnston, D. A. and Rollinson, D. (2001). The Schistosomatidea: advances in phylogenetics and genomics. In *Interrelationships of the Platyhelminthes* (ed. T. J. Littlewood and R. A. Bray), pp. 194-199. London: Taylor & Francis). Given that the parasitic flatworms are difficult experimental subjects, the ability to identify flatworm-specific genes through comparisons to *S. mediterranea* sequences should help identify candidate molecules for therapeutic intervention. Furthermore, the in situ hybridization data being generated in *S. mediterranea* will help identify genes expressed in cell types unique to the platyhelminthes, providing additional potential therapeutic targets. The combination of sequence comparisons, gene expression patterns, and RNAi technology provide new experimental possibilities for studying the free-living and parasitic members of this phylum. Thus, the SmedDb resources will be useful to a wide gamut of developmental and biomedical endeavors.

3. Example 3

Design, Implementation and Deployment of a Commodity Cluster for Periodic Comparisons of Gene Sequences The following is a case study on the design, implementation, and deployment of a low cost cluster for periodic comparisons of gene sequences using the BLAST algorithms. This example demonstrates that it is possible to build a scalable system that can accommodate the high demands placed by the need for continuous updating of the existing comparisons due to newly available genetic sequences. Described is how the scientific problem at hand was translated into system requirements and architectural design. Special attention is given to the scheme devised for the updates of the databases, which was implemented to avoid interference between long running jobs and database updates.

a) System Requirements and Design

The design of the system proceeded using the following guiding principles derived from the scientific considerations described above along with the financial and operational constraints.
 i) All the components of the cluster should be off-the-shelf to keep costs within the budget and that typically available at common biomedical labs.
 ii) The initial computing capacity of the search engine for the cluster should allow to process in parallel most of the updates to SmedDb in less than 48 hours.
 iii) The cluster should be scalable, so the computing capacity can be increased as the size of the SmedDb and NCBI databases increase.
 iv) the scalability of the cluster should allow the addition of computing capacity to support other users in our institution with similar requirements.
 v) The download and processing of updated NCBI databases should proceed without interfering with ongoing searches. This is important because when performing searches lasting more than 24 hours there is a considerable probability that updates can be occurring during the processing time.
 vi) Database updates, process scheduling, submission of searches and retrieval of the results should be as automatic as possible to allow for high-throughput without human intervention. But the system should allow for intervention when necessary to make judicious evaluations of the results.
 vii) While in this implementation the parallel cluster search system has been integrated to the SmedDb, the design should be flexible enough to permit its integration to diverse laboratory-specific data management systems.

Previously, the fundamental constraint in the design was the data management scheme needed to update and distribute the database files containing the approximately 15 Gbytes of data deposited in the major NCBI databases. The key issue was how to move this relatively large amount of data across the system in a manner which does not create bottlenecks that affect the scalability or run time goals of the project. While it was obvious that the performance targets were achievable using more expensive proprietary solutions, their use would conflict with the desire to use commodity hardware to keep the cost of the system down.

In the design of the system there were two choices for the location of the databases: i) to have a global repository for the data files or ii) to replicate the files locally on each compute node of the system. There are obvious disadvantages with both of these options; the first can produce an IO bottleneck when several processors try to access the same files, while the second can require significant time for the data migration of the files to all the nodes on the cluster and significantly increase the total amount of disk required to implement the system. To better understand the requirements, extensive tests of the IO behavior of BLAST searches in a cluster environment were performed. The results showed that neither of the models was totally satisfactory and that the results were highly dependent on the nature of the scheduled search. A hybrid model was implemented in which two generations of the formatted NCBI data files are kept in globally accessible space. Searches have the option of using these copies of the databases or replicating the necessary database files on a disk local to the compute nodes at run time. If the submitted job will be running over the entire course of the nightly database update, a process that takes about three hours, the user must make a local copy; however short runs do not have to waste the computer time that making a copy takes. The use of a copy of the database on local disk also permits a user to run multiple searches on different nodes using different versions of the databases. The current implementation uses remote copy to transfer the files from the global space to the individual nodes assigned to a given search, requiring multiple reads of the globally storage files. GridFTP is capable of achieving this purpose, for example, for replicating the files, decreasing the load on the file server and consequently increasing the scalability as the number of search nodes is increased to meet the needs of additional researchers.

The next area of concern was the downloading of the daily updates of the NCBI database files without degrading the performance of the rest of the system that was running searches. To solve this problem a separate node was used to process the download of the data sets. Taking advantage of the low cost of commodity disks it was possible to acquire a large disk space that allows keeping multiple copies of the databases while using a clever update scheme that precludes interference between the updates and the searches. This scheme is explained in detail below.

The computational capacity of the cluster can be easily scaled to meet the time requirements by adding processors to the system. Note that by decomposing the input search streams as described below, it is possible to obtain almost perfect linear parallel performance improvement of the searches. This scheme makes the searches parallel, isolating scalability issues to the data management and IO schemes discussed above.

b) Hardware Configuration

The final hardware configuration for the cluster (see FIG. 13) consists of eight dual processor AMD Athlon MP 2000+ search nodes each with 2 GB of RAM and a moderate (60 GB) amount of local disk provided for the option of using local space for storage of the database files. The core file server, used to provide the global disk space, is also a dual AMD Athlon MP 2000+ with 1 GB of RAM and 240 GB of usable space in a RAID array configuration, optimized for NFS read performance. This node is also used to provide cluster services like scheduling, accounting, etc. A specialized node was added for processing the daily updates of the database files.

The performance of this node is not relevant as most of the delays in the downloading of the databases are introduced by the network and source host constraints. The local space is this node is used to hold the newly downloaded NCBI database files and to provide space to untar the files before migrating them to the global file server. The intent of this design is to keep the nightly database updates from impacting the load on the global file server as much as possible. Finally an interactive node was added to allow users to gain a login shell access to interact with the queuing system as needed. All of the nodes in the cluster are internally connected via a GigE 9 network using a Foundry Big Iron 15000 switch supporting jumbo frames. The internal connection of the nodes via a private vLAN makes them inaccessible from outside the cluster. The interactive node (sequence) and the node for database updates (seqdat) are multi-ported, connected to both to the campus wide area network and to the private network with the rest of the nodes. This scheme provides a higher degree of security by concentrating the access points to two nodes and eliminating the possibility of external threads on the rest of the nodes of the cluster.

c) Software Configuration

All the nodes of the cluster are running LINUX Redhat 8.0 as the operating system. OpenPBS 2.3.16 (http://www.openpbs.org) is used for resource management, Maui 3.2.6 (http://www.supercluster.org) for scheduling the jobs, and QBank 2.10 (http://www.emsl.pnl.gov/docs/mscf) for the accounting. In its current implementation, with the system being used only by one research group, it would be possible to manage the job of scheduling manually or by some easy to implement cron job. However, OpenPBS and Maui were still implemented as a feature-rich queue system (D. B. Jackson, B. Haymore, J. C. Facelli, and Q. O. Snell, "Improving Cluster Utilization Through Set Based Allocation Policies," presented at Proceedings International Conference on Parallel Computing, Valencia, Spain, 2001), allows for a scalable software infrastructure that can be used to manage the workflow of numerous research groups when needed.

All nodes are able to run the full BLAST suite of programs that were downloaded from the NCBI site and made available via NFS. After receiving notice from the NCBI mailing list on software updates the programs are updated manually. After installation and testing of the newest code the std link is changed from the old to the new version; using this update mechanism there is no need to make any changes in the scripts, which use the std link nomenclature, preventing interference with already running jobs and providing the flexibility to run searches using previous versions of the software. The current version, 2.2.6 (released Apr. 2003), of the BLAST search codes (blastx, tblastx, and blastn) is being used.

d) Database Files Refreshing Scheme

As discussed above, the task of maintenance of the database files is delegated to a dedicated node of the cluster, seqdat. The procedure to update the local databases from the NCBI ftp site is performed on a nightly basis as a cron job. The large database files are present on this ftp site as preformatted files in FASTA format. On seqdat three database directories are available: ~/db, ~/db_backup, and ~/db_source. The ~/db_source directory, located on a disk local to seqdat as it is only needed for the download process, contains the compressed tar files as received from the NCBI ftp site. The major advantage of having this directory on local disk versus being on a disk that is NFS mounted across the entire cluster is that the file transfer process is extremely slow when there is a search in progress on the rest of the cluster due to the contention between reads from searches and writes from downloads, to the same file system. Our tests show that moving this directory to local disk increased the overall transfer rate by an order of magnitude, from approximately 100 to 1000 kbytes/sec. The remaining two directories, ~/db_backup, and and ~/db, are available to seqdat via a NFS mount from the file server. The directory ~/db contains the current files that are being used in the searches and are maintained in the NFS mounted space accessible to all nodes of the cluster. The directory ~/db_backup also on the core file server, contains the version of the databases from the previous day.

A virtual std link pointing to the ~/db directory with the latest NCBI database files indicates the source of the ~/db files to use in any searches. The first task of the cron job is to make a copy of this directory, to ~/db_backup, and transfer the std link to this copy. Therefore any searches running from this copy that are in progress or that can start during the nightly update will continue accessing the last static copy of the database. After this copy the ftp transfer is done using ncftpget (http://www.ncftp.com) which compares the existing compressed tar files in ~/db_source with those available for download, proceeding to download a file when they are different. Once all of the updated database files available are downloaded, the remaining task is to unpack the compressed tar files into the ~/db directory and move the link back to the newly created database directory. When a user starts a search that can run through a database update, the first step of the job is to make a copy, either on global or local scratch, of the databases which the user will then own. This copy takes just over three hours if the user needs all of the maintained databases for their search. The user's search is then completed on this copy of the database. This allows a user to have a static database for a search that takes multiple days in the event of an update of the NCBI databases during the duration of the run.

e) Job Parsing, Scheduling and Processing

The search sequences provided by the user are given as a set of input files. Every input files contains a number of individual nucleotide sequences, in FASTA format, each of which need to be compared to the sequences in the databases. The input files are named according to the search to be done, according to the following format: ###X12, where ### is the file index currently ranging from 1-164 and X=n, x, t signifies a blastn, blastx, or tblastx search, respectively. blastn is the standard BLAST search in which a nucleotide sequence is compared to sequences in a nucleotide database, blastx searches protein databases to find proteins similar to a translated form of the nucleotide query sequence and finally tblastx compares the translated nucleotide query to translated nucleotide database entries. The blastx searches use the non-redundant peptide sequence database, whereas the blastn searches against the non-redundant nucleotide, est, sts, gss and htgs databases as provided by the NCBI. The initial search only uses blastn and blastx and is designated as the stage one search. Currently this search is done on an approximately weekly basis. For sequences that do not have any hits found during the first stage of similarity searching, a second search needs to be completed. Currently this is the case for approximately 1800 of the 6500 sequences being analyzed for similarities. This second search is the tblastx matching using the non-redundant nucleotide, est, sts, gss and htgs databases, and is designated as the stage two search. This search, due to the translation of both the query sequence and the database entries takes a significantly longer time and it is performed only on a monthly basis. For the current input files containing 6532 sequences the stage one search takes approximately 30 total node hours, while the second stage search on the 1800 "No hits found" sequences, takes over 620 total node hours.

Before starting a new search, a decision has to be made as to whether or not there has been a database update since the last search, as not to repeat an identical search. As stated above, checks are made for updates to the database available at the NCBI ftp site on a nightly basis; however updates are not always available. If there are difficulties present at the NCBI FTP site, several days or even longer can pass between updates becoming available. In addition, a decision on the number of nodes that are available for the search needs to be made. A perl script, shown in FIG. 14, was developed to create the necessary PBS script files which distribute the searches among the available nodes in the cluster.

This script is based on a file structure in which there is a directory $HOME/search which contains the input files. The $HOME/search directory also contains one additional file, searchlist.in, which is a list of the filenames, one per line, of the files containing sequences on which the stage one search must be completed. Each of these input files must exist in the $HOME/search directory. The researchers can add new search sequences by either adding them to an existing input file or creating a new input file. In the later case the filename, which must match the existing convention and have an n or x in the name, must be added to the searchlist.in file.

The output of each of the searches is stored in a new directory inside of $HOME/search. The name of the directory of a given search is based on the date that the search was started and is of the form yyy-mm-dd. In each output directory the results of the search are stored, in this case as html files. There is one output file for each input file that is searched. If only stage one is being done in the search these output files are the entire contents of the output directory. If stage two search is also being completed, the input files generated for this search are also stored in the $HOME/search/yyyy-mm-dd directory, along with a directory TBLASTX which will contain the output of the second stage.

The execution of the perl script first checks the date of the current databases, the one to which the std link points. This is accomplished by running the fastacmd-I on the nonredundant peptide sequence database. This command returns the date of the database, date_db. This date is compared to the date of the databases used in the last search, date_last This date is obtained by taking the last of the date directories (comparing the directory names as numbers and looking for the greatest), and looking at the date posted in the output of this last search on the 1×12 input file. If date_db is not greater than the date_last, the user is told that there has been no database updates since last search and that they should try again not earlier than the next day as database updates are checked on a nightly basis, and the script is exited. If date_db is greater than date_last, then the script proceeds. The user is then prompted as to whether he wishes to perform a first stage search only or a first and second stage search. This is the last input required from the user. At this point the directories under $HOME/search where the output will be stored are created, $HOME/search/yyyy-mm-dd and if necessary $HOME/search/yyyy-mm-dd/TBLASTX.

The remainder of the script writes all the necessary PBS script files and submits them for processing. First, the number of nodes available for the search must be determined. This is done by issuing a showq command and using grep and cut to pull out the number of free compute nodes, allowing for the job to be completed with as many nodes as are available in order to minimize the wall time it takes for the search to be completed. This number, #nodes, can range from zero to eight on the cluster described herein. If zero, the search will default to run on one node.

The perl script then generates the #nodes scripts, named SCRIPT-1 through SCRIPT-#nodes. An example of these scripts is given in FIG. 15. The necessary PBS headers are written to each of these script files, along with the necessary environmental variables and links. In addition, the first portion of each of these scripts involves cleaning up the local scratch space from previous searches followed by installing the necessary databases for the current search onto the local scratch system of each node. This is followed by a round robin process dividing up the searches among the #node script files, with the first input file name in searchlinst.in going to SCRIPT-1, the second to SCRIPT-2, etc until the last PBS script file is reached then returning to SCRIPT-1 and repeating the cycle until the end of searchlist.in is reached. Once the PBS script files are generated they are submitted by the perl script. In principle this method of dividing the workload can lead to significant unbalanced loads on the nodes, but because most of the searches being performed take the same amount of time this static job distribution introduces only minor load imbalance. Alternatively, a client server model in which nodes are able to request new files for processing from a server node when they finish their scheduled tasks can be used. The server node maintains an updated database categorizing the individual searches processed, under processing, and waiting to be processed.

In each of these PBS scripts the stage one search is processed for a given input file followed by, when requested by the user, creation of the second stage input files by parsing of the stage one output to extract the input sequences for which the "No hits found" message and then the second stage search. These input sequences produced in the parsing step are collected in a new second stage input file with the same naming scheme, but with the x replaced with a t, and the second stage search, using tblastx, is then started. After all requested searches are complete on a given input file the PBS job continues with the next input file. At any time the user can monitor the output as well as the status of the batch queues on the system in order to track the progress of the search.

f) Integration with SmedDb

In order to become useful the searches produced have to be uploaded and integrated to the SmedDb system. While the implementation of the search system described above is quite general and can be integrated to any laboratory system, the integration of the search output with SmedDb database is quite specific, tailored to the needs of the research group. Therefore, this integration is presented as an example that can be used when integrating the search system to other laboratories. SmedDb is a web-accessible database which contains *S. mediterranea* sequences, BLAST results, reading frame diagrams, and in situ hybridization images in one output report. Any homologous sequences are displayed with links to NCBI's Entrez and Pubmed.

The architecture of SmedDb as it relates to the cluster search system is given in FIG. 16. The FASTA files generated from SmedDb containing the sequences (ESTs) that need to be compared with the most recently updated version of NCBI databases are uploaded manually to the cluster search system using secure copy (scp). Using the script described above the required the BLAST searches are executed and the output files are downloaded to the SmedDb system also using scp. These search results are stored with the corresponding EST as well as being parsed by a Bioperl (A. Sanchez Alvarado, et al., "The *Schmidtea mediterranea* database as a molecular resource for studying platyhelminthes, stem cells and regeneration," *Development*, vol. 129, pp. 5659-65, 2002) script. The Bioperl script is used to pull out the highest scoring (lowest expectation value) match for each of the searches along with its associated description. This information is then used to update the status of the sequences in SmedDb (having a significant match, no significant match, or no match at all). If a given input sequence has a significant match in the current search further processing needs to be completed. If previous searches have not found a significant match, the search output is marked for review and possible classification by the researcher. If previous searches have already resulted in finding a significant match, the current result is compared to the old result. If the old and new descriptions are the same no change is made in the SmedDb for the given sequence entry. If the description is different, this SmedDb record is flagged and a message is posted requesting manual intervention of the researcher to decide on its reclassification.

g) Performance

The nightly database download process takes just over three hours for databases totaling about 14 GBytes. The copy of the necessary database files to local scratch for the project being described is approx an hour for ~/db needed totaling about 12.5 GBytes. The database updates are performed as not to interfere with any searches that can be in progress.

As described above, the current search is performed on over 6500 input sequences. Of these currently about 1800 are candidates for the second stage search. The time required for a first stage search only is approximately 30 node hours, whereas a complete first and second stage search takes about 620 node hours, or slightly over 3 days if all eight nodes are used. This time is slightly longer than the criteria of most searches being done in 48 hours; however, the majority of searches are stage one only.

The use of this cluster, as it exists today, has room for growth. The current use will take longer as the number of entries in both the private SmedDb and in GenBank increases. For example, when this project was first discussed about a year before it went into production the SmedDb had about 4500 sequences compared to the count of 6500 today. Over the last year the number of entries in the non-redundant nucleotide database increased from just over 1.3 million to 1.5 million, tracking the growth in GenBank entries described in the introduction.

Finally, should the demand exceed the current eight compute nodes, it will be straightforward to add more computing capacity to the cluster. Initially this will involve only the addition of more compute nodes.

h) Conclusions

This paper reports a case study on the development of a dedicated commodity based cluster for the periodic update of gene sequence comparisons. The project has been able to meet the turn around time goals and eliminate a great deal of human labor in the periodic update of the SmedDb system. Our experience shows that it is possible using commodity components to design and deploy a cluster with a configuration optimized for a particular task. The judicious use of low cost hardware combined with a clever update of the databases permits the continuous operation of the system avoiding interference among the updates and long running searches. The cluster described here presents a low cost model for biomedical labs requiring substantially more BLAST searches than can be reasonably performed using the existing NCBI services. As the system is highly scalable it is possible to use this architecture to deploy systems serving from individual labs to departmental and even institutional BLAST search engines.

What is claimed is:

1. A method for managing a biological database, comprising:
   a. receiving a set of biological sequences;
   b. querying a plurality of databases with the set of biological sequences;
   c. receiving query results corresponding to the set of biological sequences from the plurality of databases wherein each of the query results corresponds to a sequence in the set of biological sequences and comprises immunohistological data, in situ hybridization data, functional data, expression data, structural data, complementary deoxyribonucleic acid data, expressed sequence tag data, and pharmacology data, wherein
      immunohistological data comprises data relating to binding of antibodies to tissues;
      in situ hybridization data comprises data relating to localization of a specific segment of a nucleic acid within a tissue section;
      functional data comprises data that identifies a putative or commonly accepted function;
      expression data comprises gene expression data or messenger ribonucleic acid (mRNA) expression data;
      structural data comprises data relating to three-dimensional macromolecular structures of proteins and polynucleotide;
      sequence tag data comprises data relating to gene expression in a given tissue and at a given time; and
      pharmacology data comprises data relating to properties of therapeutic compositions or drugs;
   d. storing the query results in a biological database, wherein each sequence in the set of biological sequences is associated with a record comprising a respective query result from each of the plurality of databases;
   e. periodically performing steps b-d;
   f. receiving, from a user, a request to view a record of one of the set of biological sequences; and
   g. displaying an executive summary of the record comprising the respective query result of step (c).

2. The method of claim 1, wherein the set of biological sequences comprises a nucleic acid sequence, an amino acid sequence, or a combination thereof.

3. The method of claim 1, wherein receiving the set of biological sequences comprises receiving the set of biological sequences from the user.

4. The method of claim 1, wherein the plurality of databases comprises two or more databases selected from a group consisting of one or more National Center for Biotechnology Information (NCBI) databases and one or more other externally curated and maintained specialized databases.

5. The method of claim 1, wherein periodically performing steps b-d comprises performing steps b-d daily.

6. The method of claim 1, further comprising performing one or more bioinformatics functions on the set of biological sequences or the query results.

7. The method of claim 6, wherein the one or more bioinformatics functions comprise a sequence alignment, a gene identification, a protein identification structure prediction, a motif comparison, a biological text analysis, or a combination thereof.

8. The method of claim 1, wherein displaying the executive summary of the requested record comprises formatting the requested record for output to the user.

9. A method for managing a biological database, comprising:
   a. providing a plurality of databases;
   b. determining a version of each of the plurality of databases;
   c. determining if the version of each of the plurality of databases is a current version;
   d. downloading the current version of any of the plurality of databases that is not the current version;
   e. periodically performing steps b-d;
   f. receiving a set of biological sequences;
   g. querying the plurality of databases with the set of biological sequences;
   h. receiving query results corresponding to the set of biological sequences from the plurality of databases wherein each of the query results corresponds to a sequence in the set of biological sequences and comprises immunohistological data, in situ hybridization data, functional data, expression data, structural data, complementary deoxyribonucleic acid data, expressed sequence tag data, and pharmacology data, wherein immunohistological data comprises data relating to binding of antibodies to tissues;

in situ hybridization data comprises data relating to localization of a specific segment of a nucleic acid within a tissue section;

functional data comprises data that identifies a putative or commonly accepted function;

expression data comprises gene expression data or messenger ribonucleic acid (mRNA) expression data;

structural data comprises data relating to three-dimensional macromolecular structures of proteins and polynucleotide;

expressed sequence tag data comprises data relating to gene expression in a given tissue and at a given time; and pharmacology data comprises data relating to properties of therapeutic compositions or drugs;

i. storing the query results in a biological database, wherein each sequence in the set of biological sequences is associated with a record comprising a respective query result from each of the plurality of databases;

j. periodically performing steps b-d;

k. receiving, from a user, a request to view a record of one of the set of biological sequences; and j. displaying an executive summary of the record comprising the respective query result of step (h).

10. The method of claim 9, wherein the plurality of databases comprises two or more databases selected from a group consisting of one or more National Center for Biotechnology Information (NCBI) databases and one or more other externally curated and maintained specialized databases.

11. The method of claim 9, wherein periodically performing steps b-d comprises performing steps b-d daily.

12. The method of claim 9, wherein the set of biological sequences comprises a nucleic acid sequence, an amino acid sequence, or a combination thereof.

13. The method of claim 9, wherein receiving the set of biological sequences comprises receiving the set of biological sequences from the user.

14. The method of claim 9, further comprising performing one or more bioinformatics functions on the set of biological sequences or the query results.

15. The method of claim 14, wherein the one or more bioinformatics functions comprise a sequence alignment, a gene identification, a protein identification structure prediction, a motif comparison, a biological text analysis, or a combination thereof.

16. The method of claim 9, wherein displaying the executive summary of the requested record comprises formatting the requested record for output to the user.

17. A system for managing a biological database, comprising:

a target database node, comprising a first memory and a first processor, wherein the first processor is configured to receive and store query results in the biological database, the biological database comprises a set of biological sequences, each sequence in the set of biological sequences is associated with a record comprising a respective query result, each of the query results corresponds to a sequence in the set of biological sequences and comprises immunohistological data, in situ hybridization data, functional data, expression data, structural data, complementary deoxyribonucleic acid data, expressed sequence tag data, and pharmacology data, wherein immunohistological data comprises data relating to binding of antibodies to tissues, in situ hybridization data comprises data relating to localization of a specific segment of a nucleic acid within a tissue section, functional data comprises data that identifies a putative or commonly accepted function, expression data comprises gene expression data or messenger ribonucleic acid (mRNA) expression data, structural data comprises data relating to three-dimensional macromolecular structures of proteins and polynucleotides, expressed sequence tag data comprises data relating to gene expression in a given tissue and at a given time, and pharmacology data comprises data relating to properties of therapeutic compositions or drugs, further wherein the target database node is configured to receive, from a user, a request to view a record of one of the set of biological sequences and display an executive summary of the record comprising the respective query result;

a query node, comprising a second memory and a second processor, wherein the second processor is configured to periodically download and store a plurality of databases from an external network;

a functional node, comprising a third memory and a third processor, wherein the third processor is configured to periodically query the plurality of databases on the query node with the set of biological sequences from the target database node and send the query results to the target database node; and a network switch node, comprising a fourth memory and a fourth processor, wherein the fourth processor is configured to direct the receipt and storage of the query results in the biological database, the periodic download and storage of the plurality of databases, and the periodic query of the plurality of databases on the query node.

18. The system of claim 17, wherein the set of biological sequences comprises a nucleic acid sequence, an amino acid sequence, or a combination thereof.

19. The system of claim 17, wherein the functional node is further configured to perform one or more bioinformatics functions on the set of biological sequences or the query results and update the target database node.

20. The system of claim 19, wherein the one or more bioinformatics functions comprise a sequence alignment, a gene identification, a protein identification structure prediction, a motif comparison, a biological text analysis, or a combination thereof.

21. The system of claim 17, wherein the plurality of databases comprises two or more databases selected from a group consisting of one or more National Center for Biotechnology Information (NCBI) databases and one or more other externally curated and maintained specialized databases.

22. The system of claim 17, wherein the query node is further configured to periodically download and store the plurality of databases from the external network daily.

23. The system of claim 17, wherein the target database node is further configured to format the requested record for output to the user.

* * * * *

SEQUENCE LISTING

```
<160> NUMBER OF SEQ ID NOS: 9

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence:/ note =
      synthetic construct
<220> FEATURE:
<221> NAME/KEY: misc_feature
<222> LOCATION: 169, 226
<223> OTHER INFORMATION: n=a, t, c, or g
<220> FEATURE:
<221> NAME/KEY: misc_feature
<222> LOCATION: 276
<223> OTHER INFORMATION: n=a, t, c, or g

<400> SEQUENCE: 1
cttctgcaag gtccacagtt accattaaca aatcgagtcc tgcagtaaag gaatatgaaa      60
tgagacaatc ctacaatttt tctggagcac ctatgggggg atcagttcaa attcatagca    120
atgtgtcttc tgctgtagag ggccgagaaa gagaaaagag agaaatgcna gatcttaatg    180
aaaggctagc taattatatt gaaaaggtaa gatttctaga agctcnaaac aaaagattaa    240
caaatgaatt gaatacgtta cgtgaaagat ggggtnaaga agctgaaagg atacgagctt    300
```
tatatgagat tgaaatggat caattgaaaa agttattaga cgaagctgaa gctgctagat    360

<210> SEQ ID NO 2
<211> LENGTH: 60
<212> TYPE: PRT
<213> ORGANISM: Artificial Sequence
<220> FEATURE:
<223> OTHER INFORMATION: Description of Artificial Sequence:/ note = synthetic construct
<220> FEATURE:
<221> NAME/KEY: VARIANT
<222> LOCATION: 2, 48
<223> OTHER INFORMATION: Xaa = any amino acid

<400> SEQUENCE: 2

Asn Xaa Ser Ser Pro Ala Val Lys Glu Tyr Glu Met Arg Gln Ser Tyr
 1               5                  10                  15

Asn Phe Ser Gly Ala Pro Met Gly Gly Ser Val Gln Ile His Ser Asn
             20                  25                  30

Val Ser Ser Ala Val Glu Gly Arg Glu Arg Glu Lys Arg Glu Met Xaa
         35                  40                  45

Asp Leu Asn Glu Arg Leu Ala Asn Tyr Ile Glu Lys
     50                  55                  60

<210> SEQ ID NO 3
<211> LENGTH: 60
<212> TYPE: PRT
<213> ORGANISM: Artificial Sequence
<220> FEATURE:
<223> OTHER INFORMATION: Description of Artificial Sequence:/ note = synthetic construct
<220> FEATURE:
<221> NAME/KEY: VARIANT
<222> LOCATION: 2-10, 13, 14, 17, 18, 20, 21, 23-25, 27-29, 32, 34-38, 42, 45, 47-49, 52, 54, 59
<223> OTHER INFORMATION: Xaa = any amino acid

<400> SEQUENCE: 3

Asn Xaa Xaa Xaa Xaa Xaa Xaa Xaa Xaa Xaa Glu Met Xaa Xaa Ser Tyr
 1               5                  10                  15

Xaa Xaa Ser Xaa Xaa Pro Xaa Xaa Xaa Ser Xaa Xaa Xaa His Ser Xaa
             20                  25                  30

Val Xaa Xaa Xaa Xaa Xaa Gly Arg Glu Xaa Glu Lys Xaa Glu Xaa Xaa
         35                  40                  45

Xaa Leu Asn Xaa Arg Xaa Ala Asn Tyr Ile Xaa Lys
     50                  55                  60

<210> SEQ ID NO 4
<211> LENGTH: 60
<212> TYPE: PRT
<213> ORGANISM: Artificial Sequence
<220> FEATURE:
<223> OTHER INFORMATION: Description of Artificial Sequence:/ note = synthetic construct

<400> SEQUENCE: 4

Asn Gln Asn Ala Ser Ser Ile Arg Thr Ile Glu Met Lys Lys Ser Tyr
 1               5                  10                  15

Gly Val Ser Ala Thr Pro Gly Ala Thr Ser Asn Ile Val His Ser Gly
             20                  25                  30

Val Asn Asn Leu Met Asn Gly Arg Glu Lys Glu Lys Asn Glu Leu Gln
         35                  40                  45

Glu Leu Asn Asp Arg Phe Ala Asn Tyr Ile Asp Lys
     50                  55                  60

<210> SEQ ID NO 5
<211> LENGTH: 60
<212> TYPE: PRT
<213> ORGANISM: Artificial Sequence
<220> FEATURE:
<223> OTHER INFORMATION: Description of Artificial Sequence:/ note =
      synthetic construct
<220> FEATURE:
<221> NAME/KEY: VARIANT
<222> LOCATION: 7, 24
<223> OTHER INFORMATION: Xaa = any amino acid

<400> SEQUENCE: 5

```
Val Arg Phe Leu Glu Ala Xaa Asn Lys Arg Leu Thr Asn Glu Leu Asn
 1               5                  10                  15

Thr Leu Arg Glu Arg Trp Gly Xaa Glu Ala Glu Arg Ile Arg Ala Leu
            20                  25                  30

Tyr Glu Ile Glu Met Asp Gln Leu Lys Lys Leu Leu Asp Glu Ala Phe
        35                  40                  45

Ala Ala Arg Ser Glu Leu Leu Pro Lys Ile Asn Lys
    50                  55                  60
```

<210> SEQ ID NO 6
<211> LENGTH: 60
<212> TYPE: PRT
<213> ORGANISM: Artificial Sequence
<220> FEATURE:
<223> OTHER INFORMATION: Description of Artificial Sequence:/ note =
      synthetic construct
<220> FEATURE:
<221> NAME/KEY: VARIANT
<222> LOCATION: 3, 6-7, 13, 17, 19-21, 24, 26-27, 30, 34-36, 38, 41-43,
      46, 50-53, 55-56, 60
<223> OTHER INFORMATION: Xaa = any amino acid

<400> SEQUENCE: 6

```
Val Arg Xaa Leu Glu Xaa Xaa Asn Lys Arg Leu Thr Xaa Glu Leu Asn
 1               5                  10                  15

Xaa Leu Xaa Xaa Xaa Trp Gly Xaa Glu Xaa Xaa Arg Ile Xaa Ala Leu
            20                  25                  30

Tyr Xaa Xaa Xaa Met Xaa Gln Leu Xaa Xaa Xaa Leu Asp Xaa Ala Glu
        35                  40                  45

Ala Xaa Xaa Xaa Xaa Leu Xaa Xaa Lys Ile Asn Xaa
    50                  55                  60
```

<210> SEQ ID NO 7
<211> LENGTH: 60
<212> TYPE: PRT
<213> ORGANISM: Artificial Sequence
<220> FEATURE:
<223> OTHER INFORMATION: Description of Artificial Sequence:/ note =
      synthetic construct

<400> SEQUENCE: 7

```
Val Arg Ser Leu Glu Asp Glu Asn Lys Arg Leu Thr Asp Glu Leu Asn
 1               5                  10                  15

Asp Leu Lys Asp Gln Trp Gly Asn Glu Thr Ala Arg Ile Lys Ala Leu
            20                  25                  30

Tyr Asp Ser Asp Met Ser Gln Leu Arg Arg Ser Leu Asp Gln Ala Glu
        35                  40                  45

Ala Ser Lys Ala Gln Leu Glu Met Lys Ile Asn Thr
    50                  55                  60
```

```
-continued

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence:/ note =
      synthetic construct

<400> SEQUENCE: 8
cttctgcaag gtccacagtt accattaaca aatcgagtcc tgcagtaaag gaatatgaaa        60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:/ note =
      synthetic construct

<400> SEQUENCE: 9
tgagacaatc ctacaatttt tctggagcac ctatgggggg atcagttcaa attcatagca        60
```